US006958355B2

(12) United States Patent
Druzgala et al.

(10) Patent No.: US 6,958,355 B2
(45) Date of Patent: Oct. 25, 2005

(54) MATERIALS AND METHODS FOR THE TREATMENT OF DIABETES, HYPERLIPIDEMIA, HYPERCHOLESTEROLEMIA, AND ATHEROSCLEROSIS

(75) Inventors: Pascal Druzgala, Santa Rosa, CA (US); Peter G. Milner, Los Altos Hills, CA (US); Jurg R. Pfister, Los Altos, CA (US)

(73) Assignee: ARYx Therapeutics, Inc., Santa Clara, CA (US)

( * ) Notice: Subject to any disclaimer, the term of this patent is extended or adjusted under 35 U.S.C. 154(b) by 154 days.

(21) Appl. No.: 10/251,522

(22) Filed: Sep. 20, 2002

(65) Prior Publication Data

US 2003/0236227 A1 Dec. 25, 2003
US 2005/0037997 A9 Dec. 25, 2003

Related U.S. Application Data

(63) Continuation-in-part of application No. 10/228,670, filed on Aug. 26, 2002, said application No. 10/251,522, is a continuation-in-part of application No. 09/961,542, filed on Sep. 21, 2001, now Pat. No. 6,768,008, and a continuation-in-part of application No. 09/841,351, filed on Apr. 24, 2001, now Pat. No. 6,680,387, said application No. 10/251,522, is a continuation-in-part of application No. 09/961,538, filed on Sep. 21, 2001, now Pat. No. 6,784,199.

(60) Provisional application No. 60/314,792, filed on Aug. 24, 2001, provisional application No. 60/297,838, filed on Jun. 13, 2001, provisional application No. 60/281,982, filed on Apr. 6, 2001, provisional application No. 60/234,423, filed on Sep. 21, 2000, and provisional application No. 60/199,146, filed on Apr. 24, 2000.

(51) Int. Cl.$^7$ ..................... A61K 31/421; C07D 263/58
(52) U.S. Cl. ..................... 514/360; 514/866; 548/221
(58) Field of Search ..................... 548/221; 514/360, 514/866

(56) References Cited

U.S. PATENT DOCUMENTS

| | | |
|---|---|---|
| 4,287,200 A | 9/1981 | Kawamatsu et al. |
| 4,340,605 A | 7/1982 | Kawamatsu et al. |
| 4,376,777 A | 3/1983 | Kawamatsu et al. |
| 4,438,141 A | 3/1984 | Kawamatsu et al. |
| 4,444,779 A | 4/1984 | Kawamatsu et al. |
| 4,461,902 A | 7/1984 | Kawamatsu et al. |
| 4,572,912 A | 2/1986 | Yoshioka et al. |
| 4,687,777 A | 8/1987 | Meguro et al. |
| 4,703,052 A | 10/1987 | Eggler et al. |
| 4,725,610 A | 2/1988 | Meguro et al. |
| 4,873,255 A | 10/1989 | Yoshioka et al. |
| 4,897,393 A | 1/1990 | Iijima et al. |
| 4,897,405 A | 1/1990 | Alessi et al. |
| 4,918,091 A | 4/1990 | Cantello et al. |
| 4,948,900 A | 8/1990 | Iijima et al. |
| 5,002,953 A | 3/1991 | Hindley |
| 5,061,717 A | 10/1991 | Clark et al. |
| 5,120,754 A | 6/1992 | Clark et al. |
| 5,132,317 A | 7/1992 | Cantello et al. |
| 5,194,443 A | 3/1993 | Hindley |
| 5,223,522 A | 6/1993 | Clark et al. |
| 5,232,925 A | 8/1993 | Hindley |
| 5,260,445 A | 11/1993 | Hindley |
| 5,266,582 A | 11/1993 | De Nanteuil et al. |
| 5,480,896 A | 1/1996 | Malamas et al. |
| 5,677,330 A | 10/1997 | Abraham et al. |
| 5,955,616 A | 9/1999 | Ohtani et al. |
| 6,037,359 A | 3/2000 | Shinkai |
| 6,121,288 A | 9/2000 | Matsui et al. |

FOREIGN PATENT DOCUMENTS

| | | |
|---|---|---|
| EP | 0 306 228 A1 | 3/1989 |
| EP | 0 419 035 A1 | 3/1991 |
| EP | 0 528 734 A1 | 2/1993 |
| EP | 0 548 365 A1 | 6/1993 |
| EP | 0 603 419 A1 | 8/1994 |
| EP | 0 684 242 A1 | 11/1995 |
| EP | 0 801 063 A1 | 10/1997 |
| EP | 0 848 004 A1 | 8/1998 |
| EP | 0 818 232 A1 | 6/1999 |
| EP | 0 919 232 A1 | 6/1999 |
| EP | 0 930 299 A1 | 7/1999 |
| EP | 0 953 355 A1 | 11/1999 |
| EP | 0 992 503 A1 | 4/2000 |
| EP | 1 048 659 A1 | 11/2000 |
| ES | 2 154 551 A1 | 4/2001 |
| WO | WO 89/08551 | 9/1989 |
| WO | WO 91/07107 | 5/1991 |
| WO | WO 92/02520 | 2/1992 |
| WO | WO 93/21166 A1 | 10/1993 |

(Continued)

OTHER PUBLICATIONS

Database Caplus 'Online! Chemical Abstracts Service,' Columbus, OH, USA; Database accession No. 128:13261, XP002181181 RN 199167–77–G and 199187–78–8 and JP 09301963 A (Kyorin Pharmaceutical Co., Ltd.) Nov. 25, 1997.

(Continued)

*Primary Examiner*—Barbara P. Badio
(74) *Attorney, Agent, or Firm*—McDonnell Boehnen Hulbert & Berghoff LLP

(57) ABSTRACT

The subject invention provides pharmaceutical compounds useful in the treatment of Type II diabetes. These compounds are advantageous because they are readily metabolized by the metabolic drug detoxification systems. Particularly, thiazolidinedione analogs that have been designed to include esters within the structure of the compounds are provided. This invention is also drawn to methods of treating disorders, such as diabetes, comprising the administration of therapeutically effective compositions comprising compounds that have been designed to be metabolized by serum or intracellular hydrolases and esterases. Pharmaceutical compositions of the ester-containing thiazolidinedione analogs are also taught.

7 Claims, 34 Drawing Sheets

FOREIGN PATENT DOCUMENTS

| WO | WO 97 32863 A1 | 9/1997 |
| --- | --- | --- |
| WO | WO 98/45291 A1 | 10/1998 |
| WO | WO 00/18759 A1 | 4/2000 |
| WO | WO 01/00566 | 1/2001 |
| WO | WO 01 02377 A1 | 1/2001 |
| WO | WO 01/16122 A1 | 3/2001 |
| WO | WO 01/16132 A1 | 3/2001 |
| WO | WO 01/81328 A2 | 11/2001 |
| WO | WO 02/24689 A1 | 3/2002 |
| WO | WO 02/44127 A1 | 6/2002 |

OTHER PUBLICATIONS

Database Caplus 'Online! Chemical Abstracts Service,' Columbus, OH, USA; Database acession No. 127:161819, XP002181182, RN 193544–82–0 and JP 09165371 A (Sankyo Co., Ltd.), Jun. 24, 1997.

Kletzien, R.F., et al., "Enhancement of Adipcyte Differenttation by an Insulin–Sansitizing Agent," *Molecular Pharmacology* (Feb. 1, 1992) 41(2):393–8, XP002081233, The American Society for Pharmacology and Experimental Therapeutics.

Sohda, T., et al., "Studies on Antidiabetic Agents, II. Synthesis of 5–[4–(1–Methylcyclohexylmethoxy)–benzyl]thiazolidine–2,4–dione (ADD–3878) and its Derivatives," *Chem. Pharm. Bull.* (1982) 30(10):3580–3600. XP002042079.

Urangst, P.C., et al., "Synthesis and Biological Evaluation of 5–[[3,5–Bis(1,1–dimethylethyl)–4–hydroxy phenyl]methylene]oxazoles, –thiazoles, and –imidazoles: Novel Dual 5–Lipoxygenase and Cyclooxygenase Inhibitors with Antiinflammatory Activity," *J. Med. Chem.* (1994) 37(2):322–8, XP002127023, American Chemical Society.

Kinoshita, S. et al., "Preparation of N–benzyl (dioxothiazolidyl)benzamides and Their Use as Oral Antidiabetics and Hypothemic Agents," Database Caplus 'Online! Chemical Abstracts Service, 1997, Columbus, Ohio, Database accession No. 128:13261, abstract No. XP002181181.

Fujita, T. et al. "Preparation and Formation of Thiazolldinediones as Pharmaceuticals," Caplus 'Online! Chemical Abstracts Service, 1997, Columbus, Ohio, Database accession No. 127:161819, abstract No. XP002181182.

Crespi, C.L., et al., "Microlitter Plate Assays for Inhibition of Human, Drug–Metabolizing Cytochromes P450," *Anal. Biochem.* (1997) 248:188–190, Pub: Academic Press.

Crespi, C.L., "Higher–throughput screening with human cytochromes P450," *Curr. Op. Drug Discov. Dev.* (1999) 2:15–19.

Crespi, C.L., et al., "Novel High throughput fluorescent cytochrome P450 assays," *Toxicol. Sci.* 48, abstr. No. 323 (1999).

Favreau, L.V., et al., "Improved Reality of the Rapid Microlitter Plate Assay Using Recombinant Enzyme in Predicting CYP2D6 Inhibition in Human Liver Microsomes," *Drug Metab. & Dispos.* (1999) 27(4):436–439, Pub: The American Society for Pharmacology & Experimental Therapeutics.

Houston, J.B., "Utility of in vitro drug metabolism data in predicting in vivo metabolic clearance," *Biochem. Pharmacol.* (1994) 47(9):1469–79.

Irvine, J.D., et al., "MDCK (Madin–Darby Canine Kidney) Cells: A Tool for Membrane Permeability Screening," *J. Pharm. Sci.* (1999) 88(1):28–33, Pub: American Chemical Society Society and American Pharmacological Society.

Korzekwa, K.R., et al., "Evaluation of Atypical Cytochrome P450 Kinetics With Two–Substrate Models: Evidence That Multiple Substrates Can Simultaneously Bind to Cytochrome P450 Active Sites," *Biochemistry* (1998) 37:4137–47.

Kostrubsky, V.E., et al., "Effect of taxol on cytochrome P450 3A and acetaminophen toxicity in cultured rat hepatocytes: Comparison to dexamethasone," *Toxicol. Appl. Pharmacol.* (1997) 142:79–86.

Stewart, B.H., et al., "Comparison of intestinal permeabilities determined in multiple in vitro and in situ models: relationship to absorption in humans," *Pharm. Res.* (1996) 12:693–99.

Swanson, H.I., "The AH–receptor, genetics, structure and function," *Pharmacogenetics* (1993) 3:213–30.

Tiller, P.R., et al., "Immobilized human serum albumin: Liquid chromatography/mass spectrometry as a method of determining drug–protein binding," *Rapid. comm. Mass spectrom.* (1995) 9:261–3.

Database CAPLUS 'Online! Chemical Abstracts Service,' Columbus, Ohio, USA; Database Accession No. 127:248106, XP002222346, Torii Pharmaceutical Co., Ltd., Japan, 1997.

Database CHEMCATS, AsInEx Compound Collection, Moscow, Russia; Accession No. 2001:694380, May 10, 2001; XP002222347.

Database CHEMCATS, Pharma Library Collection, Nanosyn Combinational Synthesis, Inc., Mountain View, CA, USA; Accession No. 2001:54111, May 14, 2001; XP002222348.

Database CHEMCATS, Ambinter Exploratory Library, Paris, France; Accession No. 2002:1116502, Jan. 21, 2002; XP002222349.

Cantello, B., et al., "[[ω–(Heterocyclylamino)alkoxy]benzyl]–2,4–thiazolinediones as Potent Antihyperglycemic Agents," *J. Med. Chem.* (1994), 37:3977–3985; XP–001094112; American Chemical Society.

Chen, L., et al., "Focused Library Appraoch for Identification of N–Acylphenylalanines as VCAM/VLA–4 Antagonists", *Bioorg. Med. Chem. Lett.* (2002), 12:1679–1682; XP–002230539; Elsevier Science Ltd.

Database Crossfire Beilstein; Beilstein Registry No.: 6526484; Beilstein Institut zur Foerderung der Chemischen Wissenschaften; XP–002230540; Frankfurt am Main, DE, 1994.

Haigh, D., et al., "Non–thiazolidinedione Antihyperglycaemic Agents. Part 3: The effects of stereochemistry on the potency of α–Methoxy–β–phenypropanoic Acids", *Bioorg. Med. Chem.* (1999), 7:821–830; XP–000995637; Elsevier Science Limited.

Henke, B., et al., "N–(2–Benzoylphenyl)–L–tyrosine PPAR$_\gamma$ Agonists. 1. Discovery of a Novel Series of Potent Antihyperglycemic and Antihyperlipidermic Agents", *J. Med. Chem.* (1998), 41:5020–5036; XP–000864731; American Chemical Society.

*Patent Abstracts of Japan* (2001), vol. 2000, No. 19.

Rahbar, S., et al., "Novel Inhibitors of Advanced Glycation Endproducts", *Biochem. Biophys. Reas. Comm* (1999), 262:651–656; XP–000946146; Academic Press.

i) $NaNO_2$ and HCl in water. (ii) methyl acrylate and cuprous oxide.
(iii) Thiourea/NaOAc. (iv) HCl in water. (v) $BBr_3$ in methylene chloride.

(i) DCC/DMAP in methylene chloride

▭—C(=O)OH and ▭—OH = X as described in Table I $R_1$ as in Tables II to V
$R_2$ and $R_3$ = H or $CH_3$ (i) $Et_3N/Ac_2O/DMAP$, then $H_2O/KOH$ pH9 0. (ii) 6N HCl, then MeOH/$SOCl_2$. (iii) $R_1COCl/Et_3N$.
(iv) $H_2SO_4$ (cat) in EtOAc. (v) LiOH in MeOH/$H_2O$. (vi) LAH/THF. (vii) $B_2H_6$, or $SOCl_2$ then $NaBH_4$.

R1 as in Tables II to V (i) NaNO$_2$/AcOH. (ii) Zn powder (iii) R$_1$COCl/Et$_3$N. (iv) H$_2$SO$_4$ (cat) in EtOAc. (v) LAH/THF. (vi) LiOH in MeOH/H$_2$O.

R1 as in Tables II to V (i) NaNO₂/AcOH. (ii) Zn powder. (iii) R₁COCl/Et₃N. (iv) H₂SO₄ (cat) in EtOAc. (v) NaBH₄.
(vi) CH₃MgBr in THF.

$R_1$ as in Tables II to V
$R_2$ and $R_3$ = H or $CH_3$ (i) Lawesson's reagent (ii) Toluene/Δ (iii) LAH/THF. (iv) LiOH in MeOH/$H_2O$.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) Et₃N/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) Et$_3$N/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) $Et_3N$/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl, (R)-6-Hydroxy-2,5,7,8-tetramethylchromanyl-2-methyl, (S)-6-Hydroxy-2,5,7,8-tetramethylchromanyl-2-methyl (i) Et$_3$N/THF. (ii) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride. (ii) LiOH in MeOH/H2O.
(iii) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride. (iii) LiOH in MeOH/H2O.
(iii) DCC/DMAP in methylene chloride.

P and Q = H or double bond
Y = (R)-6-Hydroxy-2,5,7,8-tetramethylchroman-2-carbonyl, (S)-6-Hydroxy-2,5,7,8-tetramethylchroman-2-carbonyl, (R)-2,3-Dihydro-2,2,5,6,7-pentamethyl-5-hydroxy-benzofuran-3-carbonyl, (R)-2,3-Dihydro-2,2,5,6,7-pentamethyl-5-hydroxy-benzofur 3-carbonyl.

(i) DCC/DMAP in methylene chloride.

(i) EDC in methylene chloride. (ii) SOCl$_2$. (iii) H$_2$/Pd/C. (iv) DCC/DMAP/1 in methylene cl (i) benzoic acid/piperidine in dichloromethane (ii) Mg powder in ethanol (iii) $BBr_3$ in dichloromethane (i) benzoic acid/piperidine in dichloromethane (ii) Mg turnings in methanol (iii) LiOH in methanol/water or 6N HCL at reflux temperature (i) NaNO₂ and HCl in water (ii) methyl acrylate and cuprous oxide (iii) Thiourea/NaOAc (iv) HCl in water (v) BBr₃ in methylene chloride (i) acetone/CHCl₃/NaOH (i) 2-benzoylcyclohexanone, 10% Pd/C (i) 2-benzoylcyclohexanecarbonyl chloride, 10% Pd/C (i) Et₃N/Ac₂O/DMAP, then H₂O/KOH pH9.0. (ii) 6N HCl, then McOH/SOCl₂. (iii) Benzoyl chlori Et₃N. (iv) H₂SO4 (cat) in EtOAc. (v) LiOH in McOH/H₂O. (vi) LAH/THF. (vii) B₂H₆, or SOCl₂ then NaBH₄

(i) NaNO$_2$/AcOH. (ii) Zn powder. (iii) Benzoyl chloride/Et$_3$N. (iv) H$_2$SO$_4$ (cat) in EtOAc.
(v) LAH/THF. (vi) LiOH in MeOH/H$_2$O.

(i) ethanol/reflux. (ii) LiOH. (iii) AlLiH₄.

MATERIALS AND METHODS FOR THE TREATMENT OF DIABETES, HYPERLIPIDEMIA, HYPERCHOLESTEROLEMIA, AND ATHEROSCLEROSIS

CROSS-REFERENCE TO RELATED APPLICATIONS

This application is a continuation-in-part of U.S. application Ser. No. 10/228,670, filed Aug. 26, 2002, which claims the benefit of U.S. Provisional Application No. 60/314,792, filed Aug. 24, 2001. This application is also a continuation-in-part of U.S. application Ser. No. 09/961,542, filed Sep. 21, 2001, now U.S. Pat. No. 6,768,008, which claims the benefit of U.S. Provisional Application No. 60/297,838, filed in Jun. 13, 2001 and U.S. Provisional Application No. 60/281,982, filed Apr. 6, 2001, said U.S. application Ser. No. 09/961,542 being a continuation-in-part of U.S. application Ser. No. 09/841,351, filed Apr. 24, 2001, now U.S. Pat. No. 6,680,387, which claims the benefit of U.S. Provisional Application No. 60/199,146, ,filed Apr. 24, 2000, and U.S. Provisional Application No. 60/281,982, filed Apr. 6. 2001. This application is also a continuation-in-part of U.S. application Ser. No. 09/961,538, filed Sep. 21, 2001, now U.S. Pat. No. 6,784,199. which claims the benefit of U.S. Provisional Application No. 60/314,792, filed Aug. 24, 2001 and U.S. Provisional Application No. 60/234,423, filed Sep. 21, 2000. The disclosures of each of the above-identified patent applications are hereby incorporated by reference in their entireties, including all figures, tables, and chemical structures.

BACKGROUND OF THE INVENTION

Diabetes is one of the most prevalent chronic disorders worldwide with significant personal and financial costs for patients and their families, as well as for society. Different types of diabetes exist with distinct etiologies and pathogeneses. For example, diabetes mellitus is a disorder of carbohydrate metabolism, characterized by hyperglycemia and glycosuria and resulting from inadequate production or utilization of insulin.

Noninsulin-dependent diabetes mellitus (NIDDM), often referred to as Type II diabetes, is a form of diabetes that occurs predominantly in adults who produce adequate levels of insulin but who have a defect in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver. It has been shown that for some people with diabetes a genetic predisposition results from a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

For people with Type II diabetes, insulin secretion is often enhanced, presumably to compensate for insulin resistance. Eventually, however, the B-cells fail to maintain sufficient insulin secretion to compensate for the insulin resistance. Mechanisms responsible for the B-cell failure have not been identified, but may be related to the chronic demands placed on the B-cells by peripheral insulin resistance and/or to the effects of hyperglycemia. The B-cell failure could also occur as an independent, inherent defect in "pre-diabetic" individuals.

NIDDM often develops from certain at risk populations. One such population is individuals with polycystic ovary syndrome (PCOS). PCOS is the most common endocrine disorder in women of reproductive age. This syndrome is characterized by hyperandrogenism and disordered gonadotropin secretion producing oligo- or anovulation. Recent prevalence estimates suggest that 5–10% of women between 18–44 years of age (about 5 million women, according to the 1990 census) have the full-blown syndrome of hyperandrogenism, chronic anovulation, and polycystic ovaries. Despite more than 50 years since its original description, the etiology of the syndrome remains unclear. The biochemical profile, ovarian morphology, and clinical features are non-specific; hence, the diagnosis remains one of exclusion of disorders, such as androgen-secreting tumors, Cushing's Syndrome, and late-onset congenital adrenal hyperplasia. PCOS is associated with profound insulin resistance resulting in substantial hyperinsulinemia. As a result of their insulin resistance, PCOS women are at increased risk to develop NIDDM.

NIDDM also develops from the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic B-cell responsiveness to glucose normally increases nearly 3-fold by late pregnancy, a response that serves to minimize the effect of insulin resistance on circulating glucose levels. Thus, pregnancy provides a major "stress-test" of the capacity for B-cells to compensate for insulin resistance.

Other populations thought to be at risk for developing NIDDM include persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions.

Failure to treat NIDDM can result in mortality due to cardiovascular disease and in other diabetic complications including retinopathy, nephropathy, and peripheral neuropathy. There is a substantial need for a method of treating at risk populations such as those with PCOS and GDM in order to prevent or delay the onset of NIDDM thereby bringing relief of symptoms, improving the quality of life, preventing acute and long-term complications, reducing mortality and treating accompanying disorders of the populations at risk for NIDDM.

For many years, treatment of NIDDM has involved a program aimed at lowering blood sugar with a combination of diet and exercise. Alternatively, treatment of NIDDM can involve oral hypoglycemic agents, such as sulfonylureas alone or in combination with insulin injections. Recently, alpha-glucosidase inhibitors, such as a carboys, have been shown to be effective in reducing the postprandial rise in blood glucose (Lefevre, et al., Drugs 1992; 44:29–38). In Europe and Canada another treatment used primarily in obese diabetics is metformin, a biguanide.

Compounds useful in the treatment of the various disorders discussed above, and methods of making the compounds, are known and some of these are disclosed in U.S. Pat. No. 5,223,522 issued Jun. 29, 1993;U.S. Pat. No. 5,132,317 issued Jul. 12, 1992; U.S. Pat. No. 5,120,754 issued Jun. 9, 1992; U.S. Pat. No. 5,061,717 issued Oct. 29, 1991; U.S. Pat. No. 4,897,405 issued Jan. 30, 1990; U.S. Pat. No. 4,873,255 issued Oct. 10, 1989; U.S. Pat. No. 4,687,777 issued Aug. 18, 1987; U.S. Pat. No. 4,572,912 issued Feb. 25, 1986; U.S. Pat. No. 4,287,200 issued Sep. 1, 1981; U.S. Pat. No. 5,002,953, issued Mar. 26, 1991; U.S. Pat. Nos. 4,340,605; 4,438,141; 4,444,779; 4,461,902; 4,703,052; 4,725,610; 4,897,393; 4,918,091; 4,948,900; 5,194,443; 5,232,925; and 5,260,445; WO 91/07107; WO 92/02520; WO 94/01433; WO 89/08651; and JP Kokai 69383/92. The compounds disclosed in these issued patents and applications are useful as therapeutic agents for the treatment of diabetes, hyperglycemia, hypercholesterolemia, and hyperlipidemia. The teachings of these issued patents are incorporated herein by reference in their entireties.

Drug toxicity is an important consideration in the treatment of humans and animals. Toxic side effects resulting from the administration of drugs include a variety of conditions that range from low-grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

One of the drugs used to treat Type II diabetes is troglitazone. The major side effects of troglitazone are nausea, peripheral edema, and abnormal liver function. Other reported adverse events include dyspnea, headache, thirst, gastrointestinal distress, insomnia, dizziness, incoordination, confusion, fatigue, pruritus, rash, alterations in blood cell counts, changes in serum lipids, acute renal insufficiency, and dryness of the mouth. Additional symptoms that have been reported, for which the relationship to troglitazone is unknown, include palpitations, sensations of hot and cold, swelling of body parts, skin eruption, stroke, and hyperglycemia. Accordingly, forms of glitazones which have fewer, or no, adverse effects (i.e., less toxicity) are desirable.

The principal difference between the compounds of the present invention and related compounds is the presence of a carboxyl group, either OOC— or COO—, directly attached to the 4-position of the phenyl ring. In the literature, thiazolidinediones having similar therapeutic properties have an ether function at the 4-position of the phenyl ring instead of a carboxyl group.

The presence of the carboxyl group has significant consequences for the biological behavior of these new compounds. The present compounds are primarily metabolized by hydrolytic enzymatic systems, whereas compounds having an ether function are metabolized only by oxidative enzymes. Hydrolytic enzymatic systems are ubiquitous, non-oxidative, not easily saturable, and non-inducible, and, therefore, reliable. By contrast, oxidative systems are mediated by the P-450 isozymes. These systems are localized, mainly, in the liver, saturable and inducible (even at low concentrations of therapeutic compounds) and therefore are highly unreliable.

The compounds of the subject invention do not rely on saturable hepatic systems for their metabolism and elimination, whereas the prior art compounds exert a heavy bio-burden on hepatic functions, especially in the presence of other drugs that rely on similar enzymes for detoxification. Thus, the present compounds have a much more desirable toxicity profile than prior art compounds, especially when considering liver toxicity and potentially fatal drug-drug interactions.

Upon metabolism by plasma and tissue esterases, the compounds of this invention are hydrolyzed into 2 types of molecules: 1) an alcohol or a phenol, and 2) a carboxylic acid. Therefore, any compound that yields compound 1, compound 2, compound 3, or compound 4, as defined in Table I, as a primary metabolite falls under the definition of this invention. This concept is illustrated in FIG. 1, taking compound 9 (of Table I) and compound 145 (of Table X) as specific examples of compounds giving 1 and 3, respectively, upon non-oxidative metabolism by esterases.

BRIEF SUMMARY OF THE INVENTION

The subject invention provides materials and methods for the safe and effective treatment of diabetes, hyperlipidemia, hypercholesterolemia, and atherosclerosis. In a preferred embodiment, the subject invention provides therapeutic compounds for the treatment of diabetes. The compounds of the subject invention can be used to treat at-risk populations, such as those with PCOS and GDM, in order to prevent or delay the onset of NIDDM thereby bringing relief of symptoms, improving the quality of life, preventing acute and long-term complications, reducing mortality and treating accompanying disorders.

Advantageously, the subject invention provides compounds that are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of treatment for Type II diabetes, hyperlipidemia, hypercholesterolemia, and atherosclerosis.

In a further embodiment, the subject invention pertains to the breakdown products that are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

BRIEF DESCRIPTION OF THE TABLES

Figure 1:
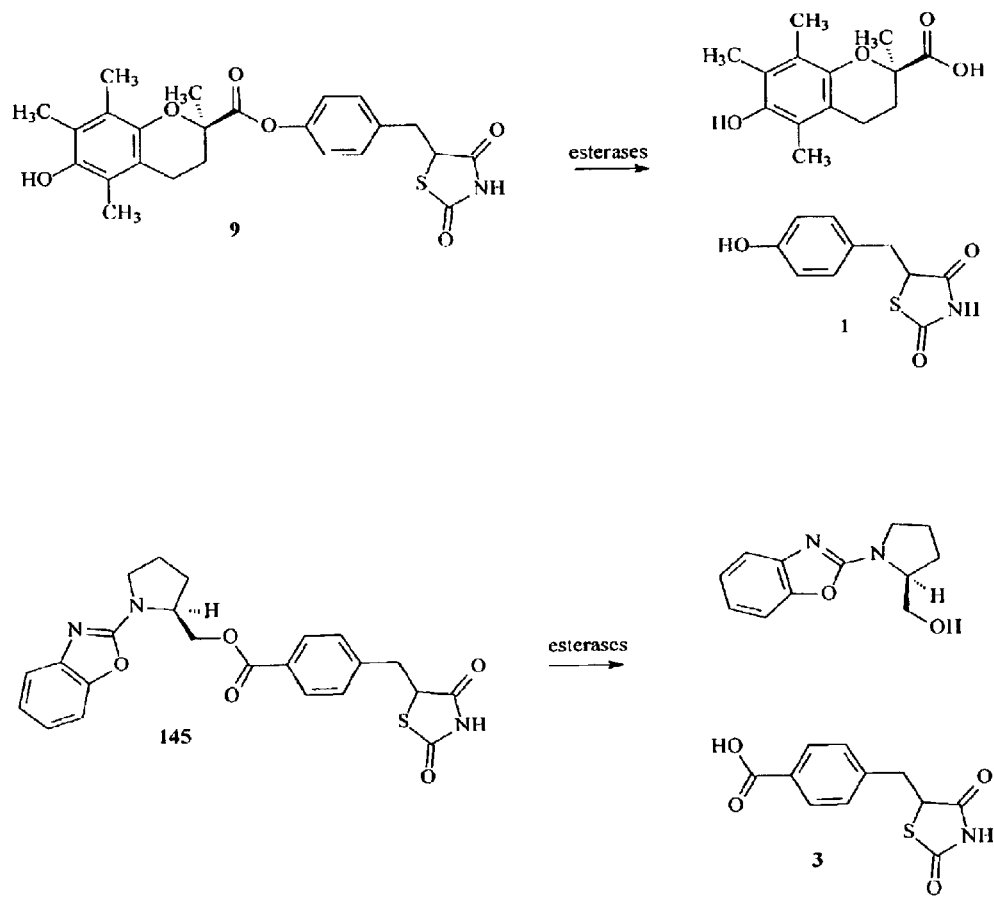
FIG. 1 depicts exemplary metabolic breakdown products resulting from the actions of esterases on compounds of the invention.

Tables I–XXII depict exemplary compounds according to the invention. The term "db" indicates a double bond between P and Q.

Table XXIII illustrates the effects of exemplary compounds on serum glucose and insulin levels in NIDDM mice.

DETAILED DISCLOSURE OF THE INVENTION

The subject invention provides materials and methods for the treatment of non-insulin dependent diabetes mellitus (NIDDM), hyperlipidemia, hypercholesterolemia, and atherosclerosis. Advantageously, the therapeutic compounds of the subject invention are stable in storage but have a shorter half-life in the physiological environment than other drugs which are available for treatment of diabetes; therefore, the compounds of the subject invention can be used with a lower incidence of side effects and toxicity, especially in patients having elevated liver function or compromised liver function.

In a preferred embodiment of the subject invention, therapeutic compounds are provided which are useful in the treatment of diabetes, hyperlipidemia, hypercholesterolemia, and atherosclerosis and which contain an ester group which is acted upon by esterases thereby breaking down the compound and facilitating its efficient removal from the treated individual. In a preferred embodiment the therapeutic compounds are metabolized by the Phase I drug detoxification system and are exemplified by the compounds of Formulae I–IX.

The compounds of Formula IA can be generally described as 5-benzyl- or 5-benzylidene-thiazolidine-2,4-dione compounds having a carboxyl group directly attached to the para-position of the phenyl ring. These compounds represent a new class of chemical compounds having therapeutic properties for the treatment of type-II diabetes mellitus, atherosclerosis, hypercholesterolemia, and hyperlipidemia.

FORMULA IA

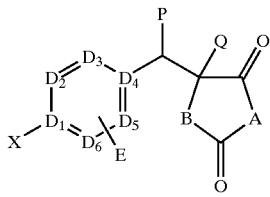

For compounds of Formula IA:

A and B may be the same or different and are $CH_2$, CO, N, NO, NH, $SO_{0-2}$, or O;

$D_1$–$D_6$ can be the same or different and are CH, N, S, or O;

E can be a substituent attached to one or more of the atoms located at $D_1$–$D_6$;

P and Q can be a double bond; or

P, Q, and E can be the same or different and are a moiety selected from the group consisting of H, $C_{1-10}$ alkyl, substituted alkyl groups, substituted or unsubstituted carboxylic acids, substituted or unsubstituted carboxylic esters, halogen, carboxyl, hydroxyl, phosphate, phosphonate, aryl, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heterocycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine or thiadiazoline.

Substituted carboxylic acids, substituted carboxylic esters, and substituted alkyl groups can be substituted at any available position with a moiety selected from the group consisting of $C_{1-10}$ alkyl, halogen, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

X is —OH, —COOH, or a substituted carboxylic group having the carboxyl moiety OOC— or COO— directly attached to the phenyl ring of the compound of Formula I. The carboxylic acid group can be substituted with a moiety selected from the group consisting of alkyloxycarbonyl, alkylcarbonyloxy, aryloxycarbonyl, arylcarbonyloxy, heteroalkyloxycarbonyl, heteroalkylcarbonyloxy, heteroaryl-oxycarbonyl, and heteroarylcarbonyloxy each of which is, optionally, substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. In other embodiments, the substituted carboxylic group can be substituted with a moiety selected from the group consisting of $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

In specific embodiments, X can be hydroxyl, hydroxycarbonyl, 1-methyl-1-cyclohexylcarbonyloxy, 1-methyl-1-cyclohexylmethoxycarbonyl, 5-ethyl-2-pyridyl-acetoxy, 5-ethyl-2-pyridylmeth-oxy-carbonyl, (R)-6-hydroxy-2,5,7,8-tetramethylchroman-2-carboxy, (S)-6-hydroxy-2,5,7,8-tetramethylchroman-2-carboxy, (R)-6-hydroxy-2,5,7,8-tetra-methylchroman-2-ylmethoxy-carbonyl, (S)-6-hydroxy-2,5,7,8-tetramethylchroman-2-ylmethoxycarbonyl, (R)-5-hydroxy-2,2,4,6,7-pentamethyl-2,3-dihydrobenzofuran-3-carboxy, (S)-5-hydroxy-2,2,4,6,7-pentamethyl-2,3-dihydrobenzofuran-3-carboxy, (R)-5-hydroxy-2,2,4,6,7-penta-methyl-2,3-dihydrobenzofuran-3-methoxycarbonyl, (S)-5-hydroxy-2,2,4,6,7-pentamethyl-2,3-dihydrobenzofuran-3-methoxycarbonyl, 2-hydroxybenzoyloxy, or 2,4-dihydroxybenzoyloxy.

In other embodiments, X can be

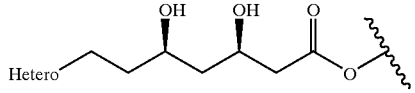

wherein Hetero is an aromatic, cyclic, or alicyclic moiety that can contain heteroatoms. In certain specific embodiments, Hetero is an aromatic, cyclic, or alicyclic moiety that contains heteroatoms that are generally part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin.

Alternatively, X can be

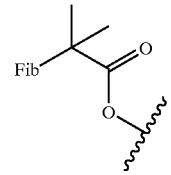

wherein Fib is an aromatic, cyclic, or alicyclic moiety that can contain heteroatoms. In certain specific embodiments, Fib moieties are part of the fibrate-family of lipid lowering agents. Preferred examples include, but are not limited to 4-(4-chlorobenzoyl)phenoxy, a component of fenofibric acid, 4-chlorophenoxy, a component of clofibric acid, and 3-(2,5-xylyloxy)-1-propyl, a component of gemfibrozil.

Alternatively, X can be

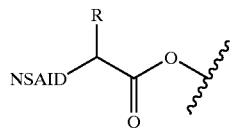

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl.

In another embodiment, X can be

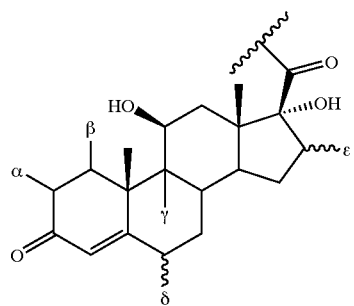

where α and β are hydrogen or α and β form a bond, and where γ, δ, and ε, are independently hydrogen, hydroxy, fluoro, chloro, or methyl.

Alternatively, X can be

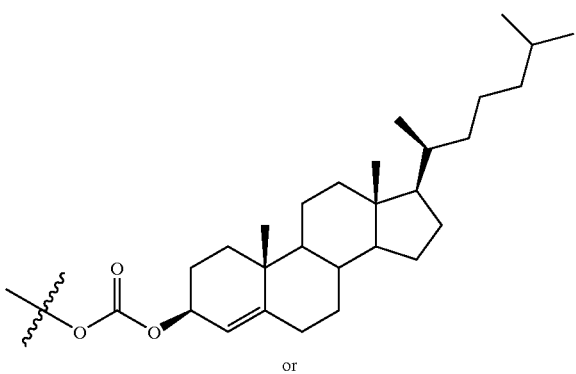

X can also be of the general formula

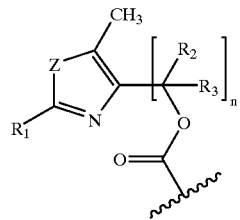

In such embodiments, n is 0 or 1, $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl.

Other embodiments provide compounds wherein X is

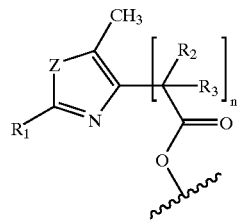

in which n is 0 or 1, $R_2$ and $R_3$ are independently hydrogen or methyl; Z is N, O, or S; and $R_1$ is aryl or heteroaryl, alkyl or heteroalkyl. Preferred non-limiting examples include compounds where R1 is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl.

In other embodiments, X is a 1-substituted (R)-pyrrolidine-2-methoxycarbonyl, (S)-pyrrolidine-2-methoxycarbonyl, (R)-pyrrolidine-2-carboxy, or (S)-pyrrolidine-2-carboxy, having the following formulas

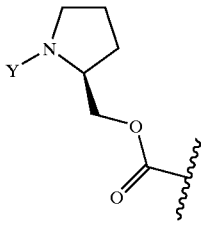 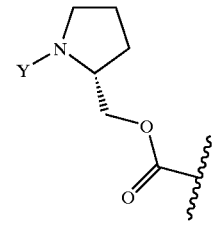

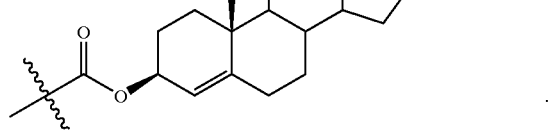

in which Y is aryl or heteroaryl, alkyl or heteroalkyl. Preferred non-limiting examples include compounds where Y is (R)-6-hydroxy-2,5,7,8-tetramethylchroman-2-carboxy, (S)-6-hydroxy-2,5,7,8-tetramethylchroman-2-carboxy, (R)-6-hydroxy-2,5,7,8-tetramethylchroman-2-ylmeth-oxycarbonyl, (S)-6-hydroxy-2,5,7,8-tetramethylchroman-2-ylmeth-oxycarbonyl, (R)-5-hydroxy-2,2,4,6,7-pentamethyl- 2,3-dihydrobenzofuran-3-carboxy, (S)-5-hydroxy-2,2,4,6,7-pentamethyl-2,3-dihydrobenzofuran-3-carboxy, (R)-5-hydroxy-2,2,4,6,7-pentamethyl-2,3-dihydrobenzofuran-3-methoxycarbonyl, (S)-5-hydroxy-2,2,4,6,7-pentamethyl-2,3-dihydrobenzofuran-3-methoxycarbonyl, 5-chloro-2-pyridyl, 5-methyl-2-pyridyl, 3-chloro-2-pyridyl, 4-methyl-2-pyridyl, 2-pyridyl, 2-benzoxazolyl, 2-benzothiazolyl, 5-amino-2-pyridyl, 5-nitro-2-pyridyl, 2-pyrazinyl, 4-phenyl-2-oxazolinyl, 5-methyl-2-thiazolinyl, 4,5-dimethyl-2-oxazolinyl, 4,5-dimethyl-2-thiazolinyl, 5-phenyl-2-thiazolinyl, 2-thiazolinyl, 4-methyl-5-phenyl-2-thiazolinyl, 5-methyl-4-phenyl-2-thiazolinyl, 2-piperidinyl, 4-phenyl-2-piperidinyl, 6-methyl-2-pyridinyl, 6-methoxy-2-pyridinyl, 2-hydroxybenzoyl, or 2,4-dihydroxybenzoyl.

Alternatively X is an N-substituted 2-methylaminoethoxycarbonyl or a N-substituted 2-methylaminoacetoxy, having the following formulas:

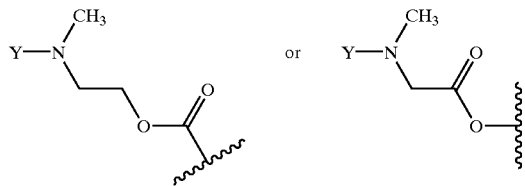

in which Y is aryl or heteroaryl, alkyl or heteroalkyl. Preferred non-limiting examples include compounds where Y is (R)-6-hydroxy-2,5,7,8-tetramethylchroman-2-carboxy, (S)-6-hydroxy-2,5,7,8-tetramethylchroman-2-carboxy, (R)-6-hydroxy-2,5,7,8-tetramethylchroman-2-ylmethoxycarbonyl, (S)-6-hydroxy-2,5,7,8-tetramethylchroman-2-ylmethoxycarbonyl, (R)-5-hydroxy-2,2,4,6,7-pentamethyl-2,3-dihydrobenzofuran-3-carboxy, (S)-5-hydroxy-2,2,4,6,7-pentamethyl-2,3-dihydrobenzofuran-3-carboxy, (R)-5-hydroxy-2,2,4,6,7-pentamethyl-2,3-dihydrobenzofuran-3-methoxycarbonyl, (S)-5-hydroxy-2,2,4,6,7-pentamethyl-2,3-dihydrobenzofuran-3-methoxycarbonyl, 5-chloro-2-pyridyl, 5-methyl-2-pyridyl, 3-chloro-2-pyridyl, 4-methyl-2-pyridyl, 2-pyridyl, 2-benzoxazolyl, 2-benzothiazolyl, 5-amino-2-pyridyl, 5-nitro-2-pyridyl, 2-pyrazinyl, 4-phenyl-2-oxazolinyl, 5-methyl-2-thiazolinyl, 4,5-dimethyl-2-oxazolinyl, 4,5-dimethyl-2-thiazolinyl, 5-phenyl-2-thiazolinyl, 2-thiazolinyl, 4-methyl-5-phenyl-2-thiazolinyl, 5-methyl-4-phenyl-2-thiazolinyl, 2-piperidinyl, 4-phenyl-2-piperidinyl, 6-methyl-2-pyridinyl, 6-methoxy-2-pyridinyl, 2-hydroxybenzoyl, or 2,4-dihydroxybenzoyl.

X can also be a 1-substituted (R)-pyrrolidine-2-methoxycarbonyl, (S)-pyrrolidine-2-methoxycarbonyl, (R)-pyrrolidine-2-carboxy, or (S)-pyrrolidine-2-carboxy, having the following formulas:

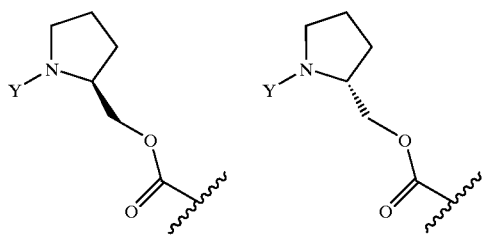

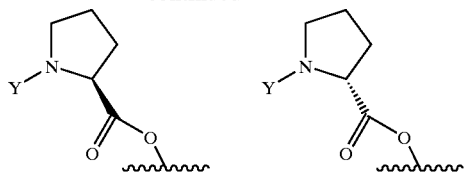

wherein Y is

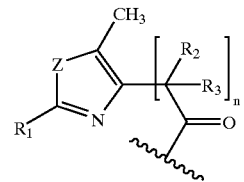

n is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, or 2-pyrazinyl; or Y is

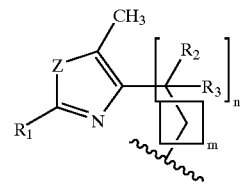

n is 0 or 1; m is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, or 2-pyrazinyl; or Y is

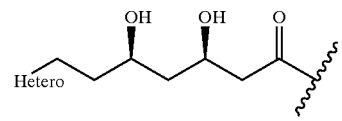

wherein Hetero is an aromatic, cyclic, or alicyclic moiety that usually contains heteroatoms. In certain specific embodiments, these moieties are part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin; or Y is

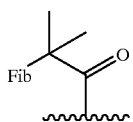

wherein Fib is an aromatic, cyclic, or alicyclic moiety that contains heteroatoms. In some embodiments, these moieties are part of the fibrate-family of lipid lowering agents. Preferred examples include, but are not limited to 4-(4-chlorobenzoyl)phenoxy, a component of fenofibric acid, 4-chlorophenoxy, a component of clofibric acid, and 3-(2,5-xyloxy)-1-propyl, a component of gemfibrozil; or
Y is

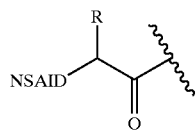

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl or
Y can be

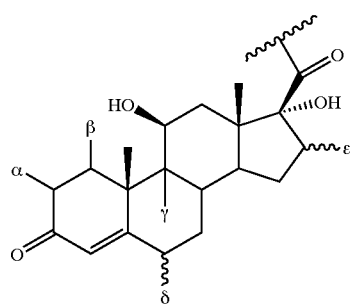

where α and β are hydrogen or α and β form a bond, and where γ, δ, and ε, are independently hydrogen, hydroxy, fluoro, chloro, or methyl; or
Y can be

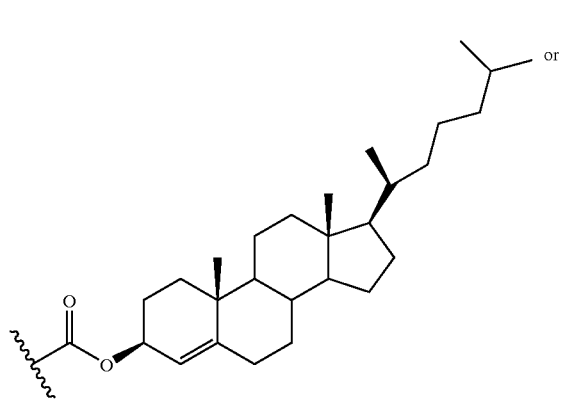

or

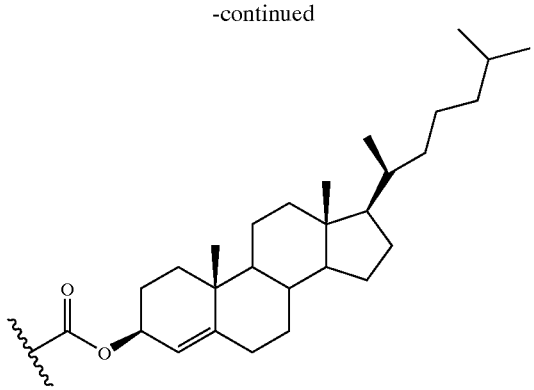

Alternatively X can be an N-substituted 2-methylaminoethoxycarbonyl or an N-substituted 2-methylaminoacetoxy, having the following formulas:

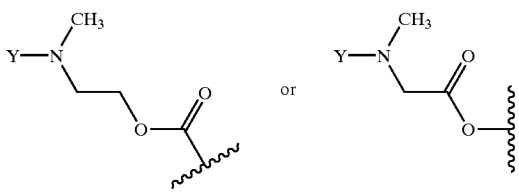

wherein Y is

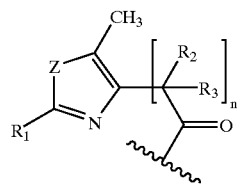

n is 0 or 1; $R_2$ and $R_3$ are independently hydrogen or methyl; Z is N, O, or S; and $R_1$ is aryl, heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, or 2-pyrazinyl, 2-hydroxybenzoyl, or 2,4-dihydroxybenzoyl; or
Y is

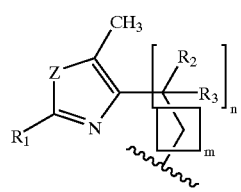

n is 0 or 1; m is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl; or Y is

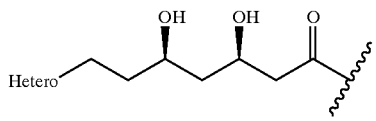

wherein Hetero is an aromatic, cyclic, or alicyclic moiety that contains heteroatoms. In certain specific embodiments, these moieties are part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin; or Y is

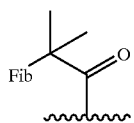

wherein Fib is an aromatic, cyclic, or alicyclic moiety that contains heteroatoms. In some embodiments, these moieties are part of the fibrate-family of lipid lowering agents. Preferred examples include, but are not limited to 4-(4-chlorobenzoyl)phenoxy, a component of fenofibric acid, 4-chlorophenoxy, a component of clofibric acid, and 3-(2,5-xylyloxy)-1-propyl, a component of gemfibrozil; or Y is

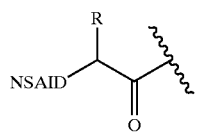

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl; or Y can be

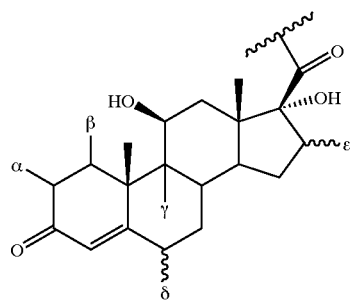

where $\alpha$ and $\beta$ are hydrogen or $\alpha$ and $\beta$ form a bond, and where $\gamma$, $\delta$, and $\epsilon$, are independently hydrogen, hydroxy, fluoro, chloro, or methyl; or Y can be

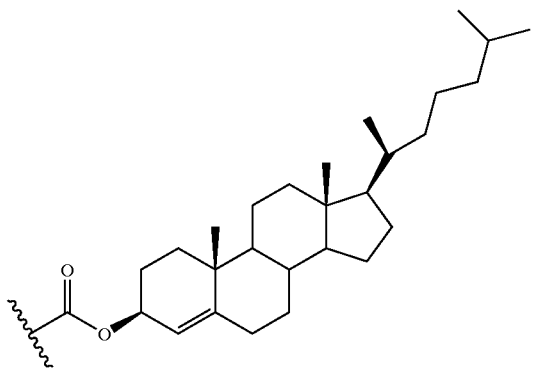

Other embodiments provide compounds wherein X is

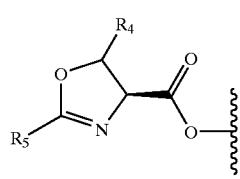

$R_4$ is hydrogen or methyl, and where $R_5$ is aryl or heteroaryl, alkyl or heteroalkyl. Preferred non-limiting examples include compounds where $R_5$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, (R)-6-hydroxy-2,5,7,8-tetramethyl-2-chromanyl, (S)-6-hydroxy-2,5,7,8-tetramethyl-2-chromanyl, (R)-5-hydroxy-2,2,4,6,7-pentamethyl-2,3-dihydro-3-benzofuranyl, or (S)-5-hydroxy-2,2,4,6,7-pentamethyl-2,3-dihydro-3-benzo-furanyl.

X can also be

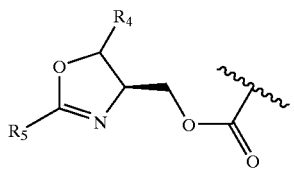

wherein R4 is hydrogen or methyl, and where R5 is aryl or heteroaryl, alkyl or heteroalkyl. Preferred non-limiting examples include compounds where R5 is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, (R)-6-hydroxy-2,5,7,8-tetramethyl-2-chromanyl, (S)-6-hydroxy-2,5,7,8-tetramethyl-2-chromanyl, (R)-5-hydroxy-2,2,4,6,7-pentamethyl-2,3-dihydro-3-benzofuranyl, or (S)-5-hydroxy-2,2,4,6,7-pentamethyl-2,3-dihydro-3-benzofuranyl.

In one embodiment, A is NH; B is sulfur (S); P and Q are a double bond or hydrogen (H); E is hydrogen (H) and is attached to each of $D_1$ through $D_6$; $D_1$ through $D_6$ are carbon (C); and X can be any of the structures provided supra.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

Analogs or derivatives of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

The subject invention further provides methods of treating disorders, such as diabetes, atherosclerosis, hypercholesterolemia, and hyperlipidemia, comprising the administration of a therapeutically effective amount of esterified thiazolidinedione analogs to an individual in need of treatment. Thiazolidinedione based compounds include troglitazone (for example, REZULIN), pioglitazone, and rosiglitazone. Accordingly, the subject invention provides esterified thiazolidinedione analogs and pharmaceutical compositions of these esterified compounds. The compounds and compositions according to the invention can also be administered in conjunction with other therapeutic compounds, therapeutic regimens, compositions, and agents suitable for the treatment of disorders, such as diabetes, atherosclerosis, hypercholesterolemia, and hyperlipidemia. Thus, the invention includes combination therapies wherein the compounds and compositions of the invention are used in conjunction with other therapeutic agents for the treatment of disorders, such as diabetes, atherosclerosis, hypercholesterolemia, and hyperlipidemia.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, 54$^{th}$ Ed., Medical Economics Company, Montvale, N.J., 2000).

The compounds of the subject invention can be formulated according to known methods for preparing pharmaceutically useful compositions. Formulations are described in detail in a number of sources that are well known and readily available to those skilled in the art. For example, *Remington's Pharmaceutical Science* by E. W. Martin describes formulations that can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds of the invention and one or more non-toxic, pharmaceutically acceptable carriers or diluents. Examples of such carriers for use in the invention include ethanol, dimethyl sulfoxide, glycerol, silica, alumina, starch, and equivalent carriers and diluents. Additional therapeutic agents suitable for the treatment of disorders such as diabetes, atherosclerosis, hypercholesterolemia, and hyperlipidemia can also be incorporated into pharmaceutical agents according to the invention.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The subject invention also provides therapeutically useful and effective compounds and compositions for the treatment of diabetes and a variety of related disorders, such as hyperlipidemia, and atherosclerosis. Various classes of compounds, useful for the treatment of diabetes and related disorders, that can be modified according to the concepts outlined herein include compounds such as the glitazones, thiazolidinediones, and isoxazolidinediones The compounds of this invention have one or more of the following characteristics or properties:

1. Compounds of the invention are metabolized both by CYP450 and by a non-oxidative metabolic enzyme or system of enzymes;

2. Compounds of the invention have a short (up to four (4) hours) non-oxidative metabolic half-life;

3. Oral bioavailability of the compounds is consistent with oral administration using standard pharmaceutical oral formulations; however, the compounds, and compositions thereof, can also be administered using any delivery system that produces constant and controllable blood levels over time;

4. Compounds according to the invention contain a hydrolysable bond that can be cleaved non-oxidatively by hydrolytic enzymes;

5. Compounds of the invention can be made using standard techniques of small-scale and large-scale chemical synthesis;

6. The primary metabolite(s) of compound(s) of this invention result(s) from the non-oxidative metabolism of the compound(s);

7. The primary metabolite(s), regardless of the solubility properties of the parent drug, is, or are, soluble in water at physiological pH and have, as compared to the parent compound, a significantly reduced pharmacological activity;

8. The primary metabolite(s), regardless of the electrophysiological properties of the parent drug, has, or have, negligible inhibitory activity at the $IK_R$ (HERG) channel at normal therapeutic concentration of the parent drug in plasma (e.g., the concentration of the metabolite must be at least five times higher than the normal therapeutic concentration of the parent compound before activity at the $IK_R$ channel is observed);

9. Compounds of the invention, as well as the metabolites thereof, do not cause metabolic DDI when co-administered with other drugs;

10. Compounds of the invention, as well as metabolites thereof, do not elevate LFT values when administered alone.

In some embodiments, the subject invention provides compounds have any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds have any combination of five to 10 of the above-identified characteristics or properties. In a preferred embodiment the compounds of the invention have all ten characteristics or properties.

In various embodiments, the primary metabolite(s) of the inventive compounds, regardless of the electrophysiological properties of the parent drug, has, or have, negligible inhibitory activity at the $IK_R$ (HERG) channel at normal therapeutic concentrations of the drug in plasma. In other words, the concentration of the metabolite must be at least five times higher than the normal therapeutic concentration of the parent compound before activity at the $IK_R$ channel is observed. Preferably, the concentration of the metabolite must be at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs, derivatives, and salts of the exemplified compounds are within the scope of the subject invention. With a knowledge of the compounds of the subject invention skilled chemists can use known procedures to synthesize these compounds from available substrates. As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

The subject invention further provides novel drugs that are dosed via drug delivery systems that achieve slow release of the drug over an extended period of time. These delivery systems maintain constant drug levels in the target tissue or cells. Such drug delivery systems have been described, for example, in *Remington: The Science and Practice of Pharmacy*, 19$^{th}$ Ed., Mack Publishing Co., Easton, Pa., 1995, pp 1660–1675, which is hereby incorporated by reference in its entirety. Drug delivery systems can take the form of oral dosage forms, parenteral dosage forms, transdermal systems, and targeted delivery systems.

Oral sustained-release dosage forms are commonly based on systems in which the release rate of drug is determined by its diffusion through a water-insoluble polymer. There are basically two types of diffusion devices, namely reservoir devices, in which the drug core is surrounded by a polymeric membrane, and matrix devices, in which dissolved or dispersed drug is distributed uniformly in an inert, polymeric matrix. In actual practice, however, many diffusion devices also rely on some degree of dissolution in order to govern the release rate.

Dissolution systems are based on the fact that drugs with slow dissolution rates inherently produce sustained blood levels. Therefore, it is possible to prepare sustained-release formulations by decreasing the dissolution rate of highly water-soluble drugs. This can be carried out by preparing an appropriate salt or other derivative, by coating the drug with a slowly soluble material, or by incorporating it into a tablet with a slowly soluble carrier.

In actual practice, most of the dissolution systems fall into two categories: encapsulated dissolution systems and matrix dissolution systems. Encapsulated dissolution systems can be prepared either by coating particles or granules of drug with varying thicknesses of slowly soluble polymers or by micro-encapsulation, which can be accomplished by using phase separation, interfacial polymerization, heat fusion, or the solvent evaporation method. The coating materials may be selected from a wide variety of natural and synthetic polymers, depending on the drug to be coated and the release characteristics desired. Matrix dissolution devices are prepared by compressing the drug with a slowly soluble polymer carrier into a tablet form.

In osmotic pressure-controlled drug-delivery systems, osmotic pressure is utilized as the driving force to generate a constant release of drug. Additionally, ion-exchange resins can be used for controlling the rate of release of a drug, which is bound to the resin by prolonged contact of the resin with the drug solution. Drug release from this complex is dependent on the ionic environment within the gastrointestinal tract and the properties of the resin.

Parenteral sustained-release dosage forms most commonly include intramuscular injections, implants for subcutaneous tissues and various body cavities, and transdermal devices. Intramuscular injections can take the form of aqueous solutions of the drug and a thickening agent which increases the viscosity of the medium, resulting in decreased molecular diffusion and localization of the injected volume. In this manner, the absorptive area is reduced and the rate of drug release is controlled. Alternatively, drugs can be complexed either with small molecules such as caffeine or procaine or with macromolecules, e.g., biopolymers such as antibodies and proteins or synthetic polymers, such as methylcellulose or polyvinylpyrrolidone. In the latter case, these formulations frequently take on the form of aqueous suspensions. Drugs which are appreciably lipophilic can be formulated as oil solutions or oil suspensions in which the release rate of the drug is determined by partitioning of the drug into the surrounding aqueous medium. The duration of action obtained from oil suspensions is generally longer than that from oil solutions, because the suspended drug particles must first dissolve in the oil phase before partitioning into the aqueous medium. Water-oil (W/O) emulsions, in which water droplets containing the drug are dispersed uniformly within an external oil phase, can also be used for sustained release. Similar results can be obtained from O/W (reverse) and multiple emulsions.

Implantable devices based on biocompatible polymers allow for both a high degree of control of the duration of drug activity and precision of dosing. In these devices, drug release can be controlled either by diffusion or by activation. In diffusion-type implants, the drug is encapsulated within a compartment that is enclosed by a rate-limiting polymeric membrane. The drug reservoir may contain either drug particles or a dispersion (or a solution) of solid drug in a liquid or a solid-type dispersing medium. The polymeric membrane may be fabricated from a homogeneous or a heterogeneous non-porous polymeric material or a microporous or semi-permeable membrane. The encapsulation of the drug reservoir inside the polymeric membrane may be accomplished by molding, encapsulation, microencapsulation or other techniques. Alternatively, the drug reservoir is formed by the homogeneous dispersion of drug particles throughout a lipophilic or hydrophilic polymer matrix. The dispersion of the drug particles in the polymer matrix may be accomplished by blending the drug with a viscous liquid polymer or a semi-solid polymer at room temperature, followed by crosslinking of the polymer, or by mixing of the drug particles with a melted polymer at an elevated temperature. It can also be fabricated by dissolving the drug particles and/or the polymer in an organic solvent followed by mixing and evaporation of the solvent in a mold at an elevated temperature or under vacuum.

In microreservoir dissolution-controlled drug delivery, the drug reservoir, which is a suspension of drug particles in an aqueous solution of a water-miscible polymer, forms a homogeneous dispersion of a multitude of discrete, unleachable, microscopic drug reservoirs in a polymer matrix. The microdispersion may be generated by using a high-energy dispersing technique. Release of the drug from this type of drug delivery device follows either an interfacial partition or a matrix diffusion-controlled process.

In activation-type implants, the drug is released from the semi-permeable reservoir in solution form at a controlled rate under an osmotic pressure gradient. Implantable drug-delivery devices can also be activated by vapor pressure, magnetic forces, ultrasound, or hydrolysis.

Transdermal systems for the controlled systemic delivery of drugs are based on several technologies. In membrane-moderated systems, the drug reservoir is totally encapsulated in a shallow compartment molded from a drug-impermeable backing and a rate-controlling microporous or non-porous polymeric membrane through which the drug molecules are released. On the external surface of the membrane, a thin layer of drug-compatible, hypoallergenic adhesive polymer may be applied to achieve an intimate contact of the transdermal system with the skin. The rate of drug release from this type of delivery system can be tailored by varying the polymer composition, permeability coefficient or thickness of the rate-limiting membrane and adhesive.

In adhesive diffusion-controlled systems, the drug reservoir is formulated by directly dispersing the drug in an adhesive polymer and then spreading the medicated adhesive, by solvent casting, onto a flat sheet of drug-impermeable backing membrane to form a thin drug reservoir layer. On top of the drug-reservoir layer, layers of non-medicated, rate controlling adhesive polymer of constant thickness are applied to produce an adhesive diffusion-controlled drug-delivery system.

In matrix dispersion systems, the drug reservoir is formed by homogeneously dispersing the drug in a hydrophilic or lipophilic polymer matrix. The medicated polymer is then molded into a disc with a defined surface area and controlled thickness. The disc is then glued to an occlusive baseplate in a compartment fabricated from a drug-impermeable backing. The adhesive polymer is spread along the circumference to form a strip of adhesive rim around the medicated disc. In microreservoir systems, the drug reservoir is formed by first suspending the drug particles in an aqueous solution of a water-soluble polymer and then dispersing homogeneously, in a lipophilic polymer, by high-shear mechanical forces to form a large number of unleachable, microscopic spheres of drug reservoirs. This thermodynamically unstable system is stabilized by crosslinking the polymer in situ, which produces a medicated polymer disk with a constant surface area and a fixed thickness.

Targeted delivery systems include, but are not limited to, colloidal systems such as nanoparticles, microcapsules, nanocapsules, macromolecular complexes, polymeric beads, microspheres, and liposomes. Targeted delivery systems can also include resealed erythrocytes and other immunologically-based systems. The latter may include drug/antibody complexes, antibody-targeted enzymatically-activated prodrug systems, and drugs linked covalently to antibodies.

The invention also provides methods of producing these compounds.

It is another aspect of this invention to provide protocols by which these conditions can be tested. These protocols include in vitro and in vivo tests that have been designed to: 1) ensure that the novel compound is metabolized both by CYP450 and by hydrolytic enzymes; 2) that the non-oxidative half-life of the parent drug is no more than a certain value when compared to an internal standard (in preferred embodiments, less than about four hours); 3) that the primary metabolite of the parent drug is the result of non-oxidative metabolism; 4) that the primary metabolite of the parent drug (regardless of the solubility properties of the parent drug) is water soluble; 5) that the primary metabolite of the parent drug (regardless of the electrophysiological properties of the parent drug) has negligible inhibitory properties toward $IK_R$ channel at concentrations similar to therapeutic concentration of the parent drug; 6) that the novel compound (regardless of its properties) does not cause metabolic DDI when co-administered with other drugs; and 7) that the novel compound does not cause hepatic toxicity in primary human hepatocytes.

The subject invention provides materials and methods for the treatment of non-insulin dependent diabetes mellitus (NIDDM), hyperlipidemia, hypercholesterolemia, and atherosclerosis. Advantageously, the therapeutic compounds of the subject invention are stable in storage but have a shorter half-life in the physiological environment than other drugs which are available for treatment of diabetes; therefore, the compounds of the subject invention can be used with a lower incidence of side effects and toxicity, especially in patients having elevated liver function or compromised liver function.

In another embodiment of the subject invention, therapeutic compounds are provided which are useful in the treatment of diabetes, hyperlipidemia, hypercholesterolemia, and atherosclerosis and which contain an ester group which is acted upon by esterases thereby breaking down the compound and facilitating its efficient removal from the treated individual. In a preferred embodiment, the therapeutic compounds are metabolized by non-oxidative systems and are exemplified by the compound of Formula IB.

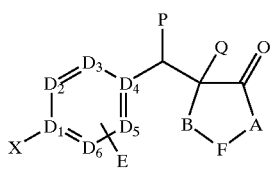

FORMULA IB

For compounds of Formula IB:

A, B, and F may be the same or different and are $CH_2$, CO, N, NO, NH, $SO_{0-2}$, O;

$D_1$–$D_6$ can be the same or different and are CH, N, S, or O;

E can be a substituent attached to one or more of the atoms located at $D_1$–$D_6$;

P and Q can be a double bond; or

P, Q, and E can be the same or different and are a moiety selected from the group consisting of H, $C_{1-10}$ alkyl, substituted alkyl groups, substituted or unsubstituted carboxylic acids, substituted or unsubstituted carboxylic esters, halogen, carboxyl, hydroxyl, phosphate, phosphonate, aryl, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but not limited to, morpholine, triazole, imidazole, pyrrolidine, piperidine, piperazine, pyrrole, dihydropyridine, aziridine, thiazolidine, thiazoline, thiadiazolidine or thiadiazoline.

Substituted carboxylic acids, substituted carboxylic esters, and substituted alkyl groups can be substituted at any available position with a moiety selected from the group consisting of $C_{1-10}$ alkyl, halogen, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

X is —OH, —COOH, or a substituted carboxylic group having the carboxyl moiety OOC— or COO— directly attached to the phenyl ring of the compound of Formula IB. The carboxylic acid group can be substituted with a moiety selected from the group consisting of alkyloxycarbonyl, alkylcarbonyloxy, aryloxycarbonyl, arylcarbonyloxy, heteroalkyloxycarbonyl, heteroalkylcarbonyloxy, heteroaryloxycarbonyl, and heteroarylcarbonyloxy each of which is, optionally, substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. In other embodiments, the substituted carboxylic group can be substituted with a moiety selected from the group consisting of $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

In one exemplary embodiment, compounds of the invention of FIG. IB have the following moieties: A is NH; F is O; B is C=O; P and Q are a double bond or H; $D_1$–$D_6$ are C (carbon), E is hydrogen; X is selected from the group consisting of: COOH, OH,

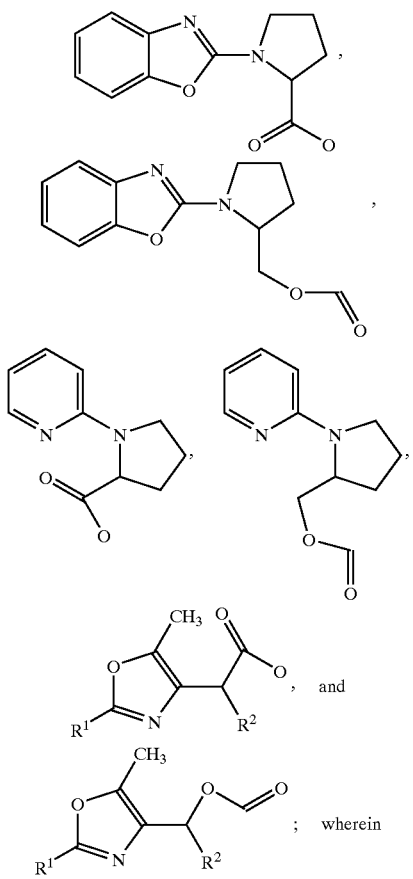

; wherein

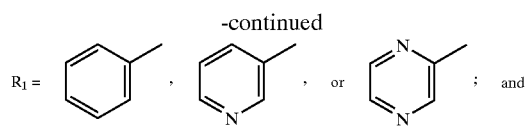

$R_1 =$ ... , ... , or ... ; and $R_2$ is $CH_3$ or H.

A further aspect of the subject invention provides procedures for synthesizing the therapeutic compounds of interest. An exemplary synthesis scheme is shown in FIGS. 22–28. In step 1, β-benzyl aspartate is suspended in triethylamine and acetic anhydride is added slowly at 0° C. with stirring. A catalytic amount of DMAP is then added under ice-cooling. The mixture is stirred overnight at room temperature and then ice-water is added. The pH is brought up to 9.0 with KOH solution and the product is extracted with ethyl acetate, dried, and concentrated.

In step 2, the acetamide group and the benzyl ester are cleaved with 6N HCl at reflux for 2 hours. The resulting amino acid is then isolated, dried, and then dissolved in a solution of thionyl chloride in methanol. After refluxing for 4 hours, the resulting methyl ester 3 is obtained.

In step 3, the amine compound 3 is suspended in dichloromethane and benzoyl chloride and triethylamine are added under ice-cooling. After stirring for 5 hours at room temperature, the product is washed with sodium bicarbonate solution, dried, and evaporated to give the benzamide 4.

In step 4, the oxazole 5 is formed by dissolving compound 4 in anhydrous ethyl acetate and treating with a catalytic amount of sulfuric acid for 3 hours at 90° C. The product is isolated as usual.

In step 5, the carboxylic acid 6 is obtained by treating 5 with 1 equivalent amount of lithium hydroxide in methanol/water.

Steps 6 and 7 can be combined in a one-pot reaction as follows: Acetylacetone 7 (1.5 mol) is dissolved in 450 ml of glacial acetic acid and the solution is cooled to 5° C. Sodium nitrite (1.5 mol in 150 ml of water) is added slowly so that the temperature stays between 5 and 7° C. Keep stirring for 4 hours at room temperature then add zinc powder (3 mol) portionwise under ice-cooling. Keep stirring at room temperature until the reaction is over and then collect the product 9 by filtration. Dry thoroughly.

Steps 8 and 9 proceed as described before. The amine 9 reacts with benzoyl chloride in dichloromethane in the presence of triethylamine in order to give the benzamide 10. The oxazole 11 is then obtained by cyclization with a catalytic amount of sulfuric acid at reflux in anhydrous ethyl acetate.

In step 10, treating the ketone 11 with 1 equivalent of methyl magnesium iodide in tetrahydrofuran at −40° C. gives the tertiary alcohol 12.

In step 11, the ketone 11 is reduced to the secondary alcohol 13 with sodium borohydride in methanol.

In step 12, p-methoxybenzaldehyde 14 reacts with dimethyl malonate in methanol with a catalytic amount of piperidinium benzoate, giving the benzylidene product 15.

In step 13, the benzylidene 15 is hydrolyzed in methanol/NaOH/water and then is acidified with dilute HCl to give the diacid. The diacid in turn reacts with thionyl chloride to give the acid chloride 16.

In step 14, the acid chloride 16 is dissolved in dichloromethane and triethylamine. Hydroxylamine hydrochloride is added under ice-cooling, giving the isoxazolidine 17.

In step 15, the methoxy-group in compound 17 is cleaved readily by boron tribromide, yielding the phenolic compound 18.

In step 16, the benzylidene compound 15 is reduced by magnesium powder in ethanol, giving dimethyl 4-methoxybenzylmalonate 19.

In steps 17, 18, and 19, compound 19 undergoes a similar sequence of reactions as in steps 13, 14, and 15, i.e., hydrolysis with NaOH/methanol/water and subsequent reaction with thionyl chloride to give the acid chloride 20. Compound 20 in turn reacts with hydroxylamine hydrochloride in dichloromethane and triethylamine to give 21. Finally, cleavage of the ether function with boron tribromide yields the phenolic compound 22.

In step 21, p-carboxybenzaldehyde 24 reacts with 2,4-isoxalolidinedione 25 (made from malonyl chloride and hydroxylamine, step 20) in THF in the presence of piperidinium benzoate to give the benzylidene 26.

In step 22, compound 26 is reduced with magnesium powder in ethanol to give 3-(4-carboxybenzyl)-isoxazolidine-2,4-dione 27.

In step 23, the carboxylic acid 26 reacts with the secondary alcohol 13 in dichloromethane in the presence of 1 equivalent amount of dicyclohexylcarbodiimide (DCC) and 4-dimethylaminopyridine (DMAP), giving the ester 28.

The same reaction takes place in step 24 between compounds 27 and 13, giving the ester 29.

Compounds 28 and 29 are among the group of preferred isoxazolidinedione analogs that have therapeutic properties against NIDDM and related diseases in mammals.

In step 25, the phenolic compound 18 reacts with the carboxylic acid 6 in dichloromethane in the presence of 1 equivalent amount of dicyclohexylcarbodiimide (DCC) and 4-dimethylaminopyridine (DMAP), giving the ester 30.

The same reaction takes place in step 26 between compounds 22 and 6, giving the ester 31.

Compounds 30 and 31 are among the group of preferred isoxazolidinedione analogs that have therapeutic properties against NIDDM and related diseases in mammals.

Figure 3:
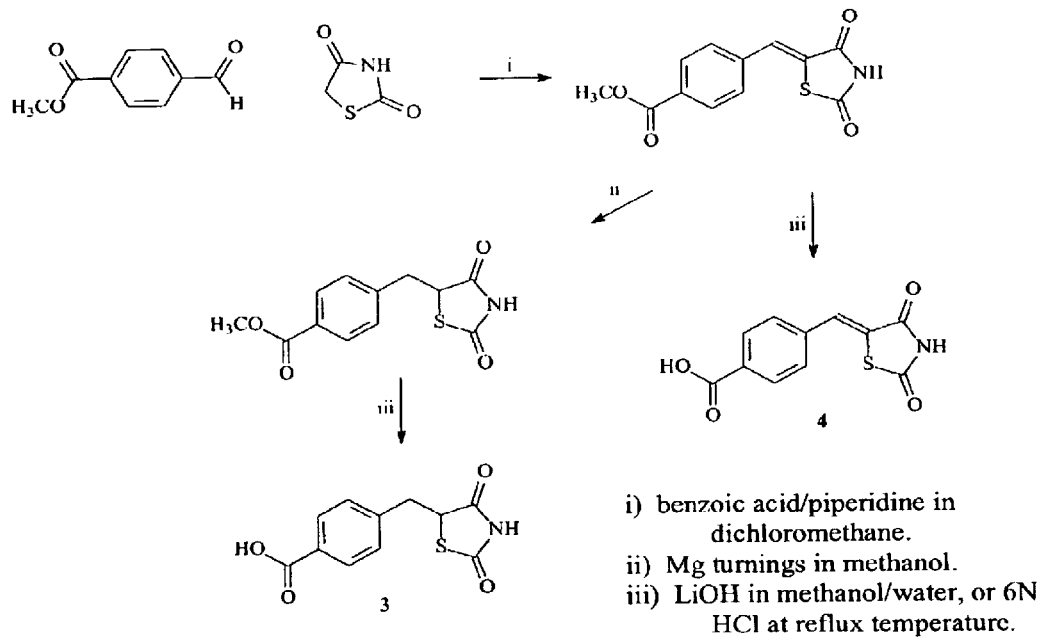

Ethyl acetoacetate 32 undergoes the same chemical treatment in steps 27 to 29 as acetylacetone 7 in steps 6 to 9 (FIG. 3). Thus, compound 32 in glacial acetic acid reacts with sodium nitrite, and the resulting oxime intermediate is not isolated but is reduced with zinc powder in acetic acid to give the amine 33. The amine is then coupled with benzoyl chloride in dichloromethane in the presence of triethylamine. The resulting benzamide 34 is then cyclized with a catalytic amount of sulfuric acid in refluxing ethyl acetate, giving the substituted oxazole 35.

In step 30, the ethyl carboxylate function of compound 35 is reduced with lithium aluminum hydride in THF to give the primary alcohol 36 (an analog of compounds 12 and 13).

In step 31, the ethyl carboxylate function of compound 35 is hydrolyzed in 6N HCl to give the carboxylic acid 37 (an analog of compound 6).

Figure 2:
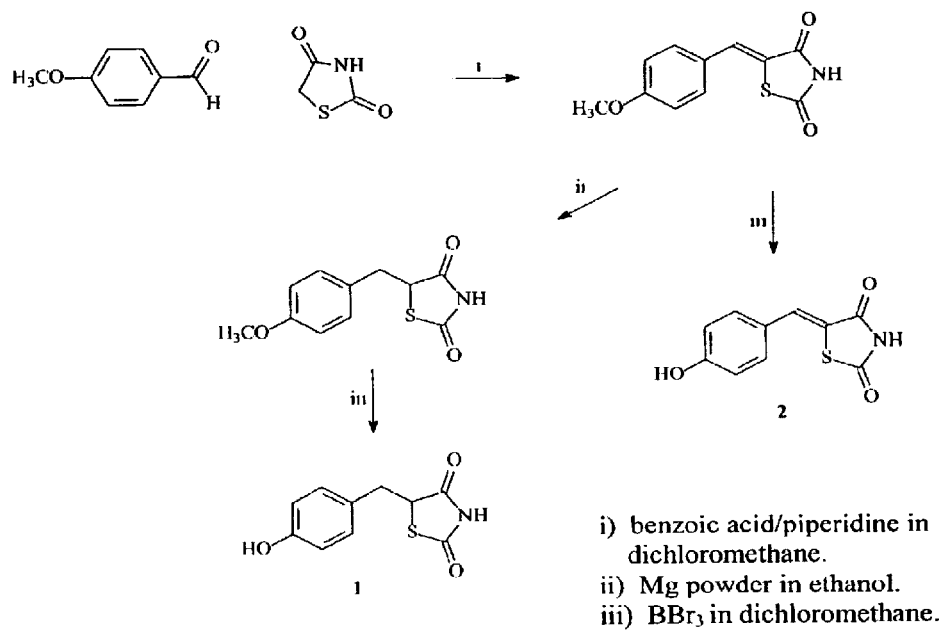
FIGS. 2–3 provide an exemplary synthetic scheme for compounds 1 through 4 (of Table I). These compounds can be conveniently prepared by the Knoevenagel reaction between an aldehyde and thiazolidine-2,4-dione using, for example, sodium acetate in acetic anhydride, or piperidine and benzoic acid in methylene chloride as a reaction medium.
Figure 4:
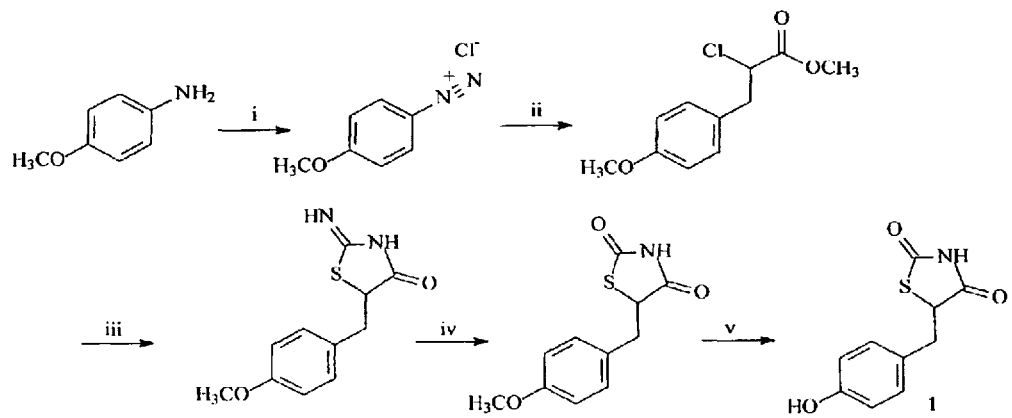
FIG. 4 illustrates an alternative reaction scheme for the production of compound 1 (of Table I). In this reaction scheme, para-anisidine undergoes a diazotation reaction with sodium nitrite and hydrochloric acid. The diazonium chloride salt undergoing, in turn, a radicalar reaction with methyl acrylate and then a cyclization reaction with thiourea, the product of which is hydrolyzed to the thiazolidinedione molecule.

Compounds 1 through 4 (of Table I) can be conveniently prepared by the Knoevenagel reaction between an aldehyde and thiazolidine-2,4-dione, using for example sodium acetate in acetic anhydride, or piperidine and benzoic acid in methylene chloride as a reaction medium. This is illustrated in FIG. 2 and FIG. 3. Alternatively, compound 1 can be prepared by the method described in FIG. 4. In this reaction scheme, para-anisidine undergoes a diazotation reaction with sodium nitrite and hydrochloric acid. The diazonium chloride salt undergoing, in turn, a radicular reaction with methyl acrylate and then a cyclization reaction with thiourea, the product of which is hydrolyzed to the thiazolidinedione molecule.

Figure 5:
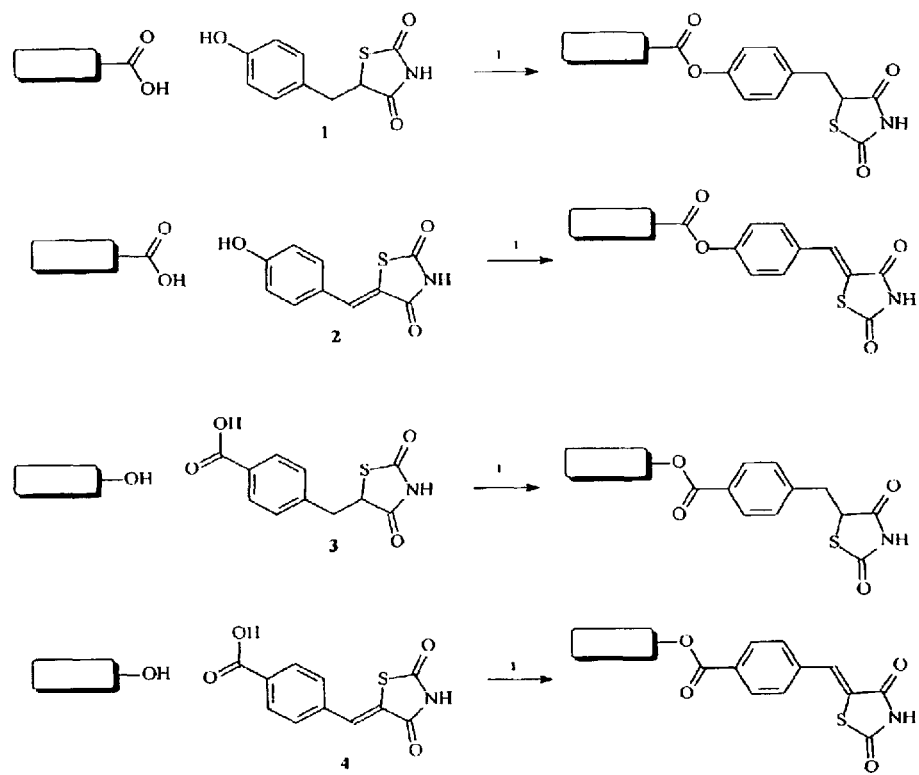
FIG. 5 shows an exemplary synthetic scheme for the compounds described in Table I (compounds 5 to 32). These compounds can be made via an esterification reaction between 1 or 2 and an appropriately substituted carboxylic acid, or between 3 or 4 and an appropriately substituted alcohol.

The compounds described in Table I (compounds 5 to 32) can all be made via an esterification reaction between 1 or 2 and an appropriately substituted carboxylic acid, or between 3 or 4 and an appropriately substituted alcohol. The esterification reaction can be facilitated by the presence of a catalyst in the reaction medium, such as a small amount of concentrated sulfuric acid for example. Preferably, especially if the alpha-position to the carbonyl is an asymmetric center, an activated functional derivative of the carboxylic acid is made. Numerous functional derivatives of carboxylic acids used in esterification reactions have been described in the scientific literature. The most commonly used activated functional derivatives are acyl chlorides, anhydrides and mixed anhydrides, and activated esters. In one aspect of this invention dicyclohexyl carbodiimide (DCC) was used as an activating agent (FIG. 5).

Compounds 33 to 104 are functionalized 5-methyloxazole and functionalized 5-methylthiazole derivatives. They all have various functional groups attached to the 2-position ($R_1$ in Tables II to V), and at the 4-position, which is the enzymatically labile link with the thiazolidine portion of the molecule. The enzymatically labile link is either an ester (COO—) or a reverse ester (OOC—) and can be substituted with 0, 1, or 2 methyl groups at the alpha-position from the oxazole or thiazole ring ($R_2$ and $R_3$ in Tables II to V).

Figure 6:
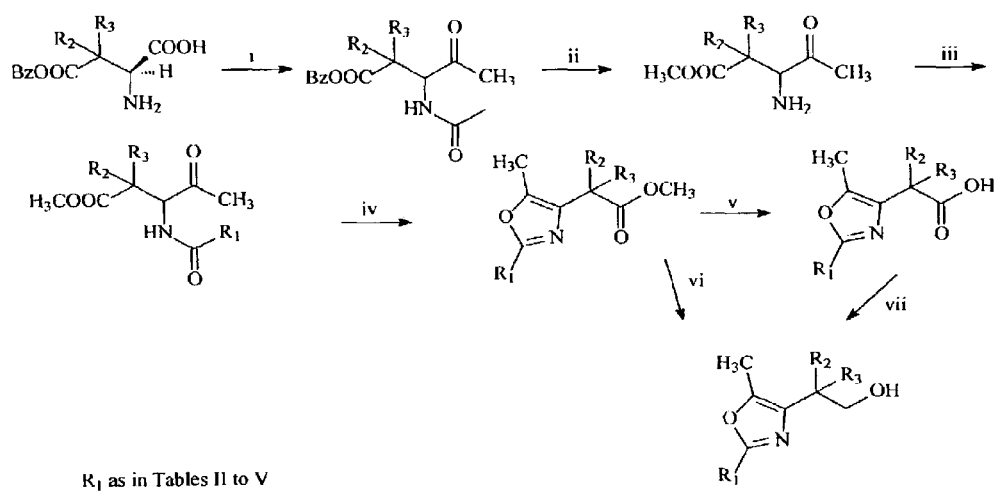
FIG. 6 depicts the synthesis of the 4-oxazoleacetic acid and the 4-oxazoleethanol moiety starting from aspartic acid derivatives in which $R_2$ and $R_3$ are methyl or hydrogen.

The synthesis of compounds 33 to 104 is described in general terms in FIGS. 7–10. FIG. 6 describes the synthesis of the 4-oxazoleacetic acid and the 4-oxazoleethanol moiety starting from aspartic acid derivatives in which $R_2$ and $R_3$ are methyl or hydrogen. In a typical example, γ-benzyl aspartate is acetylated and then decarboxylated to benzyl 3-acetamido-4-oxovalerate using acetic anhydride as an acetylating agent followed by potassium hydroxide in order to obtain the decarboxylated product. This in turn is transformed into methyl 3-amino-4-oxovalerate using standard hydrolytic and esterification procedures, for example refluxing in dilute hydrochloric acid followed by reaction in thionyl chloride and methanol. The $R_1$ group is then introduced by acylating the 3-amino group using the appropriate acyl or aroyl chloride. There is almost no limitation to the nature of the $R_1$ group being introduced at this stage, as shown in Tables II to V where various $R_1$ groups are described. Cyclization to an oxazole ring is then effected using sulfuric acid as a catalyst in ethyl acetate as a solvent. At this stage, ester hydrolysis using lithium hydroxide in methanol gives the desired 4-oxazoleacetic acid derivatives, whereas reduction of the ester with lithium aluminum hydride or reduction of the acid using diborane gives the 4-oxazoleethanol analogs.

Figure 7:
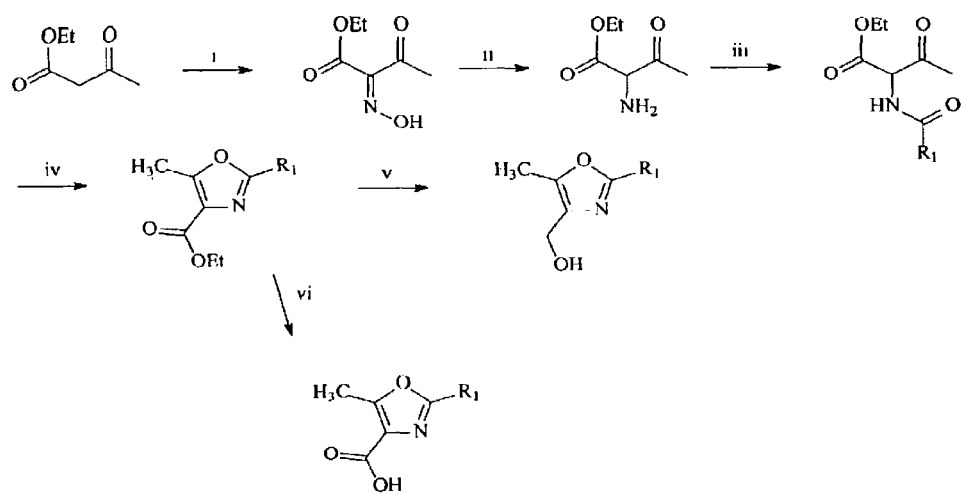
FIG. 7 describes the synthesis of the 4-oxazolecarboxylic acid and 4-oxazolemethanol groups. The synthesis starts from ethyl acetoacetate in which a 2-amino-group is introduced via oxime formation followed by reduction with zinc powder. The synthesis then proceeds as before, where the $R_1$ group is introduced by acylating the amino group, followed by cyclization with sulfuric acid in ethyl acetate, and finally ester cleavage or reduction to the alcohol.

FIG. 7 describes the synthesis of the 4-oxazolecarboxylic acid and 4-oxazolemethanol groups. The synthesis starts from ethyl acetoacetate in which a 2-amino-group is introduced via oxime formation followed by reduction with zinc powder. The synthesis then proceeds as before, where the $R_1$ group is introduced by acylating the amino group, followed by cyclization with sulfuric acid in ethyl acetate, and finally ester cleavage or reduction to the alcohol.

Figure 8:
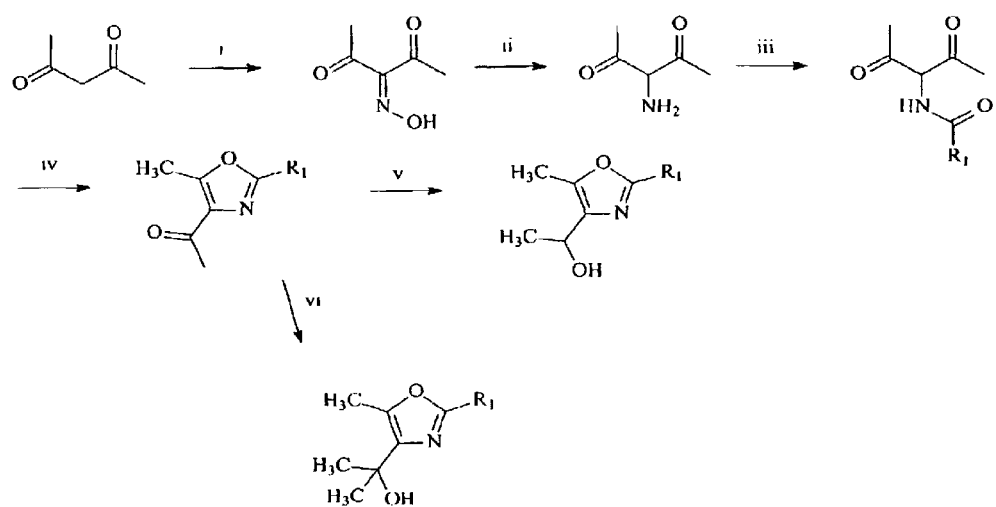
FIG. 8 shows how steric hindrance can be introduced under the form of methyl groups on the 4-methanol moiety. Starting from pentane-2,4-dione and following the same synthetic sequence as in FIG. 7 leads to the 4-acetyloxazole compounds which can be reduced by sodium borohydride to the 4-(1-ethyl)oxazole, or which can be transformed to 4-(2-hydroxy-2-propyl) oxazole with a methyl Grignard reagent such as methyl magnesium iodide.
Figure 9:
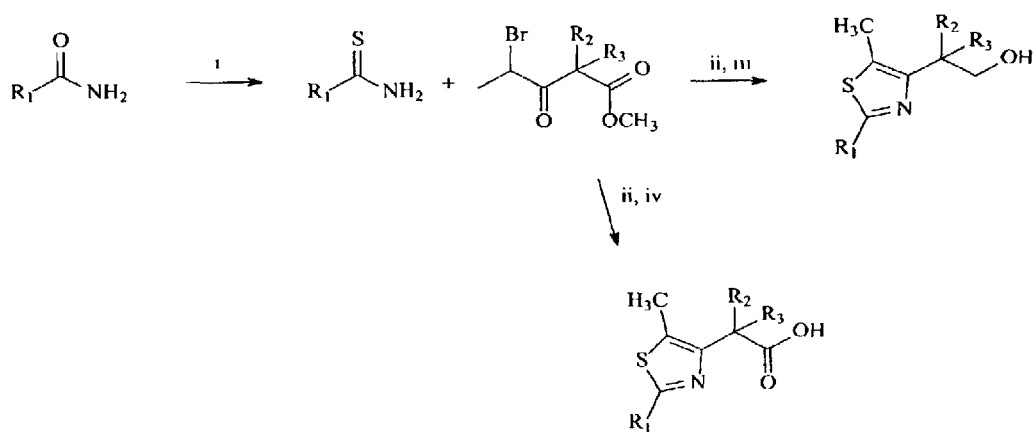
FIG. 9 illustrates an alternative synthetic scheme wherein condensation of a thioamide with methyl 4-bromo-3-oxopentanoate gives methyl 4-thiazoleacetate. Ester cleavage with lithium hydroxide or reduction with lithium aluminum hydride gives the corresponding acid or the alcohol, respectively.
Figure 10:
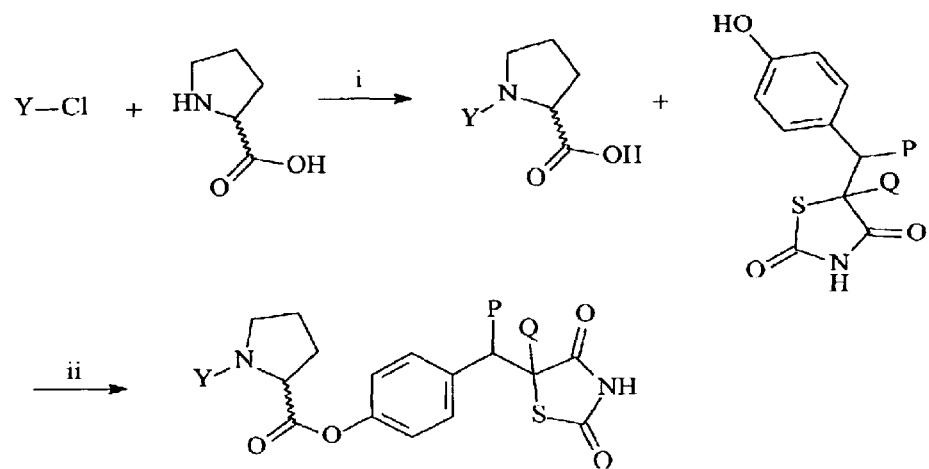
FIGS. 10–17 depict the synthesis of compounds 105 to 224 in Tables VI to XVII. These compounds contain an amino acid or an amino alcohol as part of their structure.
Figure 11:
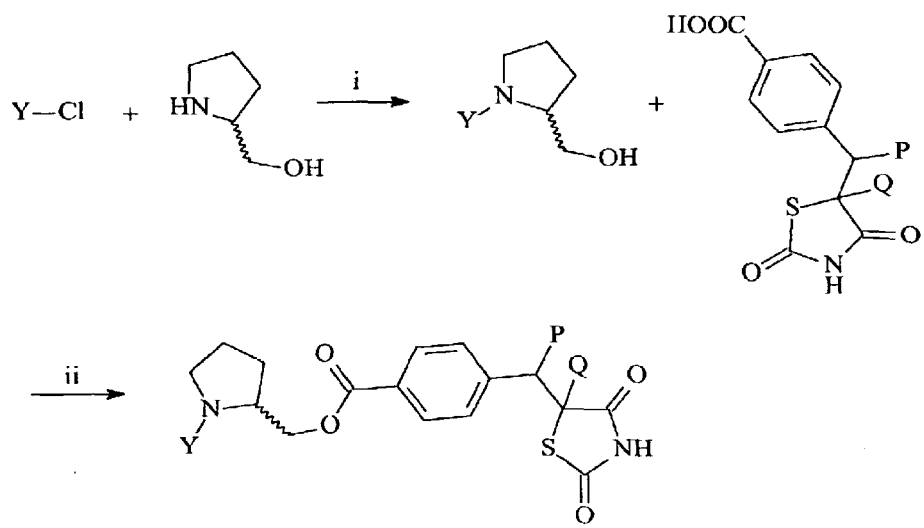
Figure 12:
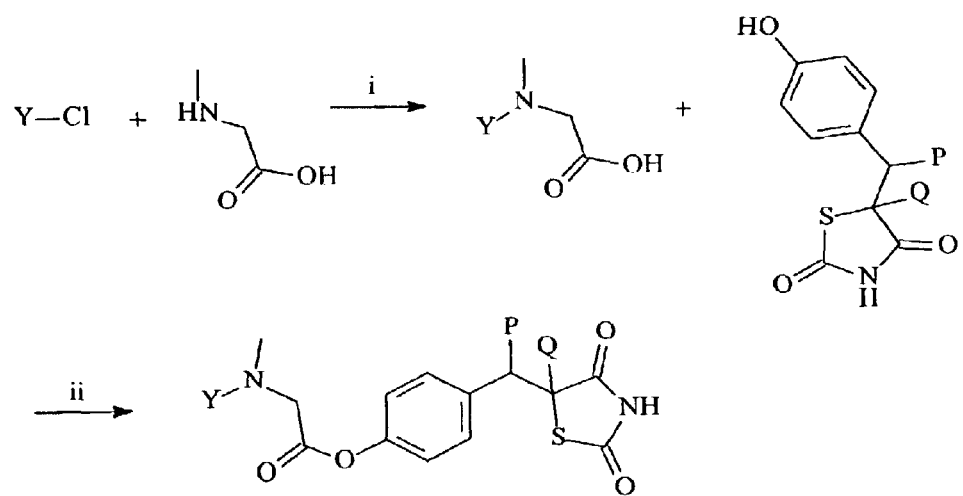
Figure 13:
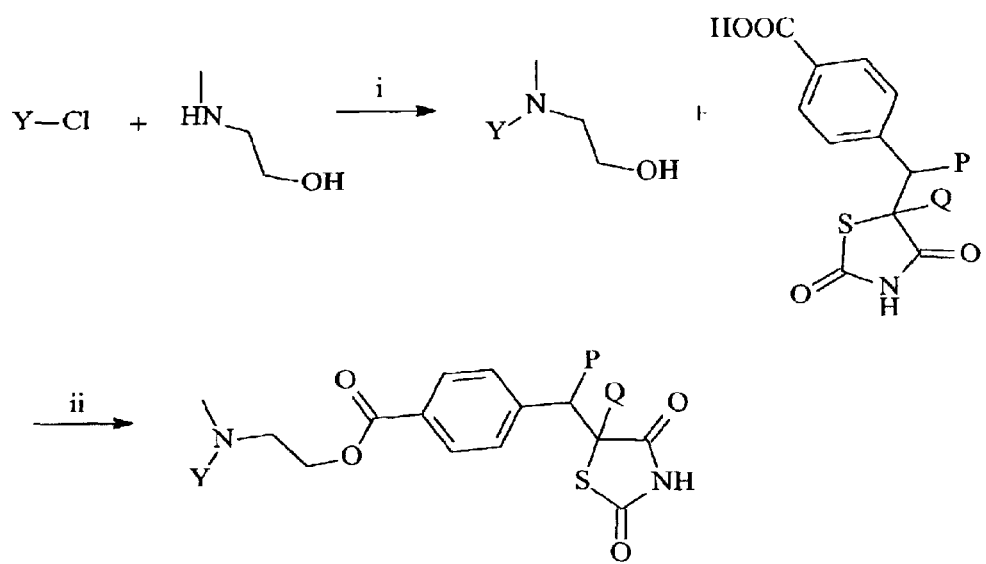
Figure 14:
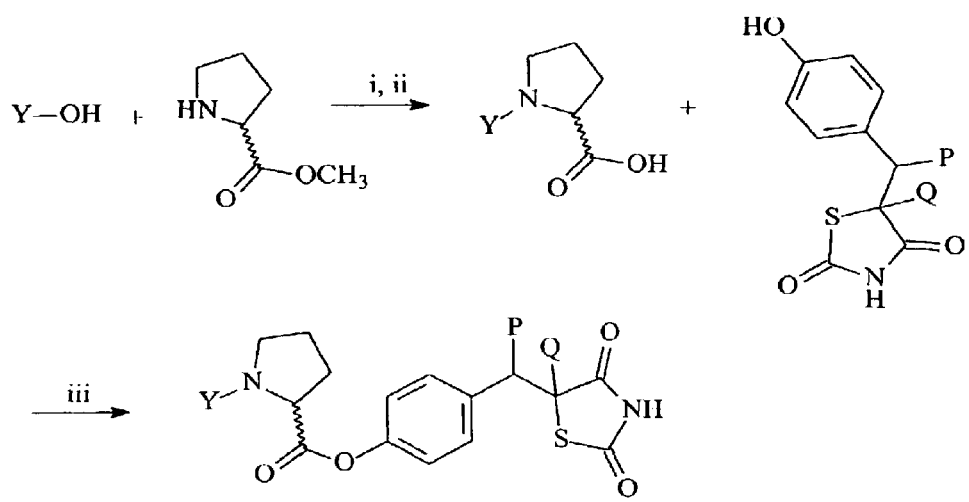

FIG. 8 shows how steric hindrance can be introduced under the form of methyl groups on the 4-methanol moiety. Starting from pentane-2,4-dione, following the same synthetic sequence as in FIG. 7 leads to the 4-acetyloxazole compounds which can be reduced by sodium borohydride to the 4-(1-ethyl)oxazole. Alternatively, the compounds can be transformed by methylmagnesium iodide into the tertiary alcohol analogs. In another embodiment, condensation of a thioamide with methyl 4-bromo-3-oxopentanoate gives methyl 4-thiazoleacetate, as described in FIG. 9. Ester cleavage with lithium hydroxide or reduction with lithium aluminum hydride gives the corresponding acid or the alcohol, respectively.

Compounds 105 to 224 in Tables VI to XVII all have an amino acid or an amino alcohol as part of their structure. Their synthesis is described in FIGS. 10 to 18. Any amino acid can be used in the synthesis of compounds according to this aspect of the invention. In certain embodiments, the amino acid group can be either proline or N-methyl glycine and the amino alcohol group is their alcohol equivalent, i.e., prolinol or N-methyl glycinol, respectively. As shown in FIGS. 10 to 13, the reaction of an alkyl chloride or a 2-heteroaryl chloride with proline, prolinol, N-methyl glycine, or N-methyl glycinol, in THF and triethylamine gives the corresponding N-alkyl or N-heteroaryl adduct, respectively. When these adducts are carboxylic acids, such as in FIGS. 10 and 12, they react with 5-(4-hydroxybenzyl)thiazolidine-2,4-dione in the presence of DCC and DMAP to give compounds 105–108, 111, 112, 125–128, 131, 132, 185–188, 191, 192. Carboxylic acid adducts react with 5-(4-hydroxybenzylidene)thiazolidine-2,4-dione in the presence of DCC and DMAP to give compounds 115–118, 121, 122, 135–138, 141, 142, 195–198, 201, 202. When these adducts are alcohols, such as in FIGS. 11 and 13, they react with 5-(4-carboxybenzyl)thiazolidine-2,4-dione in the presence of DCC and DMAP to give compounds 145–148, 151, 152, 165–168, 171, 172, 205–208, 211, 212. Alcohol adducts react with 5-(4-carboxybenzylidene)thiazolidine-2,4-dione in the presence of DCC and DMAP to give compounds 155–158, 161, 162, 175–178, 181, 182, 215–218, 221, 222.

Alternatively, the amino acid or amino alcohol group can be linked to another group via an amide function, such as described in FIGS. 14 to 17. The synthesis of such compounds is straightforward. When the compounds contain an amino acid, as in FIGS. 14 and 16, the synthetic sequence is an amide bond formation, ester deprotection, and ester formation.

As an illustrative example, (R)-Trolox® is combined with L-proline methyl ester, in the presence of DCC and DMAP in methylene chloride to form an amide intermediate. The methyl ester of the proline group is then cleaved with lithium hydroxide in methanol, and the resulting carboxylic acid is combined with 5-(4-hydroxybenzyl)thiazolidine-2,4-dione in DCC/DMAP/methylene chloride to give compound 109. The (S)-isomer, compound 110, is made in a similar way. The same kind of synthetic scheme leads to compounds 113, 114, 119, 120, 123, 124, 129, 130, 133, 134, 139, 140, 143, 144, 189, 190, 193, 194, 199, 200, 203, and 204.

Figure 15:
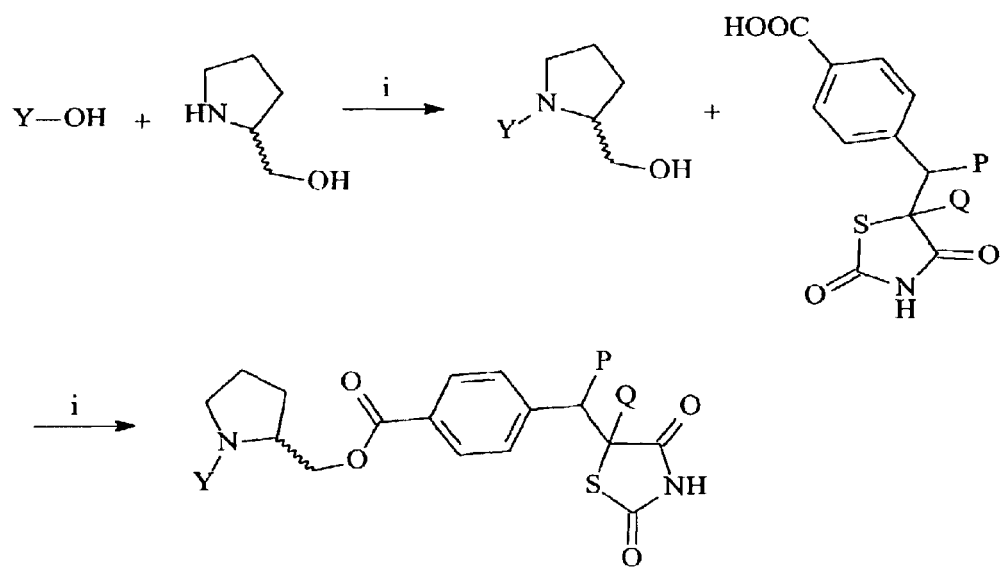
Figure 16:
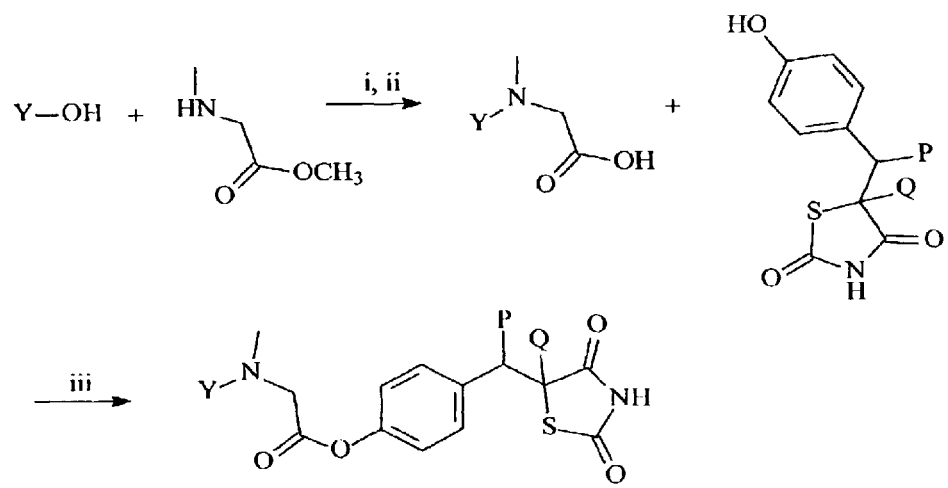
Figure 17:
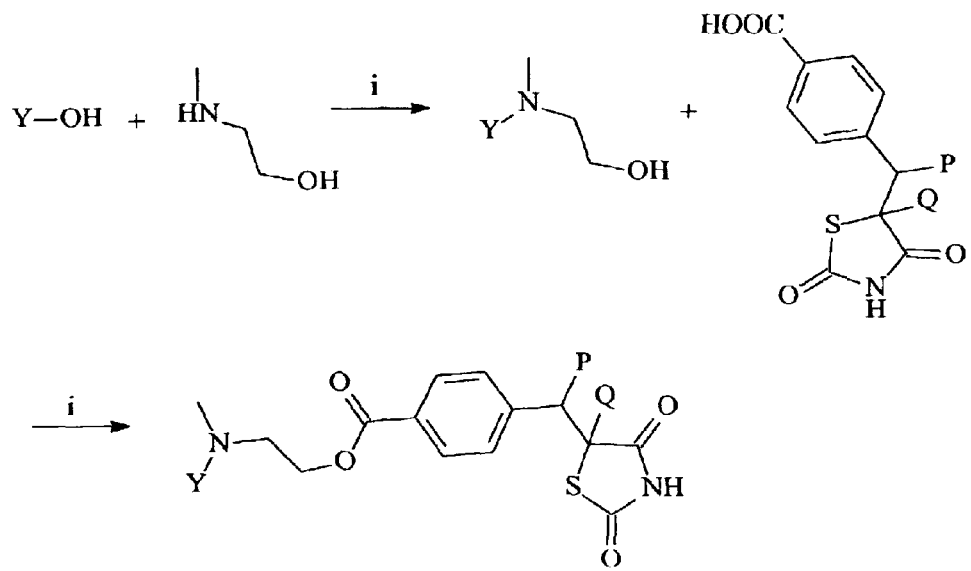
Figure 18:
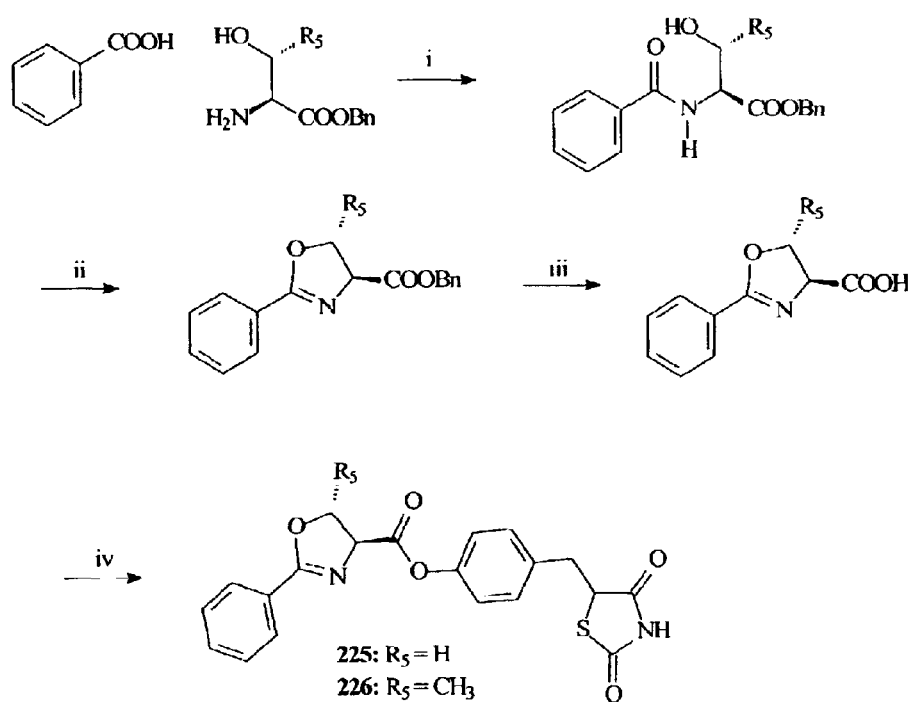
FIG. 18 provides an exemplary synthetic pathway for compounds 225 to 242 (Table XVIII). These compounds are oxazoline-4-carboxylic acid types of compounds. Their synthesis (FIG. 18) starts from serine ($R_5$=H) or from threonine ($R_5$=CH$_3$) benzyl ester. The ester is coupled with an alkyl or an arylcarboxylic acid using for example EDC as a coupling agent. The serine or threonine group then cyclizes into an oxazoline upon treatment with thionyl chloride. Coupling with 5-(4-hydroxybenzyl)thiazolidine-2,4-dione using DCC/DMAP/methylene chloride gives compounds 225 to 242.

When the compounds contain an amino alcohol, as in FIGS. 15 and 17, the synthetic sequence is an amide bond formation, followed by an ester bond formation. As an illustrative example, (R)-Trolox® is combined with L-prolinol in the presence of DCC and DMAP in methylene chloride to form an amide intermediate. The resulting amide is combined with 5-(4-carboxybenzyl)thiazolidine-2,4-dione in DCC/DMAP/methylene chloride to give compound 149. The (S)-isomer, compound 150, is made in a similar way. The same kind of synthetic scheme leads to compounds 153, 154, 159, 160, 163, 164, 169, 170, 173, 174, 179, 180, 183, 184, 209, 210, 213, 214, 219, 220, 223, and 224.

Compounds 225 to 242 (Table XVIII) are oxazoline-4-carboxylic acid types of compounds. Their synthesis (FIG. 18) starts from serine ($R_5$=H) or from threonine ($R_5$=$CH_3$) benzyl ester. The ester is coupled with an alkyl or an arylcarboxylic acid using for example EDC as a coupling agent. The serine or threonine group then cyclizes into an oxazoline upon treatment with thionyl chloride. Coupling with 5-(4-hydroxybenzyl)thiazolidine-2,4-dione using DCC/DMAP/methylene chloride gives compounds 225 to 242.

Compounds 243 to 248 (Table XIX) are thiazolidinedione molecules where X is a group containing a substituted 2-methyl-2-propionyl residue. Examples include the 2-methyl-2-(4-chlorophenoxy)propionyl moiety (clofibryl moiety), the 2-methyl-2-[4-(4-chlorobenzoyl)phenoxy] propionyl moiety (fenofibryl moiety), and 2,2-dimethyl-5-(2,5-xylyloxy)valeryl moiety (gemfibrozilyl moiety).

Compounds 249 to 252 (Table XX) are thiazolidinedione molecules where X is a group containing a substituted (R,R)-3,5-dihydroxyheptanoyl residue. Examples include the (βR, δR)-2-(4-fluorophenyl)-5-(1-methylethyl)-3-phenyl-4-[(phenylamino)carbonyl] 1H-pyrrole-1-(β,δ,dihydroxy)heptanoyl group (atorvastatin), and the 1,2,3,7,8,8a-hexahydro-1-(2-methylbutanoyl)oxy-3,7-dimethylnaphthalenyl-8-[(3R,5R)-7-heptan]oyl group (lovastatin). The synthesis of these compounds proceeds as in the examples of Table I, (i.e., by a simple esterification procedure between the lipid-lowering agent and compound 1 or compound 2).

Compounds 253 to 260 (Table XXI) are thiazolidinedione molecules where X is a group containing an arylacetic acid residue, such as in molecules that have non-steroidal anti-inflammatory properties. In these examples, the X group is an ibuprofen, ibufenac, naproxen, diclofenac, or nabumetone residue. The synthesis of these compounds is a simple ester formation reaction between the X group and compound 1 (P and Q are hydrogen) or compound 2 (P and Q form a bond).

Compounds 261 to 268 (Table XXII) are thiazolidinedione molecules where X is a group containing a cortienic acid residue, such as in molecules that have glucocorticoid anti-inflammatory properties. In these examples, the X group is a cortienic acid, 1,2-dihydrocortienic acid, 6α, 9α-difluoro-1,2-dihydrocortienic acid, and a 9α-fluoro-16α-methyl-1,2-dihydrocortienic acid residue. The synthesis of these compounds is a simple ester formation reaction between the X group and compound 1 (P and Q are hydrogen) or compound 2 (P and Q form a bond). Cortienic acid, one of the many metabolites of hydrocortisone in man, can be synthetized from hydrocortisone by oxidation with sodium periodate. The substituted cortienic acid analogs can be made in an identical manner from the corresponding substituted glucocorticoids. This oxidation procedure is described in detail in [Druzgala P.: Novel Soft Anti-inflammatory Glucocorticoids for Topical Application. Ph.D. Dissertation (1985), University of Florida, Gainesville, Fla., hereby incorporated by reference in its entirety].

Figure 19:
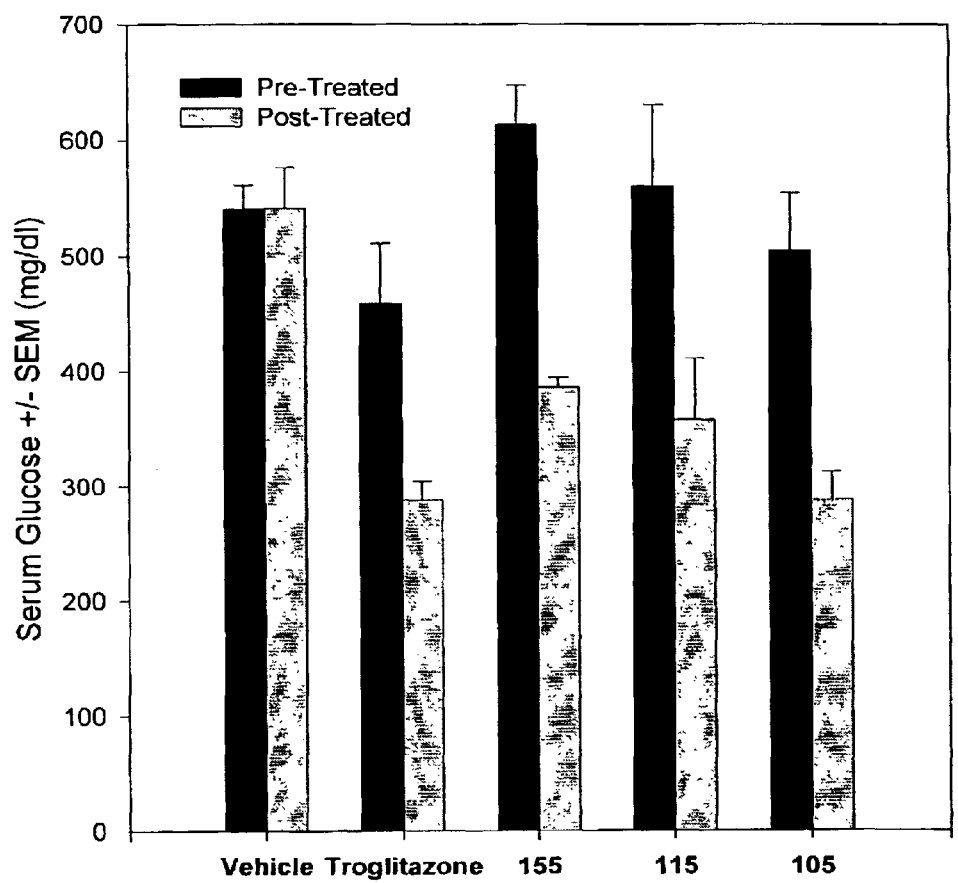
FIGS. 19–20 illustrate the activity of representative compounds on serum glucose and insulin levels in non-insulin dependent diabetic mellitus (NIDDM) KK-A$^y$ male mice. Post-treatment data for each group were transferred to a percentage of pretreatment values and unpaired Student's t test was used for comparison between vehicle and test substance treated groups. Results show a significant reduction of both serum glucose and serum insulin relative to the vehicle control group. Reduction in serum glucose and serum insulin levels were comparable to the reduction observed in the troglitazone-treated animals. The results are also presented in Table XXI.
Figure 20:
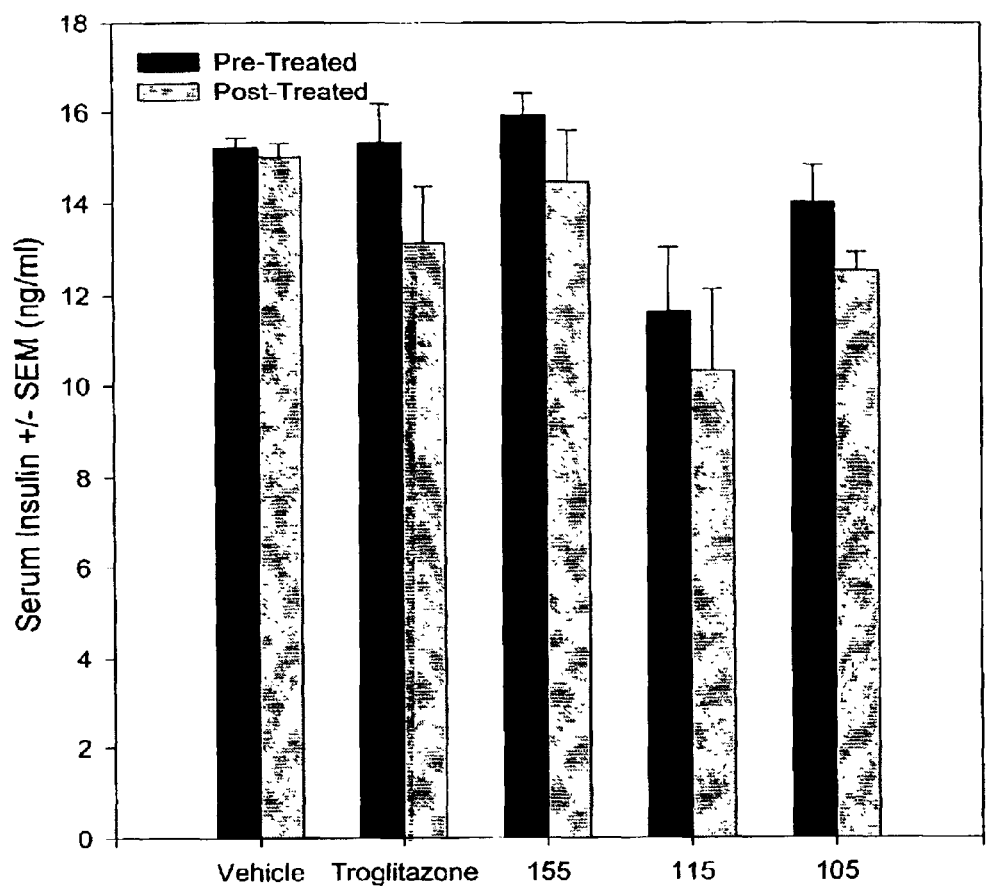

Representative compounds were chosen and evaluated for activity on serum glucose and insulin levels in non-insulin dependent diabetic mellitus (NIDDM) KK-A$^y$ male mice. Post-treatment data for each group were transferred to a percentage of pretreatment values and unpaired Student's t test was used for comparison between vehicle and test substance treated groups. Results show a significant reduction of both serum glucose and serum insulin relative to the vehicle control group. Reduction in serum glucose and serum insulin levels were comparable to the reduction observed in the troglitazone-treated animals. The results are presented in Table XXI and in FIGS. 19 and 20.

The subject invention also provides compounds comprising the following formula:

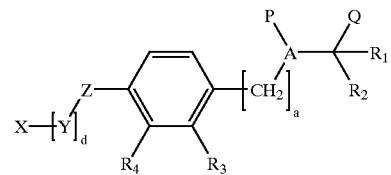

FORMULA II wherein a is 0 to 4;

P and Q are H or $CH_3$, or P and Q form a bond, therefore resulting in a double bond between A and the adjacent carbon atom;

A is CH, N, O, or S; however, if A is O or S, then P is absent from Formula II, and Q is H or $CH_3$;

$R_1$ and $R_2$ are linked and together form a chain having a length of 4- or 5-atoms, said chain containing at least 1 but optionally 2 or even 3 heteroatoms from the group O, S, or N, and said chain optionally containing at least 1 or 2 carbonyl (C=O) groups;

or wherein $R_1$ and $R_2$ are not linked, and $R_1$ can be —(C=O)$NH_2$, —(C=O)OH, tetrazole, or —(C=O)O—$C_{1-6}$alkyl; and $R_2$ can be a hydrogen atom; $C_{1-3}$ alkyl; $C_{1-6}$ alkoxy; $C_{0-3}$ alkylenephenyl, wherein the phenyl ring may be optionally substituted by 1 or more halogen atoms; tetrazole ring; (C=O)OH; (C=O)O—$C_{1-6}$ alkyl;

(C=O)$_b$$NR_5R_6$, wherein b is 0 or 1; $R_5$ is H or $C_{1-6}$alkyl; and $R_6$ is H or B(C=O)$_c$$DR_7$ or B(CHOH)$_c$$DR_7$, where c is 0 or 1, B is a bond, a $C_{1-6}$ alkylene, a $C_{2-6}$ alkenylene, a $C_{4-6}$ cycloalkenylene, a phenyl optionally substituted by 1 or more $C_{1-3}$ alkyl groups and/or 1 or more halogen atoms, or a 5- or 6-membered heterocyclic group containing at least 1 or optionally 2 heteroatoms (including any combination of O, N, or S at any position), where D is a bond, a $C_{1-3}$ alkyleneoxy, —O—, —NH—, or —N($C_{1-3}$ alkyl)—, and where $R_7$ is $C_{1-6}$ alkyl, $C_{4-6}$ cycloalkyl or cycloalkenyl, phenyl optionally substituted by 1 or more halogen atoms, $C_{1-3}$alkyl, $C_{1-3}$alkoxy, $C_{0-3}$alkylene$NR_8R_9$ (each of $R_8$ and $R_9$ being independently H, $C_{1-3}$ alkyl, $SO_2C_{1-3}$alkyl, (C=O)O$C_{1-3}$alkyl, $SO_2NHC_{1-3}$alkyl), $C_{0-3}$alkyleneCOOH, $C_{0-3}$alkylene(C=O)O$C_{1-3}$alkyl, $OCH_2$(C=O)$NH_2$, a 5- or 6-membered heterocyclic ring containing at least 1 or optionally 2 heteroatoms (including any combination of O, N, or S at any position), or a fused bicyclic ring containing a benzene ring fused with a 5- or 6-membered heterocyclic ring containing at least 1 heteroatom (including O, N, or S at any position), and optionally substituted by an oxo (=O) group, wherein said bicyclic fused ring can be attached to D via a ring atom of the heterocyclic ring either directly or through a $C_{1-6}$ alkylene $ER_{10}$ where E is O, S, or —$NR_{11}$—, $R_{10}$ and $R_{11}$ being independently H or $C_{1-3}$ alkyl;

$R_3$ and $R_4$ are, optionally, the same or different and can be H, $CH_3$, $CF_3$, $OCH_3$, or a halogen atom;

d is 0 or 1;

X can be a $C_{3-8}$ cycloalkyl optionally substituted by a $C_{1-3}$ alkyl, $C_{1-3}$ alkoxy, trifluoromethyl, hydroxy, cyano, (C=O)O$C_{1-6}$alkyl, amino, alkylamino, or dialkylamino; phenyl ring, optionally substituted by any combination of one or more halogen atoms, $C_{1-6}$ alkyl, $C_{1-6}$ alkoxy, $C_{1-6}$ fluoroalkoxy, nitrile, or —$NR_{12}R_{13}$ where $R_{12}$ and $R_{13}$ are independently H or $C_{1-6}$ alkyl; 5- or 6-membered heterocyclic ring containing at least 1, or optionally 2, or more heteroatoms such as O, S, or N, said heterocyclic ring being optionally substituted by a $C_{1-3}$ alkyl, $C_{1-3}$ alkoxy, trifluoromethyl, hydroxy, cyano, (C=O)O$C_{1-6}$alkyl, amino, alkylamino, or dialkylamino, provided that the heterocyclic ring may not be aromatic; fused bicyclic ring containing a phenyl ring fused with a 5- or 6-membered heterocyclic ring containing at least 1, or optionally 2 or more heteroatoms such as O, N, or S, wherein both rings can be, optionally, independently substituted by $C_{1-3}$ alkyl, $C_{1-3}$ alkoxy, trifluoromethyl, hydroxy, cyano, (C=O)O$C_{1-6}$alkyl, amino, alkylamino, or dialkylamino, and the heterocyclic ring may not be aromatic, provided that if d=0, then the bicyclic ring X is attached to Z either directly via a ring atom of the heterocyclic ring of X, or through a sequence $(CH_2)_f G_g (CH_2)_h (C=O)_i$, wherein G is O, S, NH, or N$C_{1-3}$alkyl, f is 0–6, g=0 or 1, h=0–6, and i=0 or 1; or if d=1, then the bicyclic ring X is attached to Y either directly between a ring atom of the heterocyclic ring of X and a nitrogen atom of Y, or through a sequence $(CH_2)_f G_g (CH_2)_h (C=O)_i$, where f, g, h, i, and G are defined as above;

Y is one of the following:

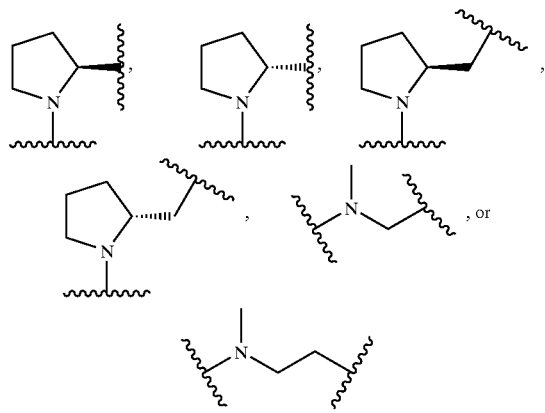

in which the nitrogen atom is attached to X as defined above and in which the 2-position of the pyrrolidine ring is attached to Z, either directly or through a methylene group;

Z is a group that can be enzymatically hydrolyzed or reduced, said enzymatic reduction or hydrolysis results in the cleaving of Z into 2 molecular fractions including moieties such as —O(C=O)—, —(C=O)O—, —(C=O)S—, —S(C=O)—, —O(C=O)O—, —S—S—, —O—P(=O)(O$C_{1-6}$alkyl)O—, —P(=O)(O$C_{1-6}$alkyl)O—, —N=N—, —(C=O)NH—, —NH(C=O)—, —NHSO$_2$—, —SO$_2$NH—, —SO$_3$—, —O$_3$S—, cholesteryl-O(C=O)O—, cholesteryl-O(C=O)—, androstane 17β-(C=O)— wherein the androtane group can contain 1–4 double bonds and can be optionally substituted by 1 or 2 oxo-groups, 1–4 halogen atoms, 1–4 hydroxyl groups, or 1–4 methyl groups;

alternatively, Z can also represent the following groups:

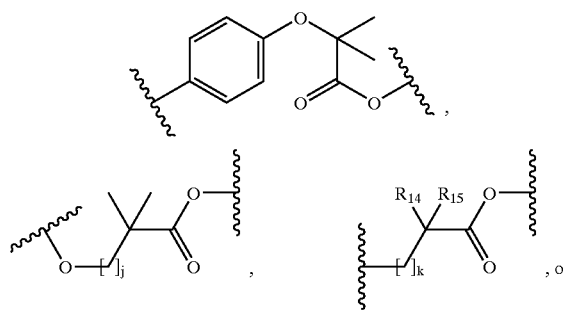

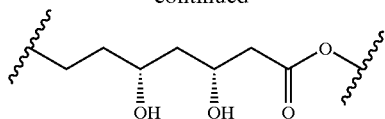

wherein j and k are integers from 0 to 4, and $R_{14}$ and $R_{15}$ independently represent H or $C_{1-3}$ alkyl.

In some embodiments, X—Y—Z— together represent HO—, HO(C=O)—, H$_2$N, or HO$_3$S—. Other embodiments provide compounds wherein the carbon center bearing Q and R2 can be of the (S)-, (R)-, or (R,S)-configuration. Yet other embodiments are provided wherein all the possible asymmetrical carbon centers can be of the (S)-, (R)-, or (R,S)-configuration. Unsaturated moieties can be of the cis- or trans-configuration.

A subgroup of compounds according to the present invention are represented by the formula of Formula III. These compounds represent the thiazolidinediones subgroup:

FORMULA III

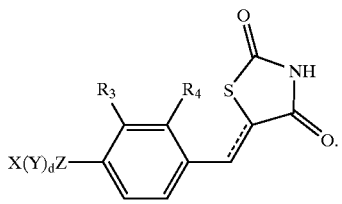

Another subgroup is represented by Formula IV. These represent the isoxazolidinediones subgroup:

FORMULA IV

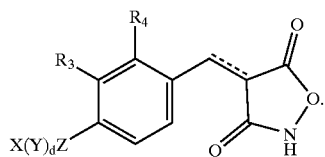

Another embodiment is depicted by Formula V. The compounds of this subgroup represent the benzylmalonate subgroup (P and Q are H) and the benzylidenemalonate subgroup (P and Q form a bond):

FORMULA V

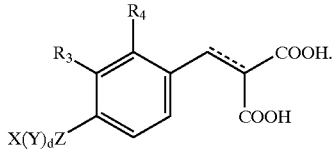

Yet another embodiment provides compounds having Formula VI. These represent the 2-phenoxyisobutyric acid subgroup:

FORMULA VI

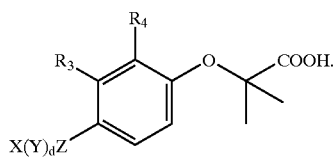

Other embodiments provide compounds of Formula VII, which represents the N-aroyl phenylalanine subgroup in which Ar is phenyl or a 5- or 6-membered heteroaryl group containing at least 1 atom selected from the group O, S, or N:

FORMULA VII

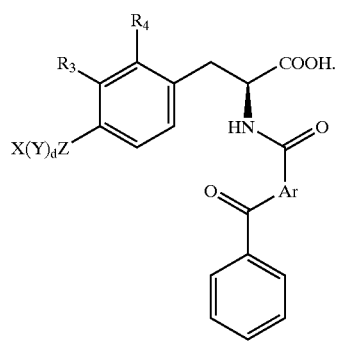

Formula VIII represents the N-aryl phenylalanine subgroup in which Ar is phenyl or a 5- or 6-membered heteroaryl group containing at least 1 atom from the group O, S, or N:

FORMULA VIII

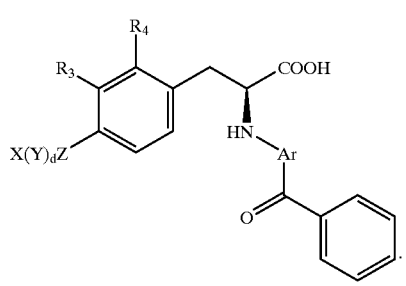

Another subgroup is depicted by Formulae IXA and IXB, the phenoxyacetic acid subgroup, where the carboxylic acid moiety can be replaced by a tetrazole ring:

FORMULA IXA

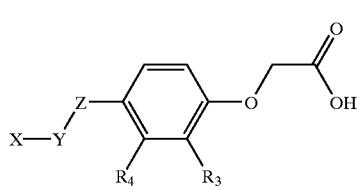

FORMULA IXB

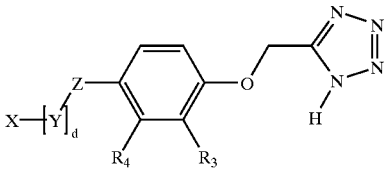

wherein $X(Y)_d Z$ can be the following:

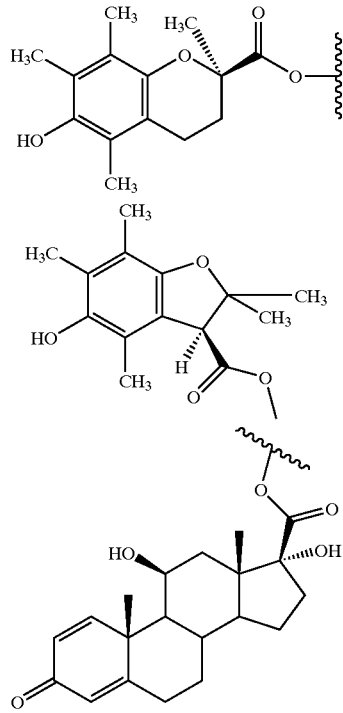

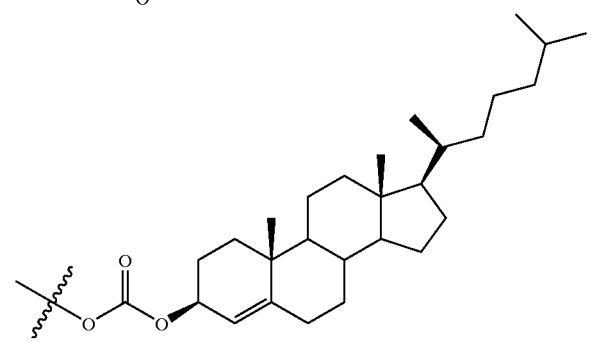

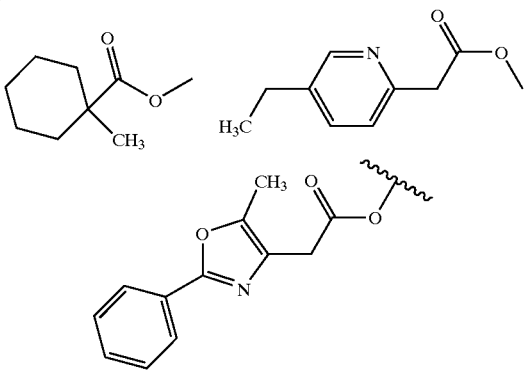

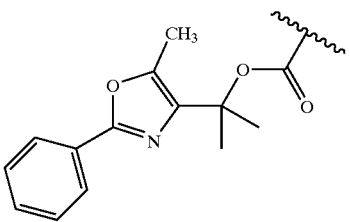

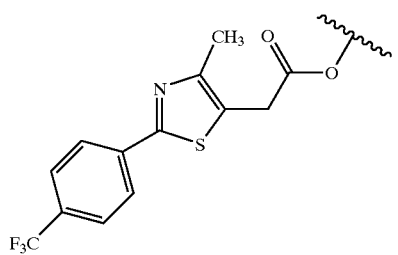

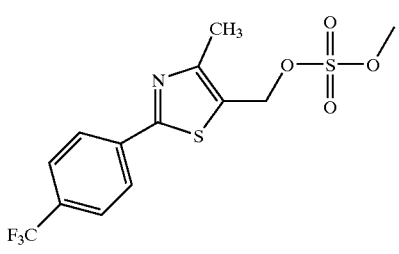

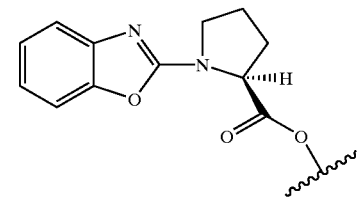

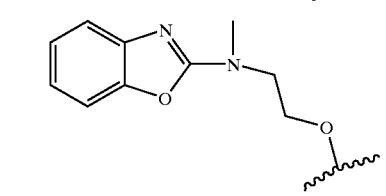

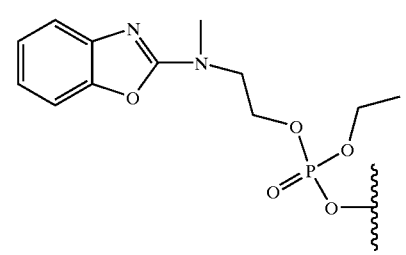

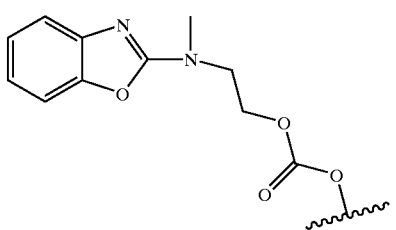 or

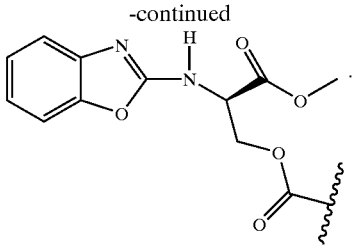

Figure 29:
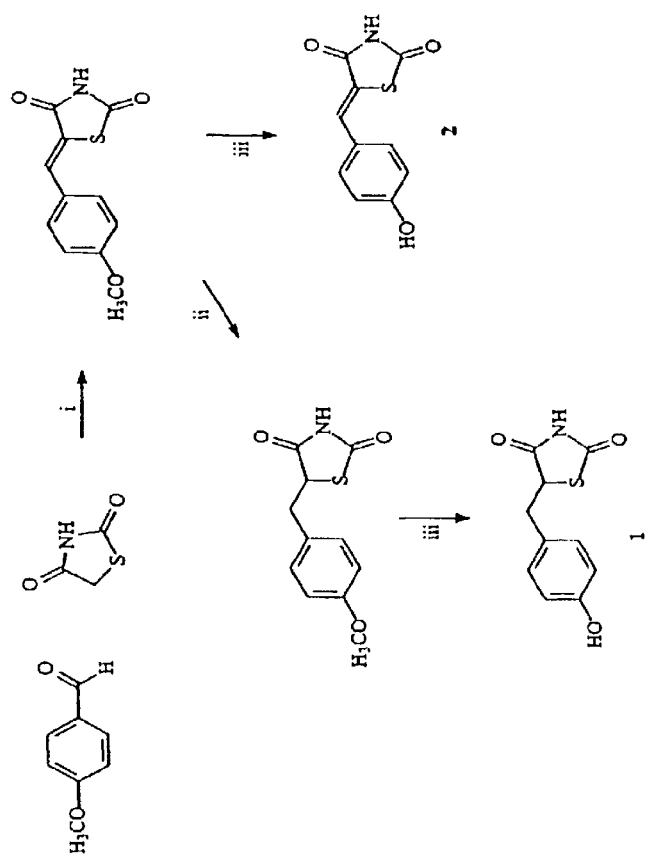
FIGS. 29–38 provide synthetic pathways for compounds of Formulas II–IX.
Figure 30:
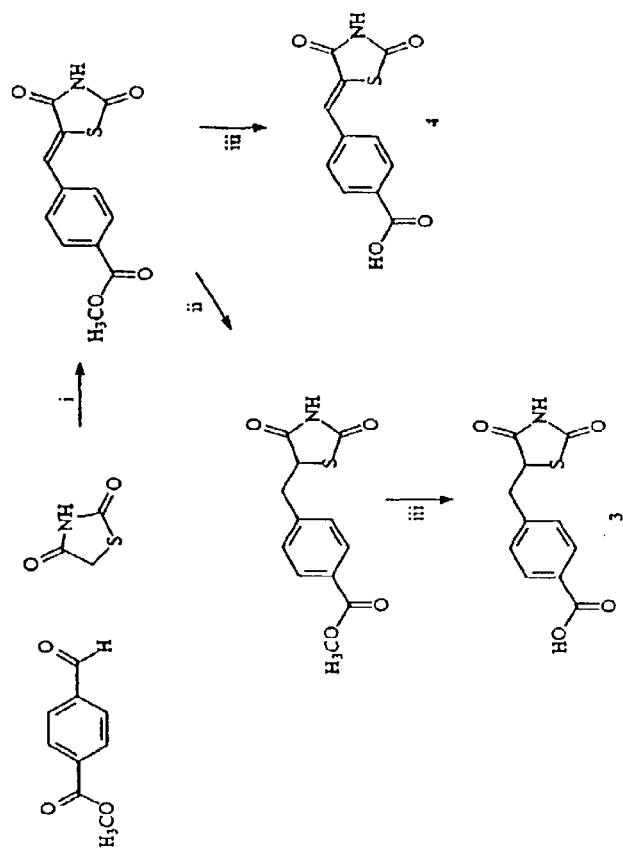
Figure 31:
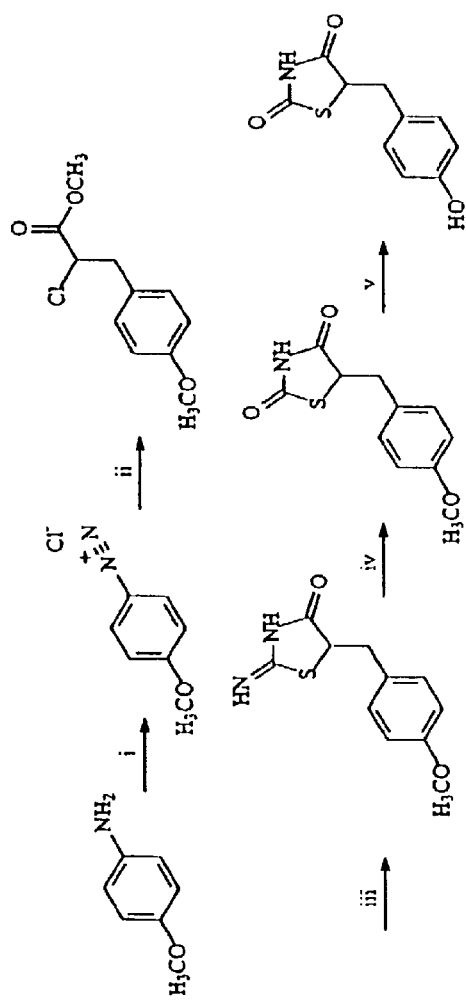

Compounds of Formula III can be conveniently prepared by the Knoevenagel reaction between an aldehyde and thiazolidine-2,4-dione, using for example sodium acetate in acetic anhydride, or piperidine and benzoic acid in methylene chloride as a reaction medium. This is illustrated in FIG. 29 and FIG. 30. Alternatively, the same compounds can be prepared by the method described in FIG. 31, in which para-anisidine undergoes a diazotation reaction with sodium nitrite and hydrochloric acid, the diazonium chloride salt undergoing in turn a radicalar reaction with methyl acrylate and then a cyclization reaction with thiourea, the product of which is hydrolyzed to the thiazolidinedione molecule.

Figure 32:
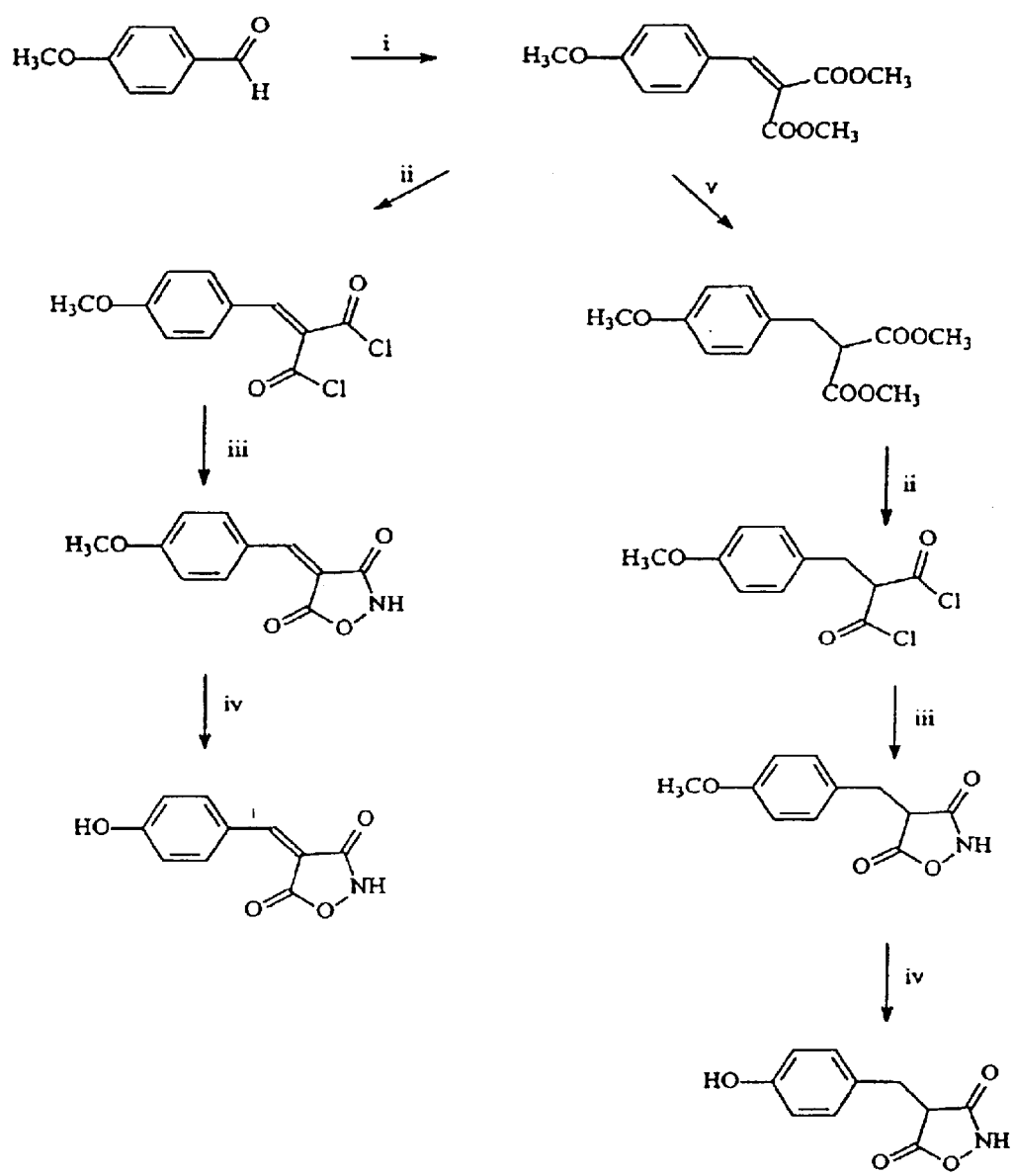

Compounds of Formulae IV and V can be conveniently prepared according to FIG. 32 where for example p-methoxybenzaldehyde reacts in step (i) with dimethyl malonate in methanol with a catalytic amount of piperidinium benzoate, giving the benzylidene product. In step (ii), the benzylidene is hydrolyzed in methanol/NaOH/water and then is acidified with dilute HCl to give the diacid. The diacid in turn reacts with thionyl chloride to give the acid chloride. In step (iii), the acid chloride is dissolved in dichloromethane and triethylamine. Hydroxylamine hydrochloride is added under ice-cooling, giving the isoxazolidine compound. In step (iv), the methoxy-group is cleaved readily by boron trifluoride, yielding the phenolic product. Finally, in step (v), the benzylidene is reduced by magnesium powder in ethanol, giving dimethyl 4-methoxybenzylmalonate.

Figure 33:
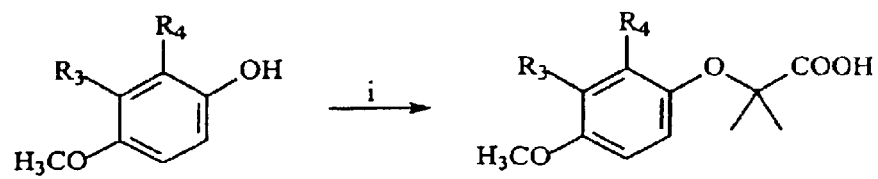

Compounds of Formula VI can be conveniently prepared from the reaction of a phenol with acetone, chloroform, and sodium hydroxide, as shown in FIG. 33.

Figure 34:
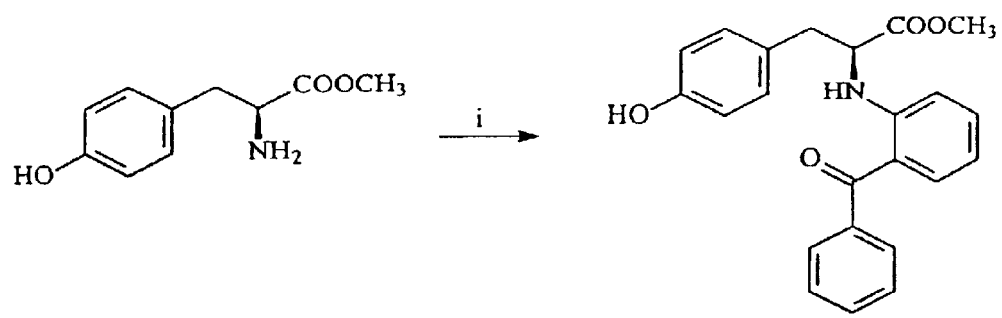
Figure 35:
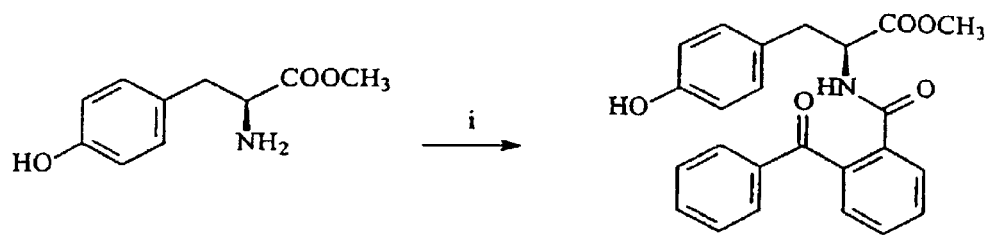

Compounds of Formulae VII and VIII are tyrosine derivatives that are substituted on the tyrosine nitrogen. They can be conveniently synthesized from tyrosine methyl ester and 2-benzoylcyclohexanone followed by reduction with 10% Pd/C as a catalyst (FIG. 34), or from tyrosine methyl ester and 2-benzoylcyclohexanecarbonyl chloride, followed by reduction with 10% Pd/C as a catalyst (FIG. 35).

Figure 36:
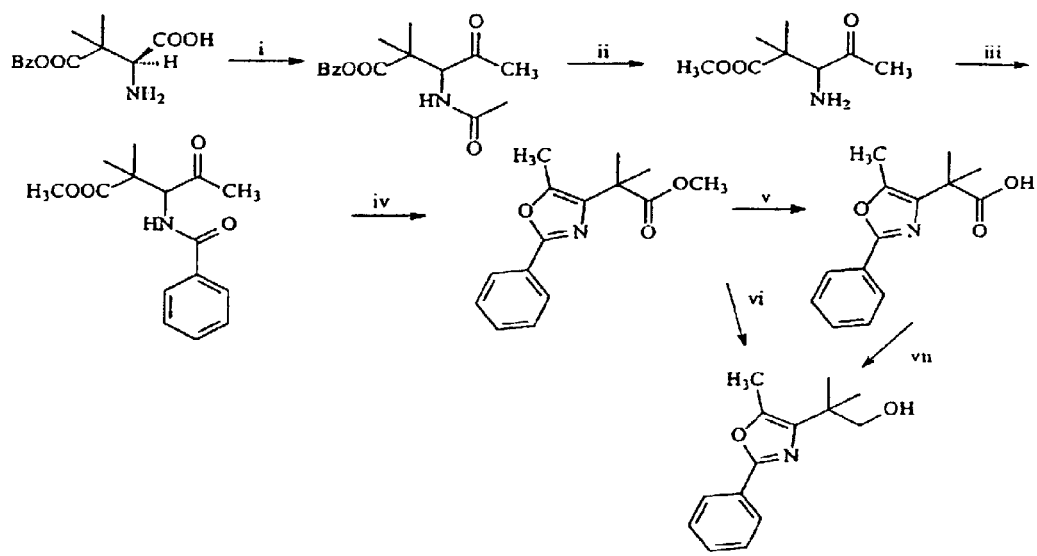
Figure 37:
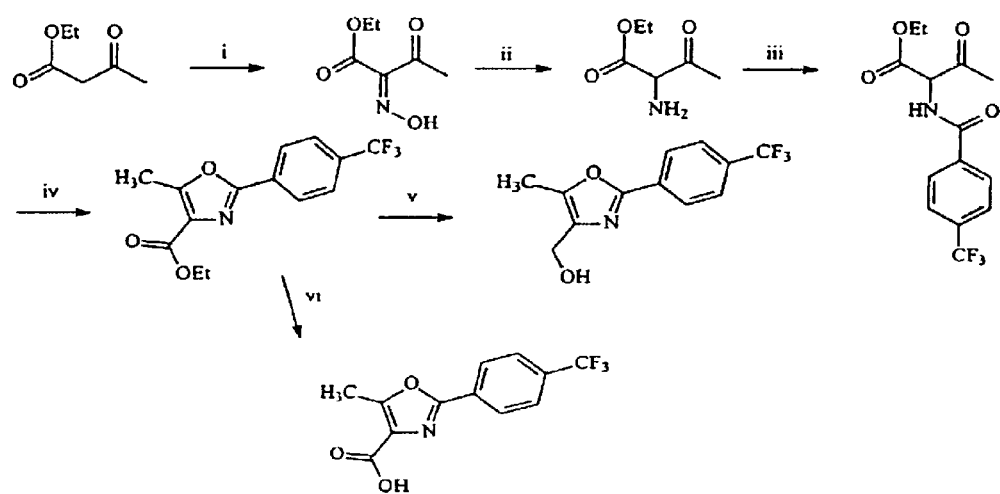
Figure 38:
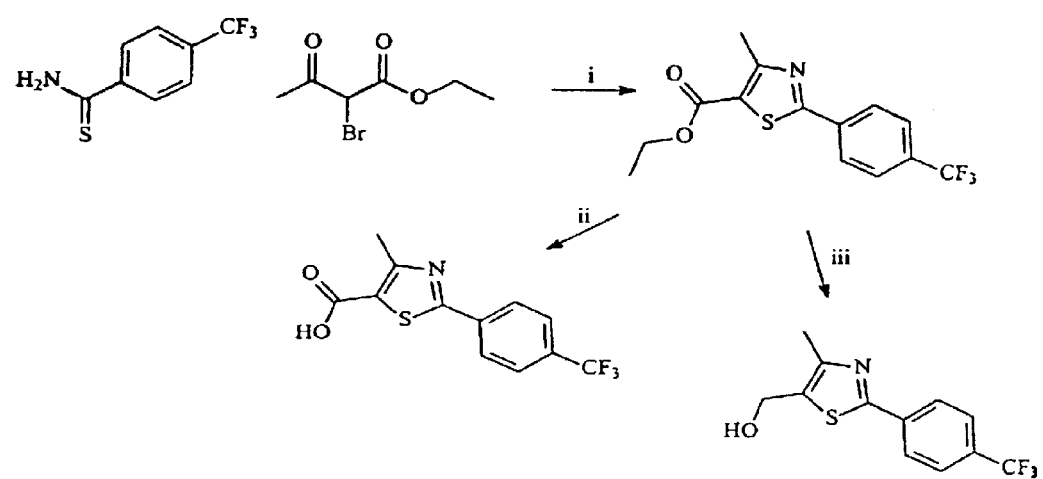

The X—(Y)$_d$—Z group can be synthesized according to procedures that have been published elsewhere, for example in Chao et al. WO 01/00603 A1, in Henke et al., *J. Med. Chem.* (1998) 41:5020–5036, in Collins et al., *J. Med. Chem.* (1998) 41:5037–5054, in Cobb et al., *J. Med. Chem.* (1998) 41:5055–5069, and in Druzgala et al. PCT/US01/13131, each of which is hereby incorporated by reference in its entirety. Some of these procedures are exemplified in FIGS. 36, 37, and 38.

In certain embodiments, the subject invention specifically excludes those compounds taught in: U.S. Pat. Nos. 6,150,371; 6,057,343; 5,939,445; 6,037,359; 6,160,124; 6,248,897; International Application Nos. PCT/US00/18211 (filed Jun. 30, 2000, and having International Publication No. WO 01/02377), PCT/US01/29853 (filed Sep. 21, 2001, and having International Publication No. WO 02/24689), and PCT/US01/13131 (filed Apr. 24, 2001, and having International Publication No. WO 01/81328); EP 0528734 (Adir et Compagnie); EP 0549365 (Sankyo Company Ltd.); EP 0848004 (Shionogi & Co., Ltd.); WO 97/32863 (Torii Pharmaceutical Co.); Japanese Patent Nos. JP9165371 and JP9301963; Kletzien et al. (Molecular Pharmacology, 41(2) 393–398, 1992); Unangst et al. (J. Medicinal Chemistry, 37(2):322–328, 1994); and Sohda et al. (Chemical and Pharmaceutical Bulletin, 30(10):3580–3600, 1982), each of which is hereby incorporated by reference in its entirety, including all figures and formulae).

Also excluded in various embodiments of the invention are those compounds of Formula IA and IB where A is NH; B is sulfur; F is C=O; P and Q are a double bond or hydrogen; E is hydrogen and is attached to each of $D_1$ through $D_6$ or E is a hydrogen atom, tert-butyl, phenyl, iso-propyl group attached to one, or both, of $D_2$ and $D_6$; $D_1$ through $D_6$ are carbon, and X is COOH or OH. Thus, when A is NH; B is sulfur; F is C=O; P and Q are a double bond or hydrogen; E is hydrogen and is attached to each of $D_1$ through $D_6$; and $D_1$ through $D_6$ are carbon, X cannot be COOH or OH. Alternatively, when E is a hydrogen atom or t-butyl group attached to both of $D_2$ and $D_6$, either 1) P and Q cannot be a bond; and/or 2) X cannot be OH.

Also excluded, in some embodiments of the subject invention, from the scope of the invention are 5-[4-[2-(3-trifluoromethylphenyl)-2-(methoxy)ethylaminocarbonyloxy]benzyl]thiazolidin-2,4-dione and 4-(2,4-dioxothiazolidin-5-ylidenemethyl)benzoic acid, 5-(4-hydroxybenzyl)-3-triphenylmethyl-thiazolidine-2,4-dione, 5-(4-acetoxybenzylidene)thiazolidine-2,4-dione, 5-(4-acetoxybenzyl)thiazolidine-2,4-dione, 5-(4-acetoxybenzyl)-3-triphenylmethyl-thiaolidine-2,4-dione, 5-(4-hydroxybenzyl)-3-triphenylmethyl-thiaolidine-2,4-dione, 5-(4-(N-3,4-dichlorophenylcarbamoyl)benzylidene)thiazolidine-2,4-dione, 5-(4-(3,4-dichlorophenoxycarboynyl)benzylidene)thiazolidine-2,4-dione, 5-(4-(3,4-dichlorophenylacetoxy)benylidene)thiazolidine-2,4-dione, and 5-(4-(3,4-dichlorobenzoyloxy)benylidene)thiazolidine-2,4-dione.

Figure 39:
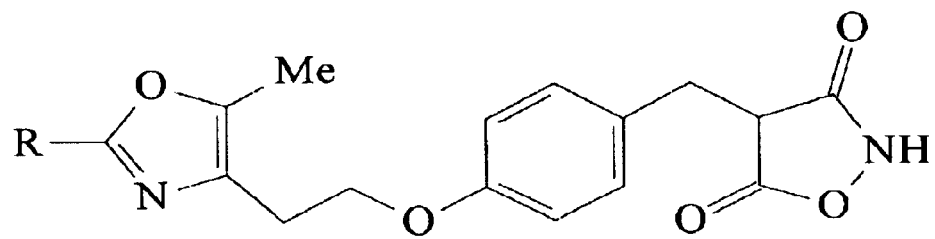
FIGS. 39–40 depict various compounds excluded from the scope of the subject invention.

In certain other embodiments of the invention, compounds exemplified in FIGS. 39–40, are excluded from the scope of the instant invention.

For FIG. 39, substituent groups, and their definitions are set forth as follows. R is an optionally substituted aromatic hydrocarbon group, an optionally substituted alicyclic hydrocarbon group, an optionally substituted heterocyclic group, or an optionally substituted condensed heterocyclic group. The aromatic hydrocarbon group means phenyl, biphenylyl, naphthyl and the like. It may be an aralkyl group such as benzyl. Preferred is phenyl. The alicyclic hydrocarbon group means alicyclic hydrocarbon group having 3 to 7 carbon atoms, and is exemplified by cyclopropyl, cyclobutyl, cyclopentyl, cyclohexyl, cycloheptyl, cyclopropenyl, cyclobutenyl, cyclobutadienyl, cyclopentenyl, cyclopentadienyl, cyclohexenyl, cyclohexadienyl, cycloheptenyl, cycloheptadienyl and the like, with preference given to alicyclic hydrocarbon group having 5 to 7 carbon atoms. Specific examples thereof include cyclopentyl, cyclohexyl, cycloheptyl, cyclopentenyl, cyclopentadienyl, cyclohexenyl, cyclohexadienyl, cycloheptenyl and cycloheptadienyl, with particular preference given to cyclopentyl and cyclohexyl. The heterocyclic group is a 5- or 6-membered heterocycle having, as an atom constituting the ring, 1 to 3, preferably 1 or 2, hetero atoms selected from nitrogen atom, oxygen atom and sulfur atom, besides carbon atom, preferably an aromatic heterocycle. Specific examples thereof include thienyl, furyl, pyrrolyl, imidazolyl, pyrazolyl, thiazolyl, isothiazolyl, oxazolyl, isoxazolyl, oxadiazolyl, thiadiazolyl, triazolyl, pyridyl, pyrazinyl, pyrimidinyl, pyridazinyl, triazinyl, dithiazolyl, dioxolanyl, dithiolyl, pyrrolidinyl, dithiadiazinyl, thiadiazinyl, morpholinyl, oxazinyl, thiazinyl, piperazinyl, piperidinyl, pyranyl and thiopyranyl, with preference given to thienyl, furyl, pyrrolyl, imidazolyl, pyridyl and pyrimidinyl, and particular preference given to pyridyl, pyrimidinyl and imidazolyl. The condensed heterocyclic group is a ring wherein 5- or 6-membered heterocycles having, as an atom constituting the ring, 1 to 3, preferably 1 or 2, hetero atoms selected from nitrogen atom, oxygen atom and sulfur atom, besides carbon atom, preferably aromatic heterocycles have been condensed, or a ring wherein such heterocycle, preferably an aromatic heterocycle, and a 4- to 6-membered aromatic hydrocarbon ring, preferably a benzene ring, have been condensed. Specific examples thereof include furoisoxazolyl, imidazothiazolyl, thienoisothiazolyl, thienothiazolyl, imidazopyrazolyl, cyclopentapyrazolyl, pyrrolopyrrolyl, cyclopentathienyl, thienothienyl, oxadiazolopyrazinyl, benzofurazanyl, thiadiazolopyridinyl, triazolothiazinyl, triazolopyrmidinyl, triazolopyridinyl, benzotriazolyl, oxazolopyrimidinyl, oxazolopyridinyl, benzoxazolyl, thiazolopyridazinyl, thiazolopyrimidinyl, benzisothiazolyl, benzothiazolyl, pyrazolotriazinyl, pyrazolothiazinyl, imidazopyrazinyl, purinyl, pyrazolopyridazinyl, pyrazolopyrimidinyl, imidazopyridinyl, pyranopyrazolyl, benzimidazolyl, indazolyl, benzoxathiolyl, benzodioxolyl, dithiolopyrimidinyl, benzodithiolyl, indolidinyl, indolyl, isoindolyl, furopyrimidinyl, furopyridinyl, benzofuranyl, isobenzofuranyl, thienopyrazinyl, thienopyrimidinyl, thienodioxinyl, thienopyridinyl, benzothienyl, isobenzothienyl, cyclopentaoxazinyl, cyclopentafuranyl, benzothiadiazinyl, benzotriazinyl, pyridoxazinyl, benzoxazinyl, pyrimidothiazinyl, benzothiazinyl, pyrimidopyridazinyl, pyrimidopyrimidinyl, pyridopyridazinyl, pyridopyrimidinyl, cinnolinyl, quinazolinyl, quinoxalinyl, benzoxathiinyl, benzodioxinyl, benzodithiinyl, naphthyridinyl, isoquinolyl, quinolyl, benzopyranyl, benzothiopyranyl, chromanyl, isochromanyl, indolinyl and the like, with preference given to benzoxazolyl, benzisothiazolyl, benzothiazolyl, benzimidazolyl, indazolyl, benzoxathiolyl, benzodioxolyl, benzodithiolyl, indolyl, isoindolyl, benzofuranyl, isobenzofuranyl, benzothienyl, isobenzothienyl, benzothiadiazinyl, benzotriazinyl, benzoxazinyl, benzothiazinyl, cinnolinyl, quinazolinyl, quinoxalinyl, benzoxathiinyl, benzodioxinyl, benzodithiinyl, isoquinolyl, quinolyl, benzopyranyl, benzothiopyranyl, chromanyl, isochromanyl and indolinyl, and particular preference given to indolyl, isoindolyl, benzofuranyl, isobenzofuranyl, benzothienyl, isobenzothienyl, isoquinolyl and quinolyl. The lower alkyl is a linear or branched alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, isohexyl, 3,3-dimethylbutyl, 2,2-dimethylbutyl and the like, with preference given to alkyl having 1 to 4 carbon atoms such as methyl, ethyl, propyl, isopropyl, butyl, isobutyl, sec-butyl and tert-butyl, and particular preference given to methyl. The optionally substituted means that the group may be substituted by 1 to 3 substituents which may be the same or different. Specific examples thereof include lower alkyl such as methyl, ethyl, propyl, butyl, tert-butyl and the like; lower alkoxy such as methoxy, ethoxy, propoxy, butoxy, tert-butoxy and the like; halogen atom; nitro; cyano; hydroxy; acyl (e.g., lower alkanoyl such as formyl, acetyl, propionyl, butyryl, isobutyryl and the like, aroyl such as benzoyl, naphthoyl and the like, and the like); acyloxy (acyl moiety being as defined above) such as formyloxy, acetyloxy, propionyloxy, butyryloxy, isobutyryloxy, benzoyloxy and the like; aralkyloxy such as benzyloxy, phenethyloxy, phenylpropyloxy and the like; mercapto; lower alkylthio such as methylthio, ethylthio, propylthio, butylthio, isobutylthio, tert-butylthio and the like; amino; lower alkylamino such as methylamino, ethylamino, propylamino, isopropylamino, butylamino and the like; di(lower)alkylamino such as dimethylamino, diethylamino, dipropylamino, diisopropylamino, dibutylamino and the like; carboxy; lower alkoxycarbonyl such as methoxycarbonyl, ethoxycarbonyl, propoxycarbonyl, isopropoxycarbonyl, butoxycarbonyl, tert-butoxycarbonyl and the like; acylamino (acyl moiety being as defined above); trifluoromethyl; phosphoryl; sulfonyl; sulfonyloxy; carbamoyl; sulfamoyl; lower alkylphosphonamide such as methylphosphonamide, ethylphosphonamide, propylphosphonamide, isopropylphosphonamide and the like; methylenedioxy; lower alkoxyphosphoryl such as methoxyphosphoryl, ethoxyphosphoryl, propoxyphosphoryl, isopropoxyphosphoryl and the like; lower alkylsulfonyl such as methylsulfonyl, ethylsulfonyl, propylsulfonyl, butylsulfonyl, tert-butylsulfonyl and the like; lower alkylsulfonylamino such as methylsulfonylamino, ethylsulfonylamino, propylsulfonylamino, butylsulfonylamino, tert-butyrylsulfonylamino and the like; and the like, with preference given to hydroxy, lower alkyl, lower alkoxy, aralkyloxy, mercapto, lower alkylthio, nitro, halogen atom, trifluoromethyl, amino, di(lower)alkylamino, lower alkylamino, acyl, cyano, carbamoyl, acyloxy, sulfonyl, carboxy and lower alkoxycarbonyl, and particular preference given to hydroxy, lower alkyl and lower alkoxy. As used herein, by lower is meant that the number of carbon atoms is preferably 1 to 6, more preferably 1 to 4.

Figure 40A:
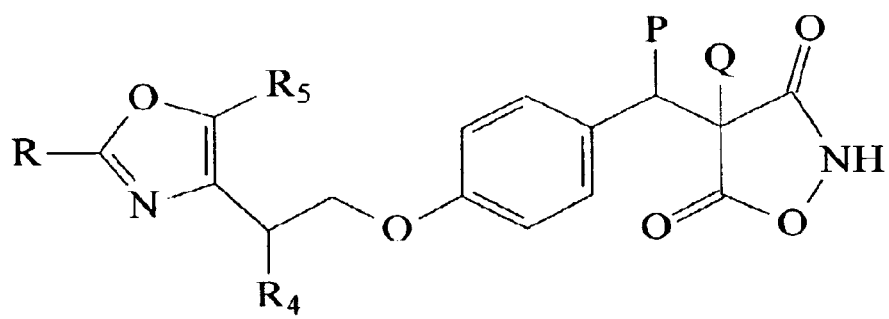
Figure 40B:
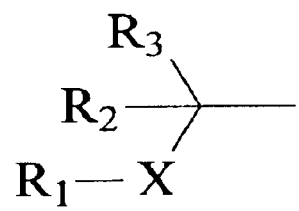

Also excluded, in certain embodiments of this invention, are compounds such as those exemplified in FIGS. 40A and 40B. For such compounds, R is an optionally substituted aromatic hydrocarbon; an optionally substituted alicyclic hydrocarbon; an optionally substituted heterocyclic group; an optionally substituted condensed heterocyclic group; or a group exemplified in FIG. 40B, wherein $R_1$ is an optionally substituted aromatic hydrocarbon, an optionally substituted alicyclic hydrocarbon, an optionally substituted heterocyclic group or an optionally substituted condensed heterocyclic group, $R_2$ and $R_3$ are the same or different and each is a hydrogen atom or a lower alkyl, and X is an oxygen atom, a sulfur atom or a secondary amino; $R_4$ is a hydrogen atom, a lower alkyl or a hydroxy; $R_5$ is a lower alkyl optionally substituted by hydroxy; and P and Q are each a hydrogen atom or P and Q together form a bond, and pharmaceutically acceptable salts thereof. Also excluded, in certain embodiments of the subject invention, are compounds wherein R is an optionally substituted phenyl, an optionally substituted 5- or 6-membered aromatic heterocyclic group having 1 or 2 hetero atoms selected from sulfur atom, oxygen atom and nitrogen atom, or an optionally substituted condensed aromatic heterocyclic group wherein such aromatic heterocyclic ring and a benzene ring are condensed, and pharmaceutically acceptable salts thereof; or where R is a phenyl, a 5- or 6-membered aromatic heterocyclic group having one or two hetero atoms selected from sulfur atom, oxygen atom and nitrogen atom, or a condensed aromatic heterocyclic group wherein such aromatic heterocyclic ring and a benzene ring are condensed, and pharmaceutically acceptable salts thereof; or where R is a phenyl, or a condensed aromatic heterocyclic group wherein a benzene ring and a 5- or 6-membered heterocyclic group having sulfur atom are condensed, and pharmaceutically acceptable salts thereof; or where R is a phenyl, a benzothienyl or 1-methyl-1-(2-pyridylthio)methyl, and pharmaceutically acceptable salts thereof; or where R is a phenyl, and pharmaceutically acceptable salts thereof; or where R is the structure set forth in FIG. 40B, provided that X is a sulfur atom and $R_1$ is an optionally substituted phenyl or an optionally substituted 5- or 6-membered aromatic heterocyclic group having one or two hetero atoms selected from sulfur atom, oxygen atom and nitrogen atom, and pharmaceutically acceptable salts thereof; or $R_1$ is a 5- or 6-membered aromatic heterocyclic group having one or two hetero atoms selected from sulfur atom, oxygen atom and nitrogen atom, and pharmaceutically acceptable salts thereof; or $R_1$ is a 5- or 6-membered aromatic heterocyclic group having nitrogen atom, and pharmaceutically acceptable salts thereof; or $R_1$ is pyridyl, and pharmaceutically acceptable salts thereof.

In certain specific embodiments, isoxazolidinedione derivatives set forth in FIG. 40 and selected from the group of 4-[4-[2-(2-phenyl-5-methyl-4-oxazolyl)ethoxy]benzyl]-3,5-isoxazolidinedione; 4-[4-[2-(2-phenyl-5-methyl-4-oxazolyl)ethoxy]benzylidene]-3,5-isoxazolidine dione; 4-[4-[2-(2-benzothienyl-5-methyl-4-oxazolyl)ethoxy]benzyl]-3,5-isoxazolidinedione; 4-[4-[2-[5-methyl-[2-(2-pyridylthio)ethyl]-4-oxazolyl]ethoxy]benzyl]-3,5-isoxazolidinedione; and pharmaceutically acceptable salts thereof are excluded from the scope of the invention.

EXAMPLES

Example 1

To (S)-2-pyrrolidinemethanol (3.96 g) in THF (30 ml) is added 2-chlorobenzoxazole (5.90 g) also in THF (80 ml) and then, dropwise, triethylamine (3.96 g). Stir at 50° C. for 4 hours. Cool to room temperature and filter out the solid. Evaporate the solvent and dissolve the crude product in 5 ml of methylene chloride. Pass through a silica plug (50 g) in a fritted filter funnel, and elute with methanol/methylene chloride (10:90), applying suction until the product has been collected. The yield of (S)-1-(2-benzoxazolyl)-2-hydroxymethylpyrrolidine is 8.2 g.

Example 2

To (S)-2-pyrrolidinemethanol (3.96 g) in THF (30 ml) is added 2-chlorobenzothiazole (6.50 g) also in THF (80 ml) and then, dropwise, triethylamine (3.96 g). Stir at 50° C. for 4 hours. Cool to room temperature and filter out the solid. Evaporate the solvent and dissolve the crude product in 5 ml of methylene chloride. Pass through a silica plug (50 g) in a fritted filter funnel, and elute with methanol/methylene chloride (10:90), applying suction until the product has been collected. The yield of (S)-1-(2-benzothiazolyl)-2-hydroxymethylpyrrolidine is 8.8 g.

Example 3

To (R)-2-pyrrolidinemethanol (10.1 g) in THF (50 ml) is added 4,5-dimethylthiazole (14.8 g) also in THF (100 ml) and then, dropwise, triethylamine (10.1 g). Stir at 50° C. for 4 hours. Cool to room temperature and filter out the solid. Evaporate the solvent and dissolve the crude product in 10 ml of methylene chloride. Pass through a silica plug (100 g) in a fritted filter funnel, and elute with methanol/methylene chloride (10:90), applying suction until the product has been collected. The yield of (R)-1-(4,5-dimethyl-2-thiazolyl)-2-hydroxymethylpyrrolidine is 19.5 g.

Example 4

2-chloropyridine (12 g) and 2-(methylamino)ethanol (100 ml) are stirred under nitrogen at 120° C. for 18 hours. Cool to room temperature and then pour into iced water (250 ml). Extract with ethyl acetate (2×200 ml). Dry over sodium sulfate. Filter. Evaporate to dryness. The crude product is distilled in vacuo to give 10.3 g of N-methyl-N-(2-pyridinyl)-2-aminoethanol, boiling at 110° C./1.0 mmHg.

Example 5

A solution of 2-chlorobenzoxazole (15.3 g) in THF (100 ml) is added dropwise to an ice-cold solution of 2-(methylamino)ethanol (8.0 g) and triethylamine (10.1 g) also in THF (100 ml). The mixture is stirred at room temperature for 4 hours and the solid is filtered off. The solvent is evaporated and the residue is dissolved in methylene chloride and passed through a silica plug (100 g), eluting with methanol/methylene chloride (10:90) until the product has been collected. The yield of N-methyl-N-(2-benzoxazolyl)-2-aminoethanol is 15.7 g.

Example 6

Thionyl chloride (2.5 ml) was added dropwise to an ice-cold solution of (R)-6-hydroxy-2,5,7,8-tetramethylchroman-2-ylcarbinol (5.1 g) in anhydrous methylene chloride (50 ml). The solution was stirred at 0° C. for 1 hour and then at room temperature for another period of 2 hours. Wash with saturated sodium bicarbonate solution (2×25 ml), then with brine (25 ml), and then with water (25 ml). Dry over sodium sulfate, filter, and evaporate to dryness. The crude product, (R)-6-hydroxy-2,5,7,8-tetramethylchroman-2-ylmethyl chloride (5.2 g) is used as is in the next step.

Example 7

Thionyl chloride (2.5 ml) was added dropwise to an ice-cold solution of (S)-6-hydroxy-2,5,7,8-tetramethylchroman-2-ylcarbinol (5.1 g) in anhydrous methylene chloride (50 ml). The solution was stirred at 0° C. for 1 hour and then at room temperature for another period of 2 hours. Wash with saturated sodium bicarbonate solution (2×25 ml), then with brine (25 ml), and then with water (25 ml). Dry over sodium sulfate, filter, and evaporate to dryness. The crude product, (S)-6-hydroxy-2,5,7,8-tetramethylchroman-2-ylmethyl chloride (5.0 g) is used as is in the next step.

Example 8

A mixture of (R)-6-hydroxy-2,5,7,8-tetramethylchroman-2-ylmethyl chloride (8.43 g), triethylamine (2.6 g), and 2-(methylamino)ethanol (40 ml) is stirred at 120° C. under nitrogen for 16 hours. Cool to room temperature and pour into iced water (100 ml). Extract with ethyl acetate (3×100 ml) and wash the combined organic extracts with brine (100 ml). Dry over sodium sulfate. Filter. Evaporate to dryness. The product, (R)-2-[N-(6-hydroxy-2,5,7,8-tetramethylchroman-2-ylmethyl)-N-methylamino]ethanol weighs 9.0 g.

Example 9

A mixture of (S)-6-hydroxy-2,5,7,8-tetramethylchroman-2-ylmethyl chloride (8.43 g), triethylamine (2.6 g), and 2-(methylamino)ethanol (40 ml) is stirred at 120° C. under nitrogen for 16 hours. Cool to room temperature and pour into iced water (100 ml). Extract with ethyl acetate (3×100 ml) and wash the combined organic extracts with brine (100 ml). Dry over sodium sulfate. Filter. Evaporate to dryness. The product, (S)-2-[N-(6-hydroxy-2,5,7,8-tetramethylchroman-2-ylmethyl)-N-methylamino]ethanol weighs 8.9 g.

Example 10

A mixture of 2-chlorobenzoxazole (3.7 g), (L)-proline methyl ester, hydrochloride salt (4.0 g), and triethylamine (4.9 g) in anhydrous THF (50 ml) is stirred at room temperature for 18 hours. The solid is filtered off and washed with THF (10 ml). The solution is evaporated to dryness and the crude product is dissolved in methylene chloride (5 ml) and passed through a plug of silica (50 g), eluting with ethyl acetate/methylene chloride (10:90). The product, (L)-N-(2-benzoxazolyl)-proline methyl ester (5.0 g) is a crystalline solid.

Example 11

A mixture of 2-chlorobenzoxazole (3.7 g), (D)-proline methyl ester, hydrochloride salt (4.0 g), and triethylamine (4.9 g) in anhydrous THF (50 ml) is stirred at room temperature for 18 hours. The solid is filtered off and washed with THF (10 ml). The solution is evaporated to dryness and the crude product is dissolved in methylene chloride (5 ml) and passed through a plug of silica (50 g), eluting with ethyl acetate/methylene chloride (10:90). The product, (D)—N-(2-benzoxazolyl)-proline methyl ester (5.5 g) is a crystalline solid.

Example 12

(L)-N-(2-benzoxazolyl)-proline methyl ester (5.0 g) is suspended in a mixture consisting of methanol (50 ml), water (5 ml), and lithium hydroxide (0.5 g). Stir for 18 hours at room temperature. Acidify to pH 4.5 with citric acid. Extract with ethyl acetate (4×50 ml). Dry over sodium sulfate, filter, and evaporate to dryness. The product, (L)-N-(2-benzoxazolyl)-proline (4.3 g) is an off-white solid.

Example 13

A mixture of (L)-proline (4.6 g), 2-chlorobenzoxazole (6.6 g), and triethylamine (4.45 g) in anhydrous THF (100 ml) is stirred at reflux temperature for 18 hours. Cool down to room temperature, filter off the solid and wash it with a THF (10 ml). Evaporate the solvent. Add ethyl acetate (50 ml) and then 1N sodium hydroxide (50 ml). Stir for 5 minutes. Keep the aqueous phase. Wash again with ethyl acetate (50 ml). Acidify with citric acid to pH 4.5. Isolate the precipitate by filtration. The aqueous filtrate is extracted with ethyl acetate (4×30 ml). Dry over sodium sulfate. Filter. Evaporate to dryness. The solids are dried in vacuo at 35° C. for 18 hours. The first crop of product weighs 4.77 g. The second crop weighs 3.26 g. The total amount of product, (L)-N-(2-benzoxazolyl)-proline, is 8.03 g.

Example 14

A mixture of (D)-proline (4.6 g), 2-chlorobenzoxazole (6.6 g), and triethylamine (4.45 g) in anhydrous THF (100 ml) is stirred at reflux temperature for 18 hours. Cool down to room temperature, filter off the solid and wash it with a THF (10 ml ). Evaporate the solvent. Add ethyl acetate (50 ml) and then 1N sodium hydroxide (50 ml). Stir for 5 minutes. Keep the aqueous phase. Wash again with ethyl acetate (50 ml). Acidify with citric acid to pH 4.5. Isolate the precipitate by filtration. The aqueous filtrate is extracted with ethyl acetate (4×30 ml). Dry over sodium sulfate. Filter. Evaporate to dryness. The solids are dried in vacuo at 35° C. for 18 hours. The first crop of product weighs 4.93 g. The second crop weighs 2.90 g. The total amount of product, (L)-N-(2-benzoxazolyl)-proline, is 7.83 g.

Example 15

A mixture of 4-hydroxybenzaldehyde (122.12 g), 2,4-thiazolidinedione (117.13 g), piperidine (5.11 g), and benzoic acid (6.11 g) in toluene (1,000 ml), is stirred at 80° C. for 16 hours. Cool to room temperature and filter off the yellow solid. Wash the solid with methylene chloride (3×100 ml) and then with methanol/methylene chloride (30:70) (2×100 ml). Dry in vacuo at 35° C. until constant weight. The yield of product, 5-(4-hydroxybenzylidene)-2,4-thiazolidinedione, is 217.8 g.

Example 16

To p-anisidine (25 g) in acetone (400 ml) at between 0 and 5° C., add dropwise a solution of sodium nitrite (15.41 g) in water (50 ml) and 12N hydrochloric acid (50 ml) from 2 different funnels over a 15-minute period. Stir for another 5 minutes at 0° C. Add methyl acrylate (104.9 g) and then warm up the solution to 35° C. Transfer into a 2-L Erlenmeyer flask and stir vigorously. While stirring, add copper(I) oxide (0.7 g) in several portions. Keep stirring for as long as nitrogen gas evolves from the solution, then stir for another 4 hours. Evaporate the organic solvent and dilute the aqueous residue with water (200 ml). Extract with methylene chloride (200 ml). Dry over sodium sulfate, filter, and evaporate to dryness. The product, methyl 2-chloro-3-(4-methoxyphenyl)propanoate, is a dark oil weighing 42.96 g.

Example 17

Methyl 2-chloro-3-(4-methoxyphenyl)propanoate (31.44 g), thiourea (16.89 g), and anhydrous sodium acetate (11.24 g) in 2-methoxyethanol (100 ml) is stirred at 100° C. for 4 hours. Cool to room temperature and place the flask at 4° C. for 16 hours. The pale yellow solid is filtered off and is washed with hexanes (50 ml). Stir for 30 minutes in ethyl acetate/water (100 ml:10 ml ). Filter. Crystallize from hot ethanol (600 ml). After leaving at 4° C. for 16 hours, the crystals are filtered off and stirred at reflux for 8 hours in a mixture of 2-methoxyethanol (100 ml) and 2N hydrochloric acid (20 ml). Evaporate the solvent. Add ethyl acetate (200 ml) and water (200 ml). Keep the organic phase and wash again with water (200 ml). Dry over sodium sulfate, filter, evaporate to dryness. The product, 5-(4-methoxybenzyl) thiazolidine-2,4-dione (16.7 g) is an oil that solidifies upon standing.

Example 18

To a solution of 5-(4-methoxybenzyl)thiazolidine-2,4-dione (14.3 g) in anhydrous methylene chloride (100 ml) cooled to −40° C., add a 1.0M solution of boron tribromide in methylene chloride (63 ml). The solution is left to warm up to 23° C. and is then stirred for another 16 hours. Pour into iced water (700 ml) and stir for 15 minutes. Isolate the precipitate by filtration. Wash the product with water (50 ml) and then with methylene chloride (50 ml). The yield of 5-(4-hydroxybenzyl)thiazolidine-2,4-dione is 12.8 g.

Example 19

A mixture of methyl 4-formylbenzoate (164.16 g), 2,4-thiazolidinedione (117.13 g), piperidine (5.11 g), and benzoic acid (6.11 g) in toluene (1,000 ml), is stirred at 80° C. for 16 hours. Cool to room temperature and filter off the yellow solid. Wash the solid with methylene chloride (3×100 ml) and then with methanol/methylene chloride (30:70) (2×100 ml). Dry in vacuo at 35° C. until constant weight. The yield of product, 5-(4-carbomethoxybenzylidene)-2,4-thiazolidinedione, is 258.0 g.

Example 20

A suspension of 5-(4-carbomethoxybenzylidene)-2,4-thiazolidinedione (26.3 g) and magnesium turnings (24 g) in anhydrous methanol (300 ml) is stirred at 45° C. for 8 hours. Acidify to pH 5.0 with 6N HCl and then extract with methylene chloride (2×250 ml). Dry over sodium sulfate, filter, and evaporate to dryness. The crude product is chromatographed on silica gel (1,300 g), eluting with methanol/methylene chloride (02:98). The yield of 5-(4-carbomethoxybenzyl)-2,4-thiazolidinedione is 15.2 g.

Example 21

A suspension of 5-(4-carbomethoxybenzylidene)-2,4-thiazolidinedione (50 g) in 6N HCl (200 ml) is stirred at reflux for 4 hours. The mixture is cooled to 4° C. and the product is filtered off. The product is then washed with water (2×100 ml) and is dried in vacuo at 40° C. The yield of 5-(4-carboxybenzylidene)-2,4-thiazolidinedione is 45 g.

Example 22

A suspension of 5-(4-carbomethoxybenzyl)-2,4-thiazolidinedione (50 g) in 6N HCl (200 ml) is stirred at reflux for 4 hours. The mixture is cooled to 4° C. and the product is filtered off. The product is then washed with water (2×100 ml) and is dried in vacuo at 40° C. The yield of 5-(4-carboxybenzyl)-2,4-thiazolidinedione is 44 g.

Example 23

(R)-6-Hydroxy-2,5,7,8-tetramethylchroman-2-carboxylic acid (9.2 g) and 5-(4-hydroxybenzyl)thiazolidine-2,4-dione (8.3 g) are dissolved in methylene chloride (100 ml) and THF (50 ml). To this add dicyclohexylcarbodiimide (7.6 g) and DMAP (0.5 g), and then stir for 4 hours at room temperature. The solid is removed by filtration and is washed with a small amount of THF (20 ml). The solvent is removed and the solid residue is stirred with methylene chloride (100 ml) and left at 4° C. for 16 hours. The product is isolated by filtration and dried in vacuo at 23° C. The yield of 5-{4-[(R)-6-hydroxy-2,5,7,8-tetramethylchroman-2-carboxy]benzyl}thiazolidine-2,4-dione is 12.4 g.

Example 24

(S)-6-Hydroxy-2,5,7,8-tetramethylchroman-2-carboxylic acid (9.2 g) and 5-(4-hydroxybenzyl)thiazolidine-2,4-dione (8.3 g) are dissolved in methylene chloride (100 ml) and THF (50 ml). To this add dicyclohexylcarbodiimide (7.6 g) and DMAP (0.5 g), and then stir for 4 hours at room temperature. The solid is removed by filtration and is washed with a small amount of THF (20 ml). The solvent is removed and the solid residue is stirred with methylene chloride (100 ml) and left at 4° C. for 16 hours. The product is isolated by filtration and dried in vacuo at 23° C. The yield of 5-{4-[(S)-6-hydroxy-2,5,7,8-tetramethylchroman-2-carboxy]benzyl}thiazolidine-2,4-dione is 13.3 g.

Example 25

(R)-6-Hydroxy-2,5,7,8-tetramethylchroman-2-carbinol (1.9 g) and 5-(4-carboxybenzyl)thiazolidine-2,4-dione (1.8 g) are dissolved in methylene chloride (20 ml) and THF (10 ml). To this add dicyclohexylcarbodiimide (1.6 g) and DMAP (0.1 g), and then stir for 4 hours at room temperature. The solid is removed by filtration and is washed with a small amount of THF (5 ml). The solvent is removed and the solid residue is stirred with methylene chloride (20 ml) and left at 4° C. for 16 hours. The product is isolated by filtration and dried in vacuo at 23° C. The yield of 5-{4-[(R)-6-hydroxy-2,5,7,8-tetramethylchroman-2-methoxy]benzyl}thiazolidine-2,4-dione is 2.54 g.

Example 26

(S)-6-Hydroxy-2,5,7,8-tetramethylchroman-2-carbinol (1.9 g) and 5-(4-carboxybenzyl)thiazolidine-2,4-dione (1.8 g) are dissolved in methylene chloride (20 ml) and THF (10 ml ). To this add dicyclohexylcarbodiimide (1.6 g) and DMAP (0.1 g), and then stir for 4 hours at room temperature. The solid is removed by filtration and is washed with a small amount of THF (5 ml). The solvent is removed and the solid residue is stirred with methylene chloride (20 ml) and left at 4° C. for 16 hours. The product is isolated by filtration and dried in vacuo at 23° C. The yield of 5-{4-[(S)-6-hydroxy-2,5,7,8-tetramethylchroman-2-methoxy]benzyl}thiazolidine-2,4-dione is 2.17 g.

Example 27

(R)-6-Hydroxy-2,5,7,8-tetramethylchroman-2-carboxylic acid (4.6 g) and 5-(4-hydroxybenzylidene)thiazolidine-2,4-dione (4.2 g) are dissolved in methylene chloride (50 ml) and THF (25 ml). To this add dicyclohexylcarbodiimide (3.8 g) and DMAP (0.25 g), and then stir for 4 hours at room temperature. The solid is removed by filtration and is washed with a small amount of THF (10 ml ). The solvent is removed and the solid residue is stirred with methylene chloride (50 ml) and left at 4° C. for 16 hours. The product is isolated by filtration and dried in vacuo at 23° C. The yield of 5-{4-[(R)-6-hydroxy-2,5,7,8-tetramethylchroman-2-carboxy]benzylidene}thiazolidine-2,4-dione is 5.9 g.

Example 28

(S)-6-Hydroxy-2,5,7,8-tetramethylchroman-2-carboxylic acid (4.6 g) and 5-(4-hydroxybenzylidene)thiazolidine-2,4-dione (4.2 g) are dissolved in methylene chloride (50 ml) and THF (25 ml). To this add dicyclohexylcarbodiimide (3.8 g) and DMAP (0.25 g), and then stir for 4 hours at room temperature. The solid is removed by filtration and is washed with a small amount of THF (10 ml ). The solvent is removed and the solid residue is stirred with methylene chloride (50 ml) and left at 4° C. for 16 hours. The product is isolated by filtration and dried in vacuo at 23° C. The yield of 5-{4-[(S)-6-hydroxy-2,5,7,8-tetramethylchroman-2-carboxy]benzylidene}thiazolidine-2,4-dione is 6.2 g.

Example 29

(R)-6-Hydroxy-2,5,7,8-tetramethylchroman-2-carbinol (3.8 g) and 5-(4-carboxybenzylidene)thiazolidine-2,4-dione (3.6 g) are dissolved in methylene chloride (40 ml) and THF (20 ml). To this add dicyclohexylcarbodiimide (3.2 g) and DMAP (0.2 g), and then stir for 4 hours at room temperature. The solid is removed by filtration and is washed with a small amount of THF (10 ml ). The solvent is removed and the solid residue is stirred with methylene chloride (40 ml) and left at 4° C. for 16 hours. The product is isolated by filtration and dried in vacuo at 23° C. The yield of 5-{4-[(R)-6-hydroxy-2,5,7,8-tetramethylchroman-2-methoxy]benzylidene}thiazolidine-2,4-dione is 5.4 g.

Example 30

(S)-6-Hydroxy-2,5,7,8-tetramethylchroman-2-carbinol (3.8 g) and 5-(4-carboxybenzylidene)thiazolidine-2,4-dione (3.6 g) are dissolved in methylene chloride (40 ml) and THF (20 ml). To this add dicyclohexylcarbodiimide (3.2 g) and DMAP (0.2 g), and then stir for 4 hours at room temperature. The solid is removed by filtration and is washed with a small amount of THF (10 ml). The solvent is removed and the solid residue is stirred with methylene chloride (40 ml) and left at 4° C. for 16 hours. The product is isolated by filtration and dried in vacuo at 23° C. The yield of 5-{4-[(S)-6-hydroxy-2,5,7,8-tetramethylchroman-2-methoxy]benzylidene}thiazolidine-2,4-dione is 5.2 g.

Example 31

(L)-N-(2-benzoxazolyl)-proline (3.26 g) and 5-(4-hydroxybenzyl)thiazolidine-2,4-dione (3.11 g) are suspended in methylene chloride (100 ml). Add DCC (2.89 g) and DMAP (0.12 g) and stir at room temperature for 4 hours. Filter and purify on 114 g of silica, eluting with methanol/methylene chloride (02:98). The yield of 5-{4-[(S)-1-(2-benzoxazolyl)pyrrolidne-2-carboxy]benzyl}thiazolidine-2,4-dione is 4.55 g.

Example 32

(L)-1-(2-benzoxazolyl)pyrrolidine-2-carbinol (3.26 g) and 5-(4-carboxybenzyl)thiazolidine-2,4-dione (3.25 g) are suspended in methylene chloride (100 ml). Add DCC (2.88 g) and DMAP (0.12 g) and stir at room temperature for 4 hours. Filter and purify on 132 g of silica, eluting with methanol/methylene chloride (02:98). The yield of 5-{4-[(S)-1-(2-benzoxazolyl)pyrrolidinyl-2-methoxycarbonyl]benzyl}thiazolidine-2,4-dione is 4.68 g.

Example 33

(D)-1-(2-benzoxazolyl)pyrrolidine-2-carbinol (3.26 g) and 5-(4-carboxybenzylidene)thiazolidine-2,4-dione (3.35 g) are suspended in methylene chloride (100 ml). Add DCC (2.91 g) and DMAP (0.12 g) and stir at room temperature for 4 hours. Filter and purify on 108 g of silica, eluting with methanol/methylene chloride (02:98). The yield of 5-{4-[(R)-1-(2-benzoxazolyl)pyrrolidinyl-2-methoxycarbonyl]benzylidene}-thiazolidine-2,4-dione is 4.32 g.

Example 34

(D)-1-(2-benzoxazolyl)pyrrolidine-2-carbinol (3.26 g) and 5-(4-carboxybenzyl)thiazolidine-2,4-dione (3.25 g) are suspended in methylene chloride (100 ml). Add DCC (2.93 g) and DMAP (0.12 g) and stir at room temperature for 4 hours. Filter and purify on 162 g of silica, eluting with methanol/methylene chloride (02:98). The yield of 5-{4-[(S)-1-(2-benzoxazolyl)pyrrolidinyl-2-methoxycarbonyl]benzyl}thiazolidine-2,4-dione is 4.77 g.

Example 35

Triethylamine (8.3 ml) is added dropwise to a stirred cold solution of ethyl 2-aminoacetoacetate hydrochloride (5.4 g) and 4-methoxybenzoyl chloride (5.2 g) in dichloromethane (100 ml). After stirring for 3 hours, the solution is washed with water (100 ml), dried over sodium sulfate, filtered, and evaporated to dryness. The crude product, ethyl 2-(4-methoxy)phenylaminoacetoacetate weighs 6.7 g.

Example 36

Ethyl 2-(4-methoxy)phenylaminoacetoacetate (5.9 g) and phosphorus oxychloride (50 ml) are stirred at 100 C. for 30 minutes. The phosphorus oxychloride is removed by evaporation, and the residue is diluted with aqueous sodium bicarbonate and extracted with methylene chloride. After drying over sodium sulfate, the solution is evaporated and the product is crystallized from hexane, giving ethyl 5-methyl-2-(4-methoxy)phenyl-4-oxazolecarboxylate (4.5 g).

Example 37

A solution of benzoyl chloride (17 g) in ethyl acetate (40 ml) is added dropwise, with stirring, in an ice-cold mixture of L-serine methyl ester, hydrochloride (15.5 g), water (100 ml), sodium bicarbonate (21.8 g), and ethyl acetate (100 ml). After stirring for 2 hours, the organic phase is separated, dried over sodium sulfate, and evaporated to give crystalline N-benzoyl-L-serine methyl ester (22.0 g).

Example 38

A stirred mixture of N-benzoyl-L-serine methyl ester (21.0 g), thionyl chloride (21.0 g), and methylene chloride (150 ml) is stirred at reflux for 1 hour. The solvent is evaporated and the residue is diluted with cold water. Neutralize with sodium bicarbonate, and extract with ethyl acetate. Purification on silica gel (250 g), eluting with methanol:methylene chloride (01:99), yields methyl (S)-2-phenyl-2-oxazoline-4-carboxylate (15.2 g).

Example 39

A solution of benzoyl chloride (17 g) in ethyl acetate (40 ml) is added dropwise, with stirring, in an ice-cold mixture of L-threonine methyl ester, hydrochloride (16.5 g), water (100 ml), sodium bicarbonate (21.8 g), and ethyl acetate (100 ml). After stirring for 2 hours, the organic phase is separated, dried over sodium sulfate, and evaporated to give crystalline N-benzoyl-L-threonine methyl ester (21.5 g).

Example 40

A stirred mixture of N-benzoyl-L-threonine methyl ester (21.0 g), thionyl chloride (21.0 g), and methylene chloride (150 ml) is stirred at reflux for 1 hour. The solvent is evaporated and the residue is diluted with cold water. Neutralize with sodium bicarbonate, and extract with ethyl acetate. Purification on silica gel (250 g), eluting with methanol:methylene chloride (01:99), yields methyl (R,S)-2-phenyl-2-oxazoline-5-methyl-4-carboxylate (14.8 g).

Example 41

Figure 21:
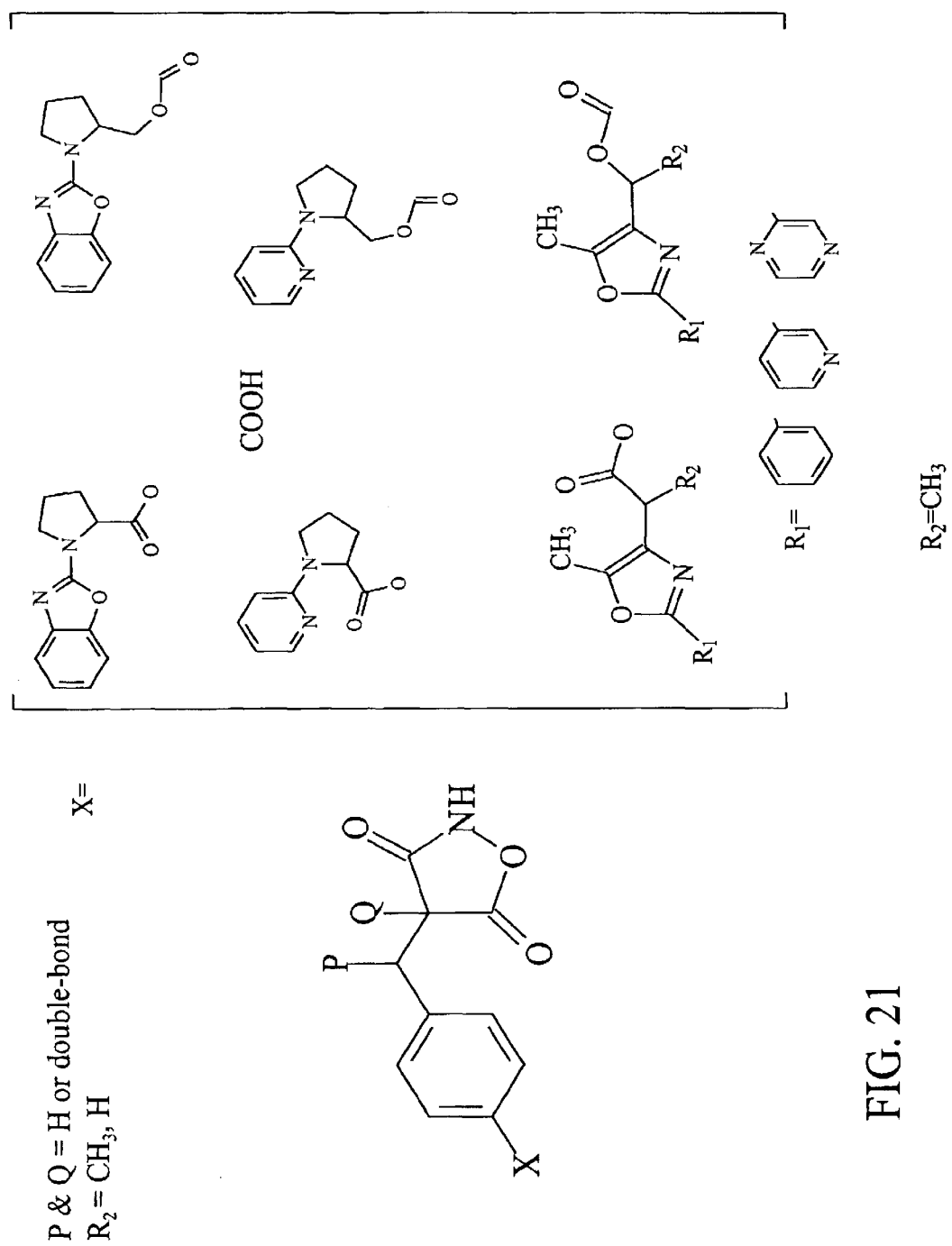
FIG. 21 shows exemplary compounds of Formula IB.
Figure 22:
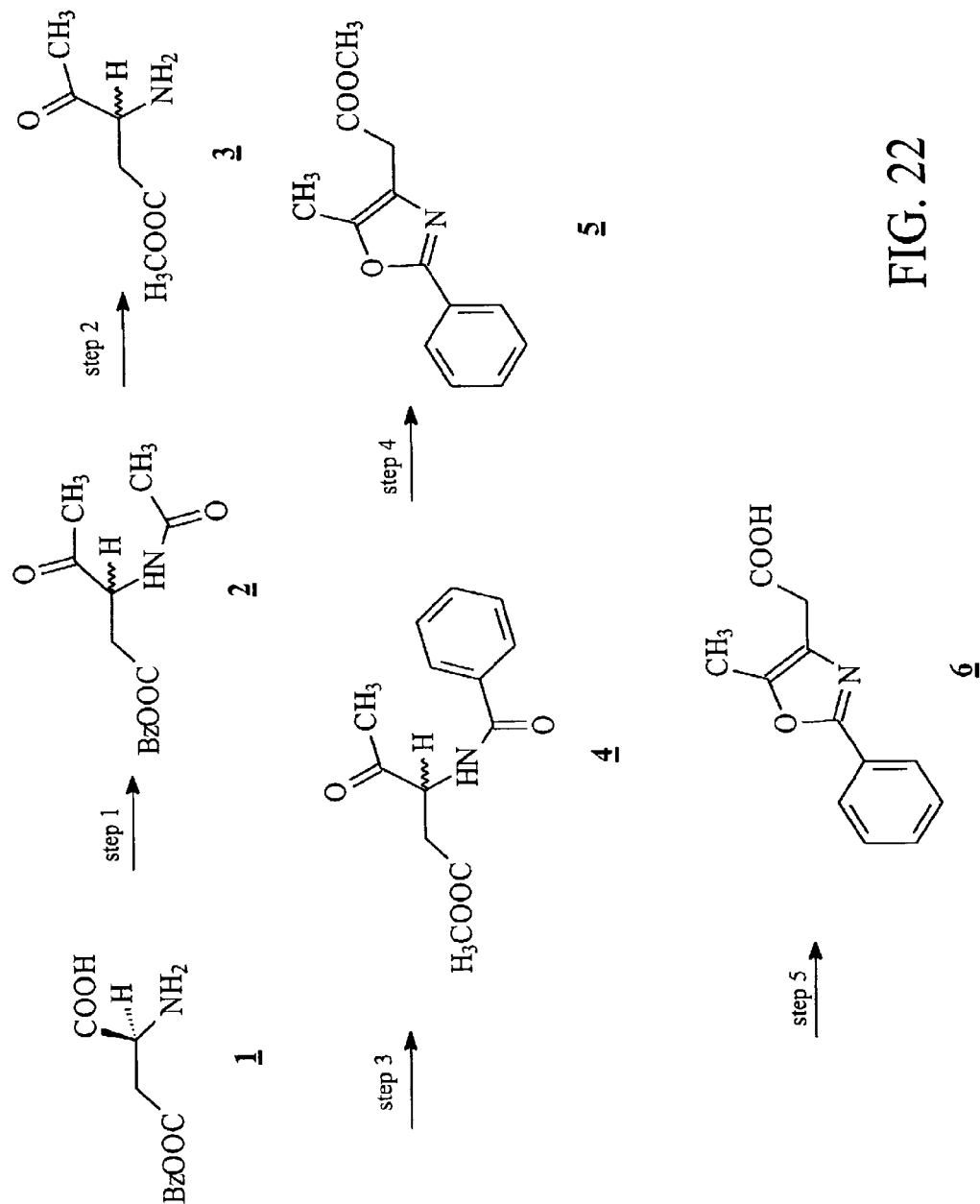
FIGS. 22–28 show exemplary synthesis schemes to produce compounds of Formula IB.
Figure 23:
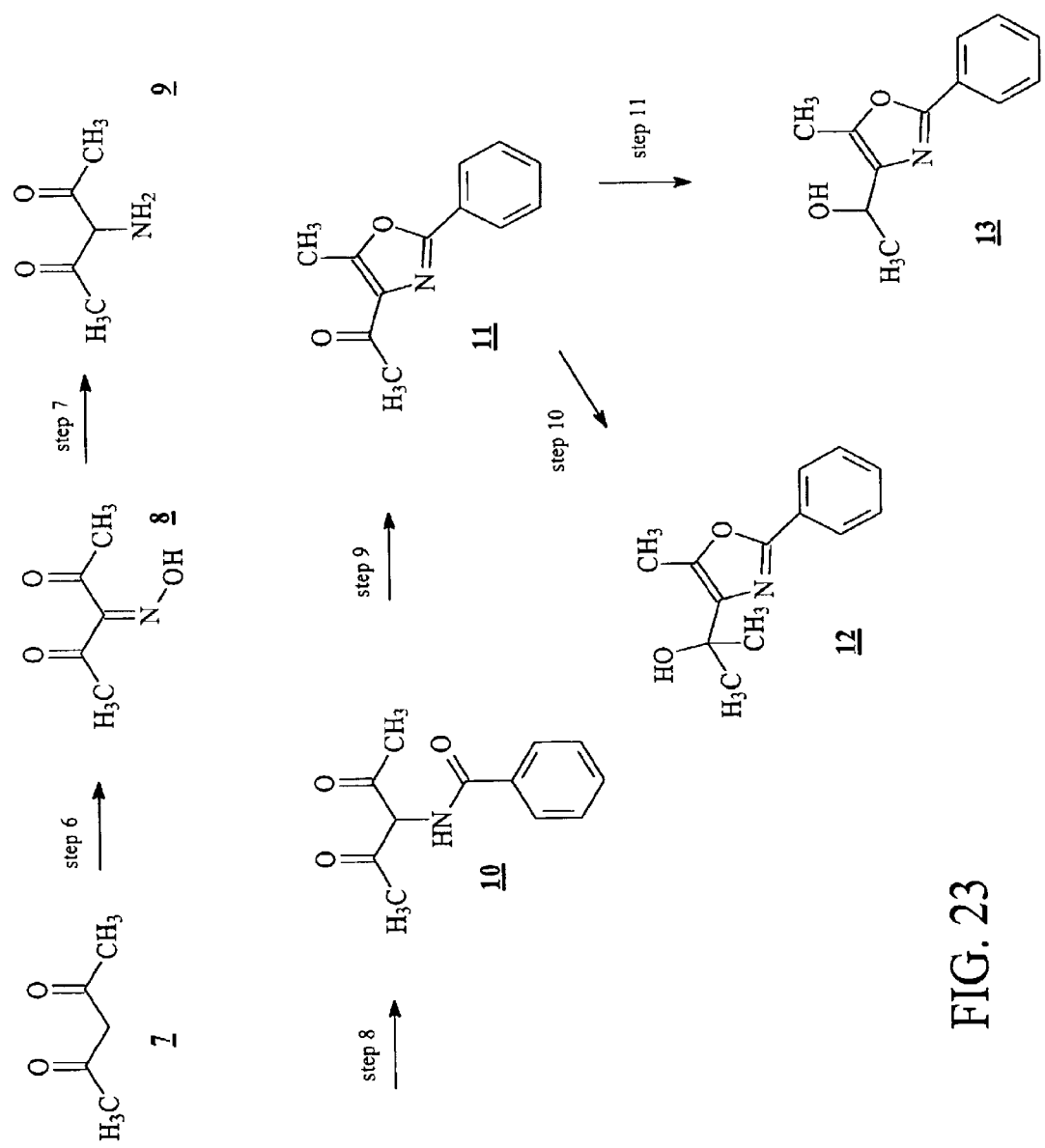
Figure 24:
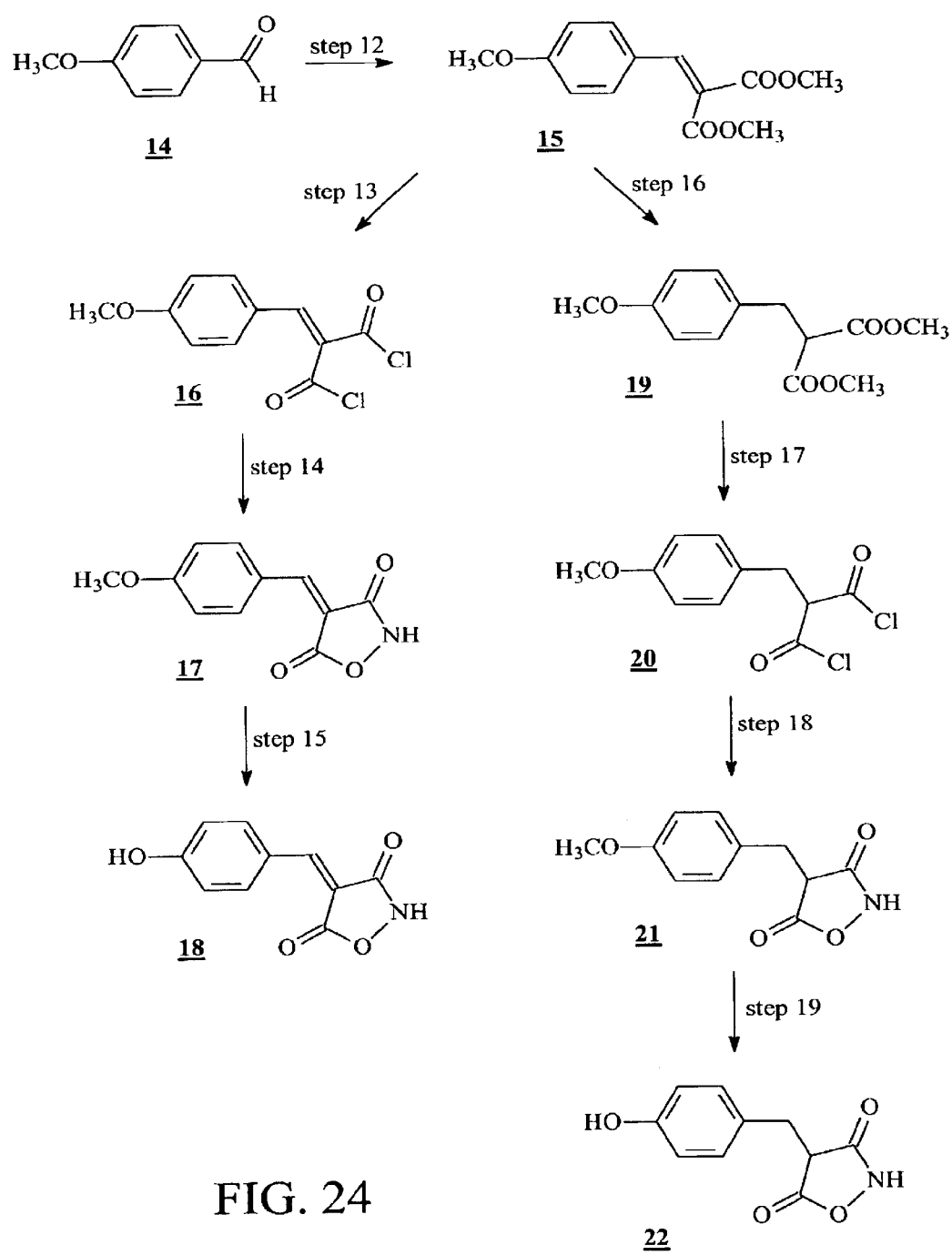
Figure 25:
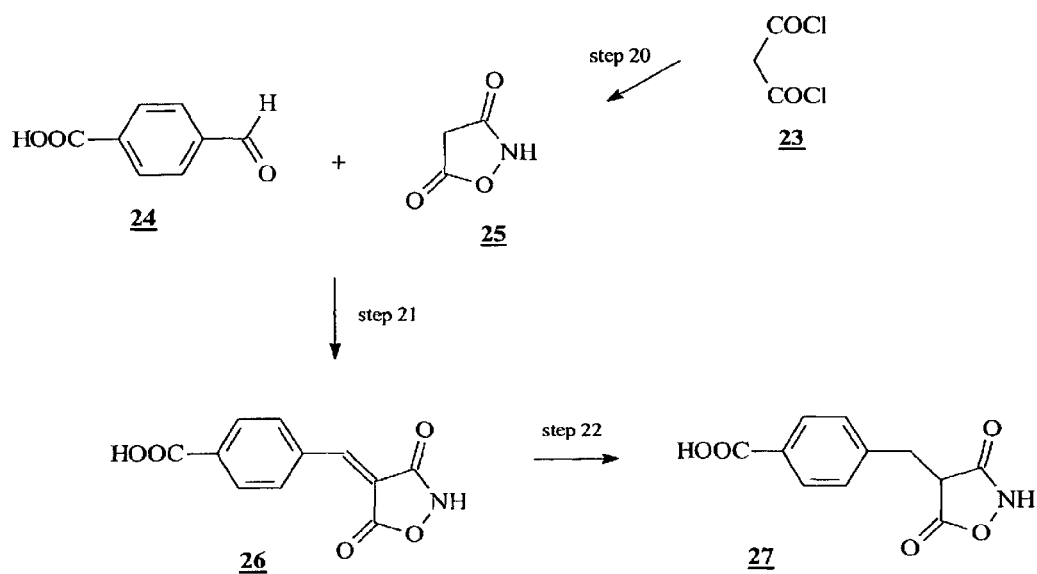
Figure 26:
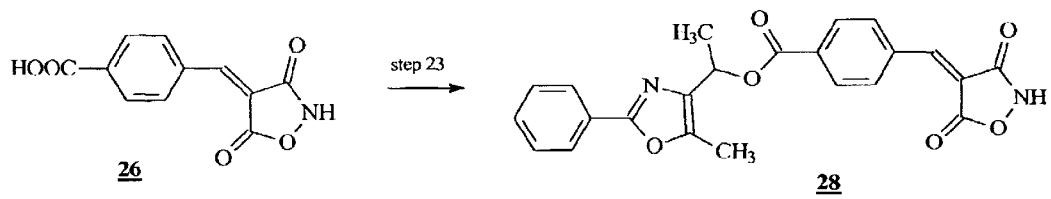
Figure 26:
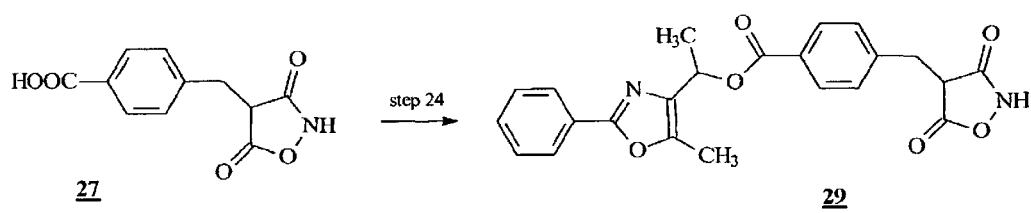
Figure 27:
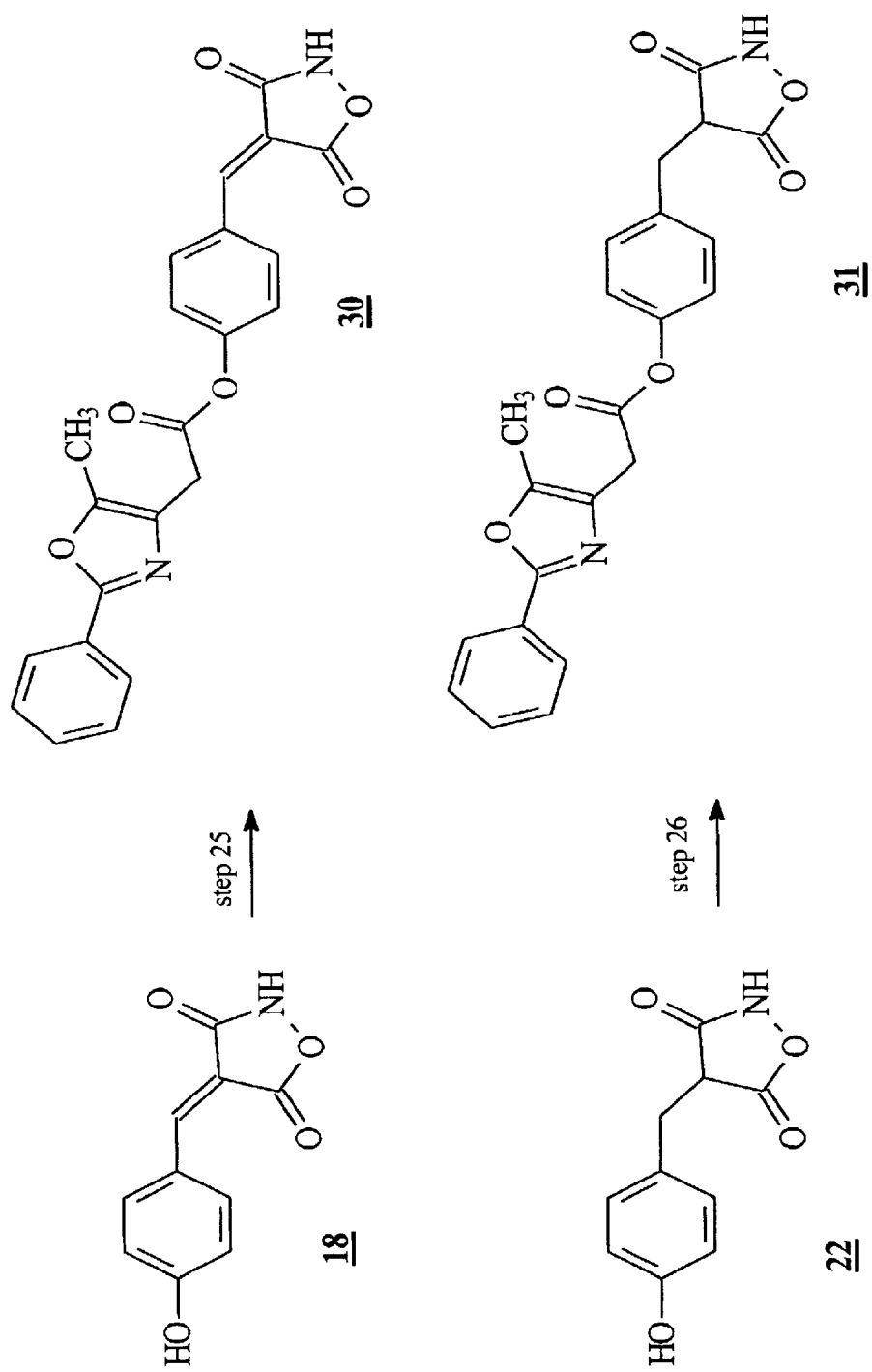
Figure 28:
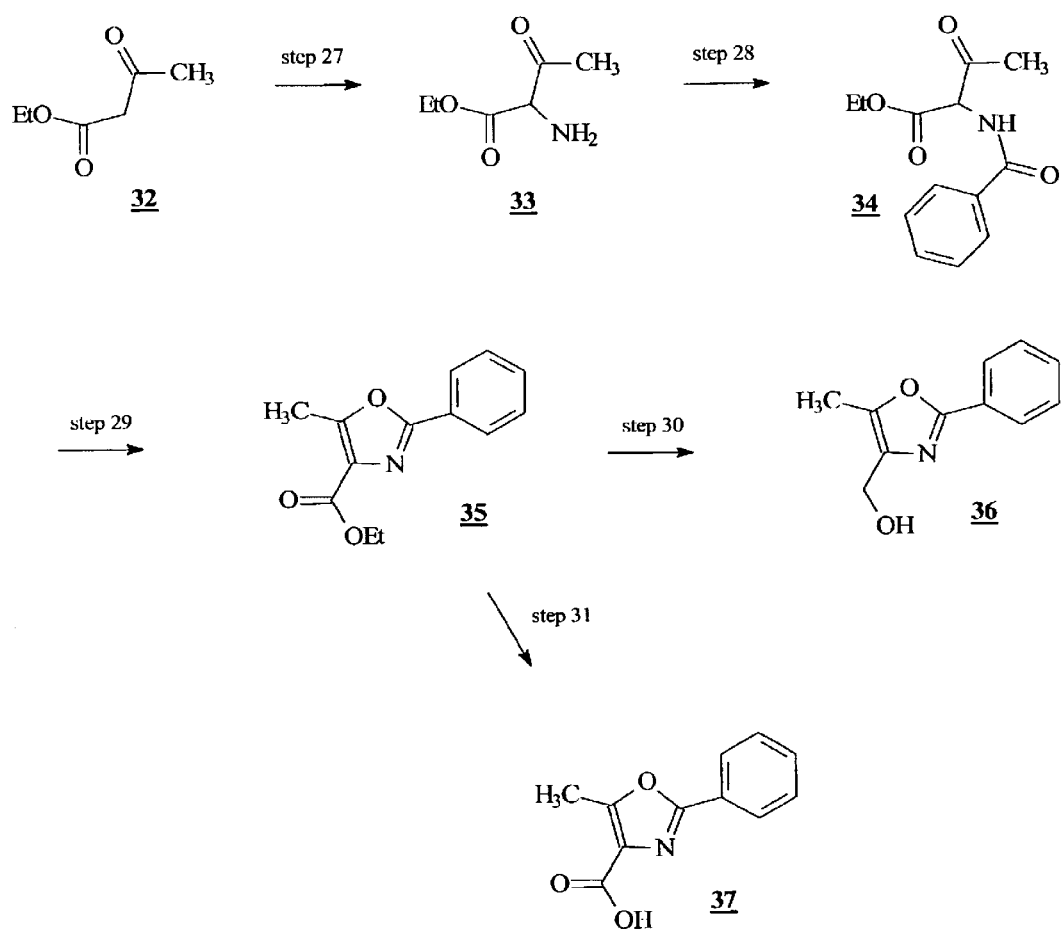

Activity in NIDDM KK-A$^y$ male mice. Non-insulin dependent diabetic mellitus male mice, weighing 50+/-5 g (9–10 weeks of age) were used. These animals exhibited hyperinsulinemia, hyperglycemia, and islet atrophy. The test compounds 105, 115, and 155, and the positive control compound troglitazone were suspended in a 1% carboxymethylcellulose preparation and were given orally at a dose of 10 mg/kg, twice a day, for 5 consecutive days. Blood sampling was performed before the first dose and then 90 minutes after the last dose. Serum glucose and insulin levels were measured. Percent reduction of serum glucose and insulin levels relative to the pre-treatment values are shown in Table XX and FIGS. 20 and 21.

Example 42

CYP Assays

A series of assays to test for activity of 5 principal drug metabolizing enzymes, CYP1A4, CYP2C9, CYP2C19, CYP2D6, and CYP3A4, as well as other CYP450 subfamilies, have been designed and are now commercially available either as ready-to-use kits or as contract work. Commercial sources for these assays include for example Gentest and MDS Panlabs. These assays can test for activity of the enzyme toward metabolism of the test compound as well as testing for kinetic modification (inhibition or activation) of the enzyme by the substrate. These in vitro protocols use simple rapid, low cost methods to characterize aspects of drug metabolism and typically require less than 1 mg of test material.

Example 43

High Throughput Cytochrome P450 Inhibition Screen

The majority of drug-drug interactions are metabolism-based and of these, most involve CYP450. For example, if a new chemical entity is a potent CYP450 inhibitor, it may inhibit the metabolism of a co-administered medication, potentially leading to adverse clinical events. The inhibition of human CYP1A2, CYP2C8, CYP2C9, CYP2C19, CYP2D6, CYP3A4 and other isoforms are assessed using microsomal preparations as enzyme sources and the fluorescence detection method described in the literature (Crespi, C. L., et al. (1997) Microtiter plate assays for inhibition of human, drug-metabolizing cytochromes P450. Anal. Biochem. 248:188–190; Crespi, C. L., et al. (1999) Novel High throughput fluorescent cytochrome P450 assays. Toxicol. Sci. 48, abstr. No.323; Favreau, L. V., et al. (1999) Improved Reliability of the Rapid Microtiter Plate Assay Using Recombinant Enzyme in Predicting CYP2D6 Inhibition in Human Liver Microsomes. Drug Metab. Dispos. 27:436–439). Tests are conducted in 96-well microtiter plates and may use the following fluorescent CYP450 substrates: resorufin benzyl ether (BzRes), 3-cyano-7-ethoxycoumarin (CEC), ethoxyresorufin (ER), 7-methoxy-4-trifluoromethylcoumarin (MFC), 3-[2-(N,N-diethyl-N-methylamino)ethyl]-7-methoxy-4-methylcoumarin (AMMC), 7-benzyloxyquinoline (BQ), dibenzyfluorescein (DBF) or 7-benzyloxy-4-trifluoromethylcoumarin (BFC). Multiple CYP3A4 substrates are available to assess substrate dependence of $IC_{50}$ values, activation and the complex inhibition kinetics associated with this enzyme (Korzekwa, K. R., et al. (1998). Evaluation of atypical cytochrome P450 kinetics with two-substrate models: evidence that multiple substrates can simultaneously bind to the cytochrome P450 active sites. Biochemistry., 37, 4137–4147; Crespi, C. L. (1999) Higher-throughput screening with human cytochromes P450. Curr. Op. Drug Discov. Dev.2: 15–19). Data are reported as $IC_{50}$ values or percent inhibition when using only one or two concentrations of test compound.

Example 44

Metabolic Stability

Metabolic stability influences both oral bioavailability and half-life; compounds of higher metabolic stability are less controllable in their pharmacokinetic parameters. This combination of characteristics, or properties, leads to potential DDI and liver toxicity. This test measures the metabolic stability of the compound in the presence of CYP450, in the presence of hydrolytic enzymes, and in the presence of both CYP450 and hydrolytic enzymes.

Stability in the presence of CYP450: With CYP450 substrates of low and moderate in vivo clearance, there is a good correlation between in vitro metabolic stability and in vivo clearance (Houston, J. B. (1994) Utility of in vitro drug metabolism data in predicting in vivo metabolic clearance). This test uses pooled liver microsomes, S9 (human and/or preclinical species) or microsomal preparations with appropriate positive and negative controls. Assessment of both phase-I and phase-II enzymatic metabolism is possible, and a standard set of substrate concentrations and incubations may be used. Metabolism is measured by loss of parent compound HPLC analysis with absorbance, fluorescence, radiometric or mass spectrometric detection can be used.

Stability in the presence of hydrolytic enzymes: Hydrolytic enzymes in liver cytosol, plasma, or enzymatic mixes from commercial sources (human and/or preclinical species) are used to assess the metabolic stability of the novel compounds of the invention. Appropriate positive and negative controls, as well as a standard set of substrate concentrations, are added in order to correlate in vitro observations with in vivo metabolic half-life. Metabolism is measured by loss of parent compound. HPLC analysis with absorbance, fluorescence, radiometric or mass spectrometric detection can also be used.

Stability in the presence of both CYP450 and hydrolytic enzymes: This test uses pooled liver microsomes, S9 (human and/or preclinical species) or microsomal preparations with appropriate positive and negative controls, combined with hydrolytic enzymes from commercial sources, plasma, or cytosol to assess metabolic stability. The test can also be performed in primary hepatocytes (human and/or preclinical species) or in perfused liver (preclinical species). The use of positive and negative controls, as well as a standard set of substrates allow for correlations between in vitro observations and in vivo metabolic half-life.

Example 45

CYP1A1 Induction Screening

Induction of CYP1A1 is indicative of ligand activation of the aryl hydrocarbon (Ah) receptor, a process associated with induction of a variety of phase-I and phase-II enzymes (Swanson, H. I. (1993) The AH-receptor: genetics, structure and function. Pharmacogenetics 3:213–230). Many pharmaceutical companies choose to avoid development of compounds suspected as Ah-receptor ligands. This test uses a human lymphoblastoid cell line containing native CYP1A1 activity that is elevated by exposure to Ah receptor ligands. Assays are conducted in 96-well microtiter plates using an overnight incubation with the test substances, followed by addition of 7-ethoxy-4-trifluoromethylcoumarin as substrate. Dibenz(a,h)anthracene is used as a positive control inducer. A concurrent control test for toxicity or CYP1A1 inhibition is available using another cell line that constitutively expresses CYP1A1.

Example 46

Cytochrome P450 Reaction Phenotyping

The number and identity of CYP450 enzymes responsible for the metabolism of a drug affects population variability in metabolism. Reaction phenotyping uses either liver microsomes with selective inhibitors or a panel of cDNA-expressed enzymes to provide a preliminary indication of the number and identity of enzymes involved in the metabolism of the substrate. The amount of each cDNA-expressed enzyme is chosen to be proportional to the activity of the same enzyme in pooled human liver microsomes. Protein concentration is standardized by the addition of control microsomes (without CYP450 enzymes). A standard set of substrate concentrations and incubations is used and metabolism of the drug is measured by loss of parent compound. Alternatively, HPLC analysis with absorbance, fluorescence, radiometric or mass spectrometric detection can be used.

Example 47

Drug Permeability Measurement in Caco-2, LLC-PK1 or MDCK Cell Monolayers

Drug permeability through cell monolayers correlates well with intestinal permeability and oral bioavailability. Several mammalian cell lines are appropriate for this measurement (Stewart, B. H., et al. (1995) Comparison of intestinal permeabilities determined in multiple in vitro and in situ models: relationship to absorption in humans. Pharm. Res. 12:693–699; Irvine, J. D., et al. (1999). MDCK (Madin-Darby Canine Kidney) cells: A tool for membrane permeability screening. J. Pharm. Sci. 88:28–33). Apical to basolateral diffusion is measured using a standard set of time points and drug concentrations. These systems can be adapted to a high throughput mode. Liquid chromatography/mass spectroscopy (LC/MS) analysis is also available for analysis of metabolites. Controls for membrane integrity and comparator compounds are included and data are reported as apparent permeability ($P_{app}$) or percent flux under fixed conditions.

Example 48

Human P-glycoprotein (PGP) Screen

An ATPase assay is used to determine if the compounds interact with the xenobiotic transporter MDR1 (PGP). ATP hydrolysis is required for drug efflux by PGP, and the ATPase assay measures the phosphate liberated from drug-stimulated ATP hydrolysis in human PGP membranes. The assay screens compounds in a high throughput mode using single concentration determinations compared to the ATPase activity of a known PGP substrate. A more detailed approach by determining the concentration-dependence and apparent kinetic parameters of the drug-stimulated ATPase activity, or inhibitory interaction with PGP can also be used.

Example 49

PGP-Mediated Drug Transport in Polarized Cell Monolayers

P-glycoprotein (PGP) is a member of the ABC transporter superfamily and is expressed in the human intestine, liver and other tissues. Localized to the cell membrane, PGP functions as an ATP-dependent efflux pump, capable of transporting many structurally unrelated xenobiotics out of cells. Intestinal expression of PGP may affect the oral bioavailability of drug molecules that are substrates for this transporter. Compounds that are PGP substrates can be identified by direct measurement of their transport across polarized cell monolayers. Two-directional drug transport (apical to basolateral permeability, and basolateral to apical PGP-facilitated efflux) can be measured in LLC-PK1 cells (expressing human PGP cDNA) and in corresponding control cells. Caco-2 cells can also be used. Concentration-dependence is analyzed for saturation of PGP-mediated transport, and apparent kinetic parameters are calculated. Test compounds can also be screened in a higher throughput mode using this model. LC/MS analysis is available. Controls for membrane integrity and comparator compounds are included in the assay system.

Example 50

Protein Binding

LC/MS analysis can be used to assess the affinity of the test compound for immobilized human serum albumin (Tiller, P. R., et al. (1995) Immobilized human serum albumin: Liquid chromatography/mass spectrometry as a method of determining drug-protein binding. Rapid comm. mass spectrom. 9:261–263). Appropriate low, medium and high binding positive control comparators are included in the test.

Example 51

Metabolite Production

Milligram quantities of metabolites can be produced using microsomal preparations or cell lines. These metabolites can be used as analytical standards, an aid in structural characterization, or as material for toxicity and efficacy testing.

Example 52

Effect on Herg Channel

This assay tests the effect of parent drugs and metabolite (s) on Herg channels using either a cloned Herg channel expressed in stable human embryonic kidney cells (HEK), or Chinese hamster ovary cells (CHO) transiently expressing the Herg/MiRP-1-encoded potassium channel. Whole cell experiments are carried out by means of the patch-clamp technique and performed in the voltage-clamp mode.

In the test using HEK cells, cells are depolarized from the holding potential of −80 mV to voltages between −80 and +60 mV in 10 mV increments for 4 seconds in order to fully open and inactivate the channels. The voltage is then stepped back to −50 mV for 6 seconds in order to record the tail current. The current is also recorded in the presence of test compounds in order to evaluate a dose-response curve of the ability of a test compound to inhibit the Herg channel.

In the test involving CHO cells, the cells are clamped at a holding potential of −60 mV in order to establish the whole-cell configuration. The cells are then depolarized to +40 mV for 1 second and afterwards hyper-/depolarized to potentials between −120 and +20 mV in 20 mV increments for 300 mSec in order to analyze the tail currents. To investigate the effects of test compounds, the cells are depolarized for 300 mSec to +40 mV and then repolarized to −60 mV at a rate of 0.5 mV/mSec, followed by a 200-mSec test potential to −120 mV. After 6 control stimulations, the extracellular solution is changed to a solution containing the test compound, and 44 additional stimulations are then performed. The peaks of the outward currents and inward tail currents are analyzed.

Activity on HERG channel can also be assessed using a perfused heart preparation, usually guinea pig heart or other small animal. In this assay the heart is paced and perfused with a solution containing a known concentration of the drug. A concentration-response curve of the effects of drug on QT interval is then recorded and compared to a blank preparation in which the perfusate does not contain the drug.

Example 53

Toxicity in Hepatocyte Cell Culture

This test is performed in primary human and porcine hepatocyte cultures. Toxicity is determined by the measurement of total protein synthesis by pulse-labeling with [$^{14}$C] leucine (Kostrubsky, V. E., et al. (1997) Effect of taxol on cytochrome P450 3A and acetaminophen toxicity in cultured rat hepatocytes: Comparison to dexamethasone. Toxicol. Appl. Pharmacol. 142:79–86), and by reduction of 3-(4,5-dimethylthiazol-2-yl)-2,5-diphenyltetrazolium bromide using a protocol described by the manufacturer (Sigma Chemical Co., St. Louis, Mo.). Hepatocytes can be isolated from livers not used for whole organ transplants or from male Hanford miniature pigs.

It should be understood that the reaction schemes and embodiments described herein are for illustrative purposes only and that various modifications or changes in light thereof will be suggested to persons skilled in the art and are to be included within the spirit and purview of this application and the scope of the appended claims.

TABLE I

Formula I

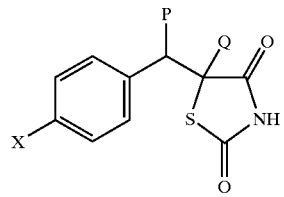

| Compound number | X | P and Q* |
|---|---|---|
| 1 | | H |
| 2 | HO— | db |
| 3 | O=, HO— | H |
| 4 | O=, HO— | db |
| 5 | cyclohexyl-C(CH₃)(C(O)O—) | H |
| 6 | cyclohexyl-C(CH₃)(C(O)O—) | db |

TABLE I-continued

Formula I

[Structure: 4-X-phenyl-CH(P)-thiazolidine-2,4-dione with Q at 5-position]

| Compound number | X | P and Q* |
|---|---|---|
| 7<br>8 | [5-ethylpyridin-2-yl methyl acetate group] | H<br>db |
| 9<br>10 | [6-hydroxy-2,5,7,8-tetramethylchroman-2-yl methyl carboxylate] | H<br>db |
| 11<br>12 | [6-hydroxy-2,5,7,8-tetramethylchroman-2-yl methyl carboxylate, alternate stereochem] | H<br>db |
| 13<br>14 | [5-hydroxy-2,2,4,6,7-pentamethyl-2,3-dihydrobenzofuran-3-yl methyl carboxylate] | H<br>db |
| 15<br>16 | [5-hydroxy-2,2,4,6,7-pentamethyl-2,3-dihydrobenzofuran-3-yl methyl carboxylate, alternate stereochem] | H<br>db |
| 17<br>18 | [(1-methylcyclohexyl)methyl ester group] | H<br>db |
| 19<br>20 | [(1-methylcyclohexyl) ester group] | H<br>db |
| 21<br>22 | [2-(5-ethylpyridin-2-yl)ethyl ester group] | H<br>db |
| 23<br>24 | [(5-ethylpyridin-2-yl)methyl ester group] | H<br>db |
| 25<br>26 | [(6-hydroxy-2,5,7,8-tetramethylchroman-2-yl)methyl ester] | H<br>db |
| 27<br>28 | [(6-hydroxy-2,5,7,8-tetramethylchroman-2-yl)methyl ester, alternate stereochem] | H<br>db |
| 29<br>30 | [(5-hydroxy-2,2,4,6,7-pentamethyl-2,3-dihydrobenzofuran-3-yl)methyl ester] | H<br>db |

TABLE I-continued
Formula I
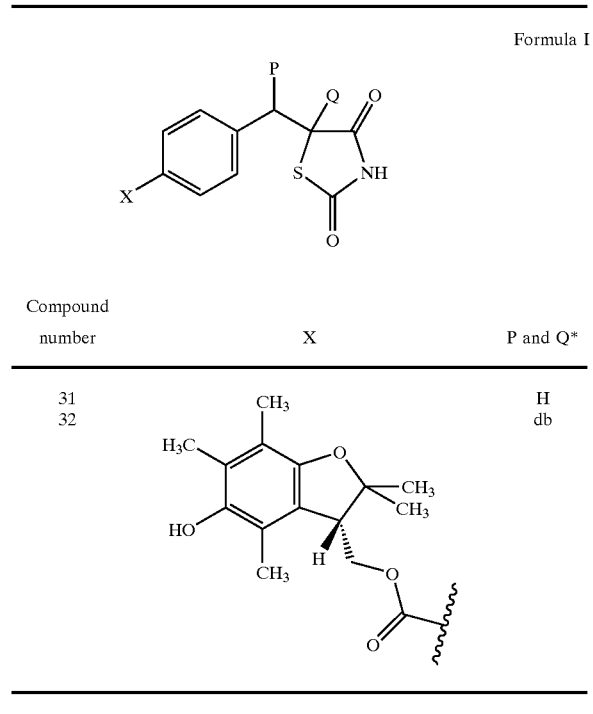
| Compound number | X | P and Q* |
|---|---|---|
| 31 32 | (chroman-like structure shown) | H db |
TABLE II
Formula II
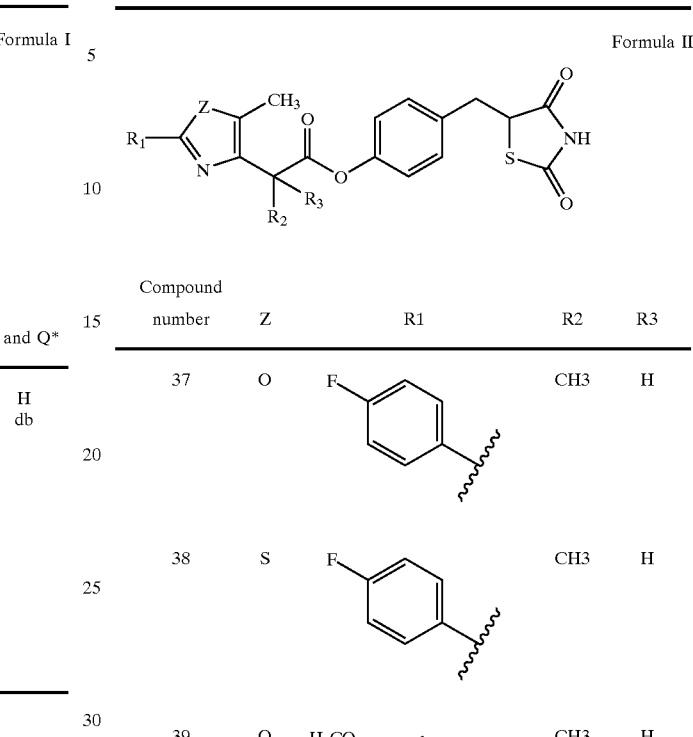
| Compound number | Z | R1 | R2 | R3 |
|---|---|---|---|---|
| 33 | O | phenyl | H | H |
| 34 | O | phenyl | CH3 | H |
| 35 | O | phenyl | CH3 | CH3 |
| 36 | S | phenyl | CH3 | H |
TABLE II-continued
Formula II
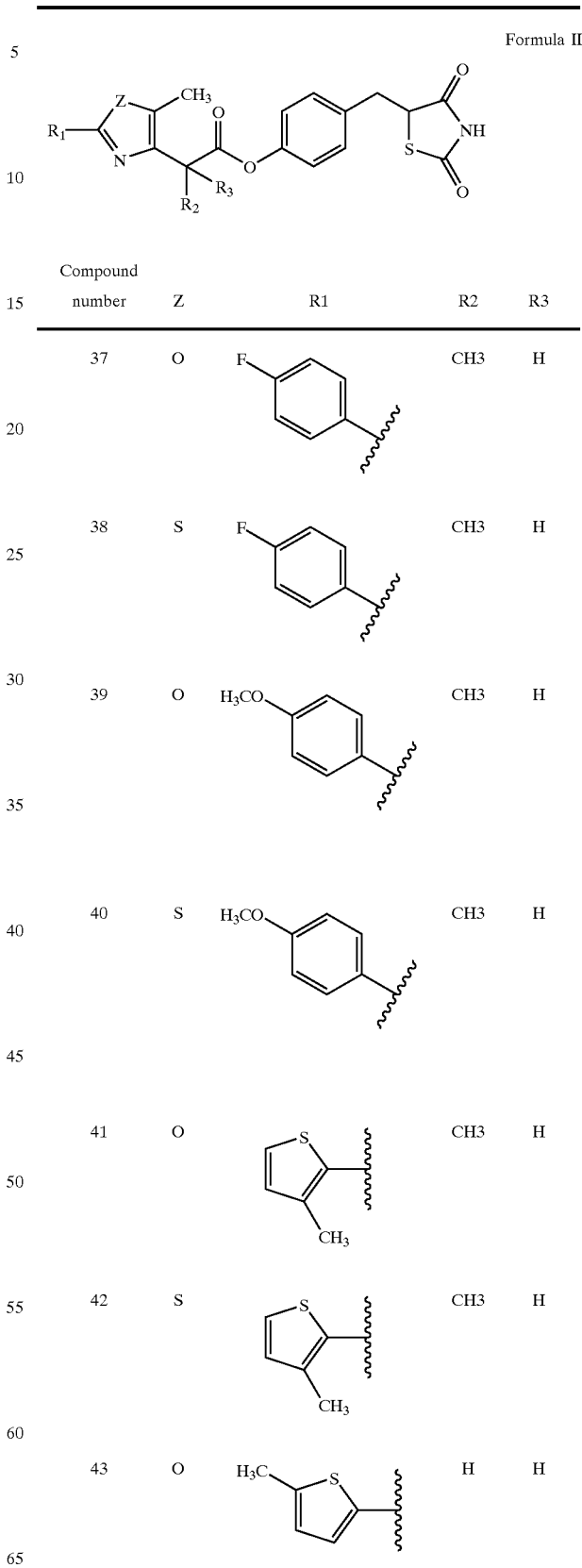
| Compound number | Z | R1 | R2 | R3 |
|---|---|---|---|---|
| 37 | O | 4-F-phenyl | CH3 | H |
| 38 | S | 4-F-phenyl | CH3 | H |
| 39 | O | 4-H3CO-phenyl | CH3 | H |
| 40 | S | 4-H3CO-phenyl | CH3 | H |
| 41 | O | 3-methylthiophen-2-yl | CH3 | H |
| 42 | S | 3-methylthiophen-2-yl | CH3 | H |
| 43 | O | 5-methylthiophen-2-yl | H | H |

TABLE II-continued

Formula II

[Structure: R1-thiazole/oxazole with CH3, connected via C(R2)(R3)-C(=O)-O- to benzyl-thiazolidine-2,4-dione]

| Compound number | Z | R1 | R2 | R3 |
|---|---|---|---|---|
| 44 | O | H3C-thiophen-2-yl | CH3 | H |
| 45 | S | H3C-thiophen-2-yl | H | H |
| 46 | O | 5-methyl-isoxazol-3-yl | CH3 | H |
| 47 | S | 5-methyl-isoxazol-3-yl | H | H |
| 48 | O | pyridin-2-yl | CH3 | H |
| 49 | O | pyridin-4-yl | CH3 | H |
| 50 | O | pyrazin-2-yl | CH3 | H |

TABLE III

[Structure: R1-thiazole/oxazole with CH3, connected via C(R2)(R3)-C(=O)-O- to benzylidene-thiazolidine-2,4-dione]

| Compound number | Z | R1 | R2 | R3 |
|---|---|---|---|---|
| 51 | O | phenyl | H | H |
| 52 | O | phenyl | CH3 | H |
| 53 | O | phenyl | CH3 | CH3 |
| 54 | S | phenyl | CH3 | H |
| 55 | O | 4-F-phenyl | CH3 | H |
| 56 | S | 4-F-phenyl | CH3 | H |
| 57 | O | 4-H3CO-phenyl | CH3 | H |
| 58 | S | 4-H3CO-phenyl | CH3 | H |
| 59 | O | 3-methyl-thiophen-2-yl | CH3 | H |

TABLE III-continued

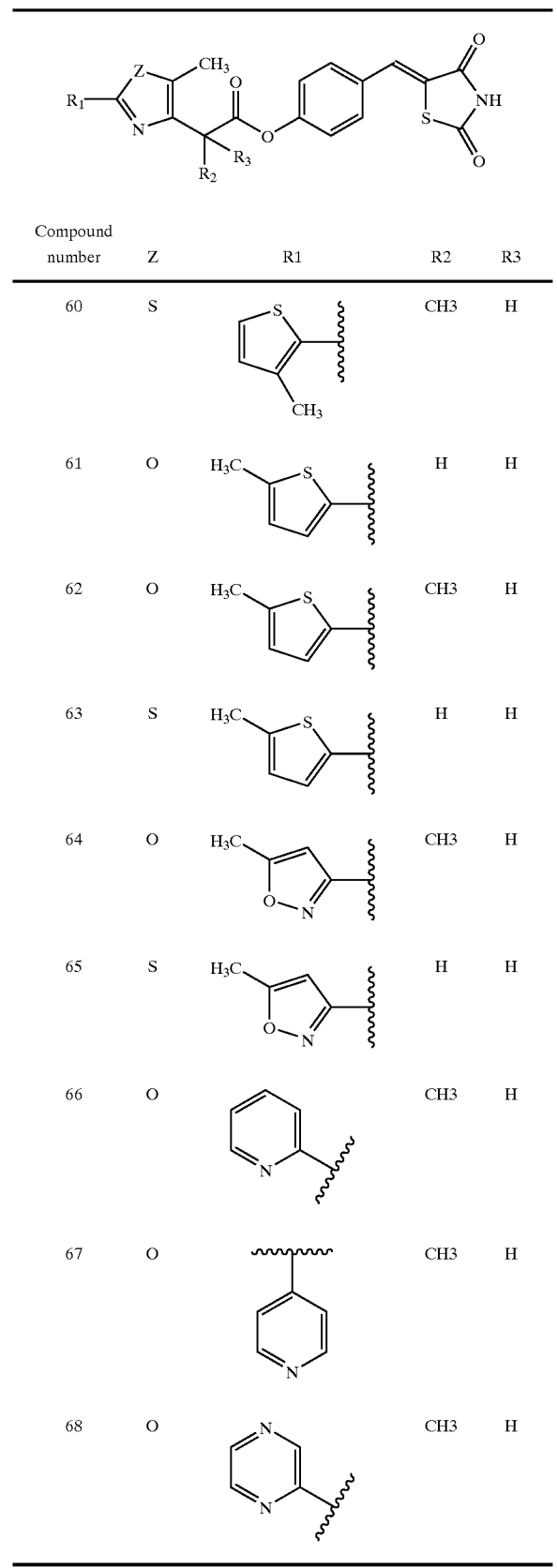

| Compound number | Z | R1 | R2 | R3 |
|---|---|---|---|---|
| 60 | S | 3-methyl-thiophen-2-yl | CH3 | H |
| 61 | O | 5-methyl-thiophen-2-yl | H | H |
| 62 | O | 5-methyl-thiophen-2-yl | CH3 | H |
| 63 | S | 5-methyl-thiophen-2-yl | H | H |
| 64 | O | 5-methyl-isoxazol-3-yl | CH3 | H |
| 65 | S | 5-methyl-isoxazol-3-yl | H | H |
| 66 | O | pyridin-2-yl | CH3 | H |
| 67 | O | pyridin-4-yl | CH3 | H |
| 68 | O | pyrazin-2-yl | CH3 | H |

TABLE IV

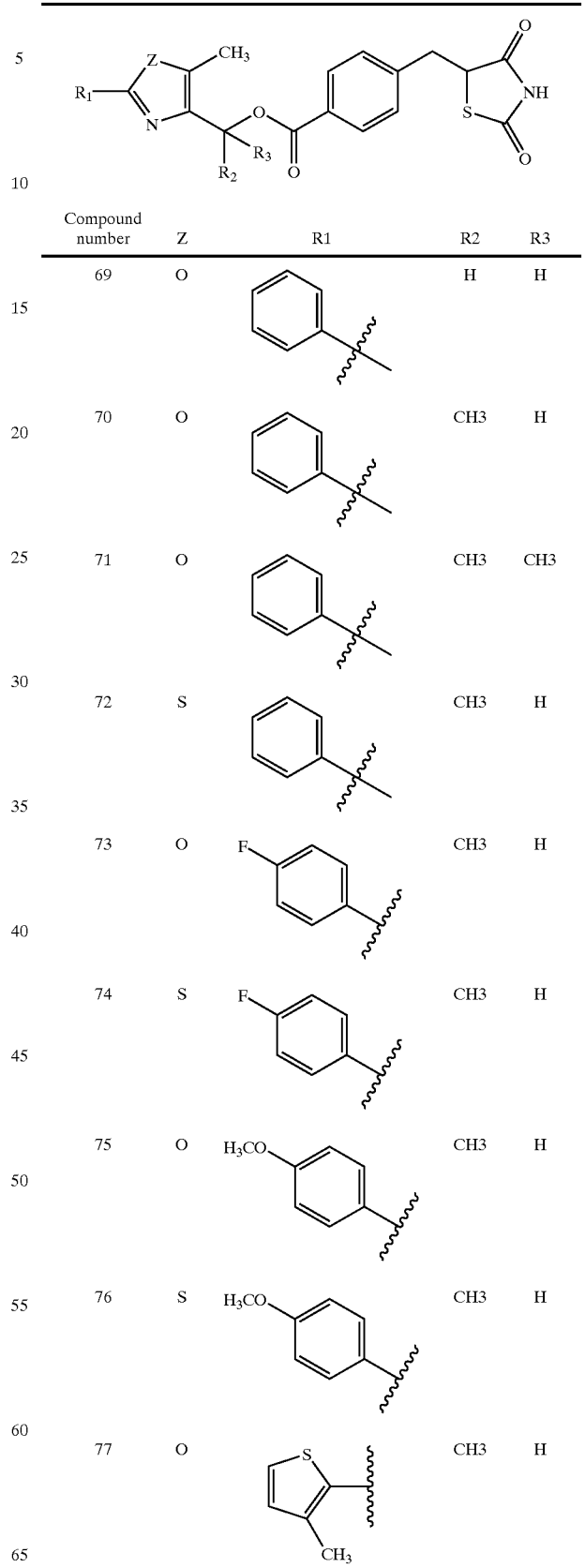

| Compound number | Z | R1 | R2 | R3 |
|---|---|---|---|---|
| 69 | O | phenyl | H | H |
| 70 | O | phenyl | CH3 | H |
| 71 | O | phenyl | CH3 | CH3 |
| 72 | S | phenyl | CH3 | H |
| 73 | O | 4-fluorophenyl | CH3 | H |
| 74 | S | 4-fluorophenyl | CH3 | H |
| 75 | O | 4-methoxyphenyl | CH3 | H |
| 76 | S | 4-methoxyphenyl | CH3 | H |
| 77 | O | 3-methyl-thiophen-2-yl | CH3 | H |

TABLE IV-continued

[Structure: R1-substituted Z/N heterocycle with CH3, connected via C(R2)(R3)-O-C(=O)- to a phenyl-CH2-thiazolidinedione]

| Compound number | Z | R1 | R2 | R3 |
|---|---|---|---|---|
| 78 | S | 2,3-dimethylthiophen-yl (3-methylthiophen-2-yl) | CH3 | H |
| 79 | O | 5-methylthiophen-2-yl | H | H |
| 80 | O | 5-methylthiophen-2-yl | CH3 | H |
| 81 | S | 5-methylthiophen-2-yl | H | H |
| 82 | O | 5-methylisoxazol-3-yl | CH3 | H |
| 83 | S | 5-methylisoxazol-3-yl | H | H |
| 84 | O | pyridin-2-yl | CH3 | H |
| 85 | O | pyridin-4-yl | CH3 | H |
| 86 | O | pyrazin-2-yl | CH3 | H |

TABLE V

[Structure: R1-substituted Z/N heterocycle with CH3, connected via C(R2)(R3)-O-C(=O)- to a phenyl-CH=thiazolidinedione]

| Compound number | Z | R1 | R2 | R3 |
|---|---|---|---|---|
| 87 | O | phenyl | H | H |
| 88 | O | phenyl | CH3 | H |
| 89 | O | phenyl | CH3 | CH3 |
| 90 | S | phenyl | CH3 | H |
| 91 | O | 4-fluorophenyl | CH3 | H |
| 92 | S | 4-fluorophenyl | CH3 | H |
| 93 | O | 4-methoxyphenyl | CH3 | H |
| 94 | S | 4-methoxyphenyl | CH3 | H |
| 95 | O | 3-methylthiophen-2-yl | CH3 | H |

TABLE V-continued (structure with Z, R1, R2, R3 substituents on thiazolidinedione-benzylidene core)

| Compound number | Z | R1 | R2 | R3 |
|---|---|---|---|---|
| 96 | S | 3-methylthiophen-2-yl | CH3 | H |
| 97 | O | 5-methylthiophen-2-yl | H | H |
| 98 | O | 5-methylthiophen-2-yl | CH3 | H |
| 99 | S | 5-methylthiophen-2-yl | H | H |
| 100 | O | 5-methylisoxazol-3-yl | CH3 | H |
| 101 | S | 5-methylisoxazol-3-yl | H | H |
| 102 | O | pyridin-2-yl | CH3 | H |
| 103 | O | pyridin-4-yl | CH3 | H |
| 104 | O | pyrazin-2-yl | CH3 | H |

TABLE VI (pyrrolidine-carboxylate linked to thiazolidinedione-benzyl core with Y substituent on N)

| Compound number | Y |
|---|---|
| 105 | benzoxazol-2-yl |
| 106 | benzothiazol-2-yl |
| 107 | pyridin-2-yl |
| 108 | 4,5-dimethylthiazol-2-yl |
| 109 | (2-methyl-6-hydroxy-5,7,8-trimethylchroman-2-yl)carbonyl |
| 110 | (2-methyl-6-hydroxy-5,7,8-trimethylchroman-2-yl)carbonyl (stereoisomer) |
| 111 | (2-methyl-6-hydroxy-5,7,8-trimethylchroman-2-yl)methyl |

TABLE VI-continued

[Structure: Y-N-pyrrolidine-C(=O)-O-phenyl-CH2-thiazolidine-2,4-dione]

| Compound number | Y |
|---|---|
| 112 | [2,5,7,8-tetramethyl-6-hydroxy-chroman-2-yl-methyl group] |
| 113 | [2,2,4,6,7-pentamethyl-5-hydroxy-2,3-dihydrobenzofuran-3-yl-C(=O)- group] |
| 114 | [2,2,4,6,7-pentamethyl-5-hydroxy-2,3-dihydrobenzofuran-3-yl-C(=O)- group] |

TABLE VII

[Structure: Y-N-pyrrolidine-C(=O)-O-phenyl-CH=thiazolidine-2,4-dione]

| Compound number | Y |
|---|---|
| 115 | benzoxazol-2-yl |
| 116 | benzothiazol-2-yl |

TABLE VII-continued

[Structure: Y-N-pyrrolidine-C(=O)-O-phenyl-CH=thiazolidine-2,4-dione]

| Compound number | Y |
|---|---|
| 117 | pyridin-2-yl |
| 118 | 4,5-dimethylthiazol-2-yl |
| 119 | [2,5,7,8-tetramethyl-6-hydroxy-chroman-2-yl-C(=O)- group] |
| 120 | [2,5,7,8-tetramethyl-6-hydroxy-chroman-2-yl-C(=O)- group] |
| 121 | [2,5,7,8-tetramethyl-6-hydroxy-chroman-2-yl-methyl group] |
| 122 | [2,5,7,8-tetramethyl-6-hydroxy-chroman-2-yl-methyl group] |

TABLE VII-continued

[Structure: Pyrrolidine-Y with carboxylate ester to phenyl-CH=thiazolidinedione]

| Compound number | Y |
|---|---|
| 123 | 2,3-dihydro-5-hydroxy-2,2,4,6,7-pentamethylbenzofuran-3-yl carbonyl (with H wedge) |
| 124 | 2,3-dihydro-5-hydroxy-2,2,4,6,7-pentamethylbenzofuran-3-yl carbonyl (opposite stereochemistry) |

TABLE VIII

[Structure: Pyrrolidine-Y with carboxylate ester to phenyl-CH₂-thiazolidinedione]

| Compound number | Y |
|---|---|
| 125 | benzoxazol-2-yl |
| 126 | benzothiazol-2-yl |
| 127 | pyridin-2-yl |
| 128 | 4,5-dimethylthiazol-2-yl |

TABLE VIII-continued

[Structure: Pyrrolidine-Y with carboxylate ester to phenyl-CH₂-thiazolidinedione]

| Compound number | Y |
|---|---|
| 129 | 6-hydroxy-2,5,7,8-tetramethylchroman-2-yl carbonyl |
| 130 | 6-hydroxy-2,5,7,8-tetramethylchroman-2-yl carbonyl (alternative stereochem) |
| 131 | 6-hydroxy-2,5,7,8-tetramethylchroman-2-yl methylene |
| 132 | 6-hydroxy-2,5,7,8-tetramethylchroman-2-yl methylene (alternative) |
| 133 | 2,3-dihydro-5-hydroxy-2,2,4,6,7-pentamethylbenzofuran-3-yl carbonyl |

TABLE VIII-continued
| Compound number | Y |
|---|---|
| 134 | |
TABLE IX
| Compound number | Y |
|---|---|
| 135 | benzoxazol-2-yl |
| 136 | benzothiazol-2-yl |
| 137 | pyridin-2-yl |
| 138 | 4,5-dimethylthiazol-2-yl |
| 139 | |
TABLE IX-continued
| Compound number | Y |
|---|---|
| 140 | |
| 141 | |
| 142 | |
| 143 | |
| 144 | |
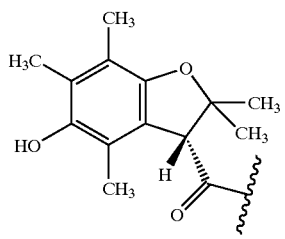

TABLE X
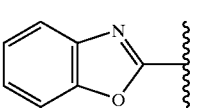
| Compound number | Y |
|---|---|
| 145 | 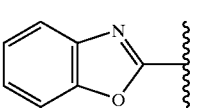 |
| 146 | 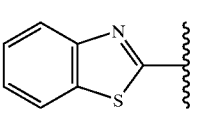 |
| 147 | 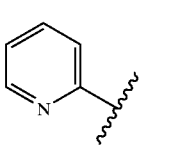 |
| 148 | 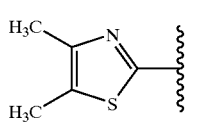 |
| 149 | 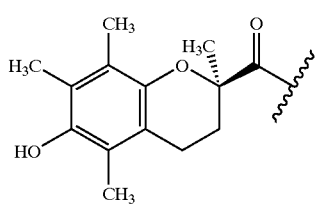 |
| 150 | 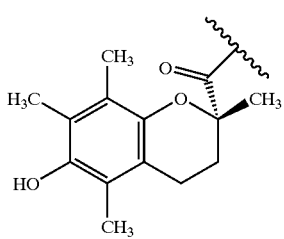 |
| 151 | 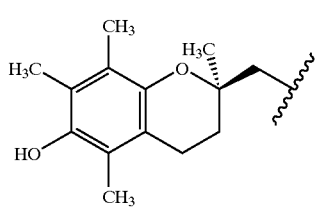 |
TABLE X-continued
| Compound number | Y |
|---|---|
| 152 | |
| 153 | |
| 154 | |
TABLE XI
| Compound number | Y |
|---|---|
| 155 | |
| 156 | |

TABLE XI-continued
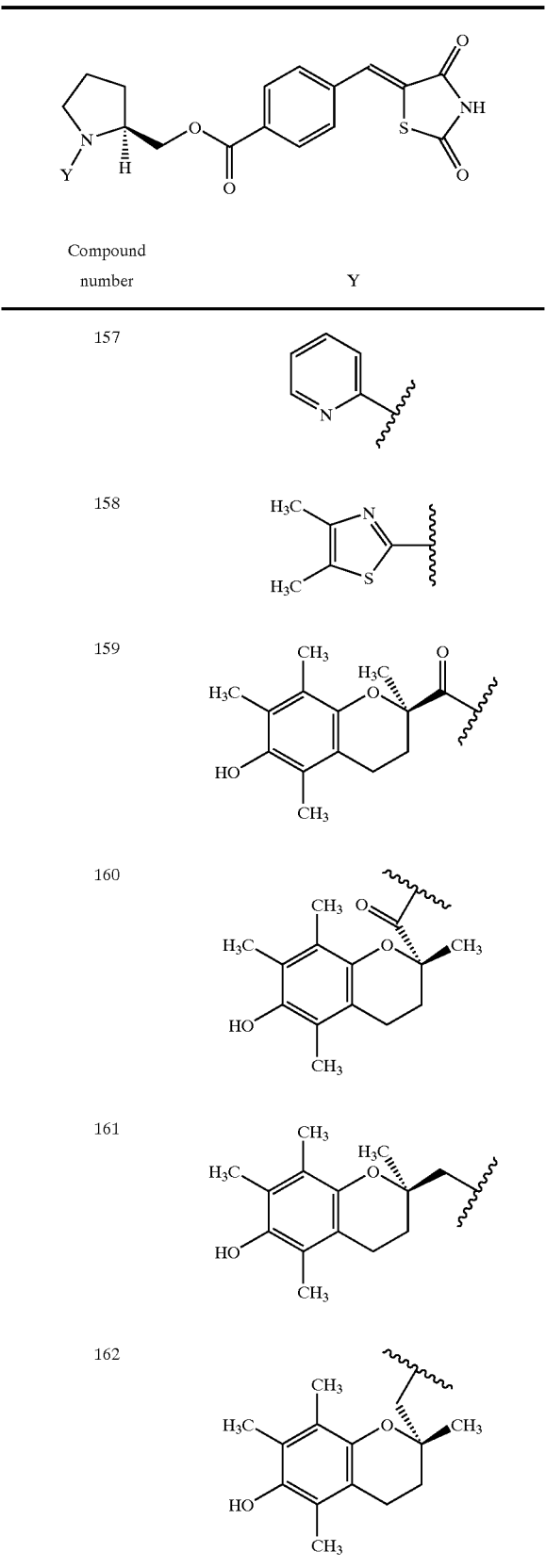
TABLE XI-continued
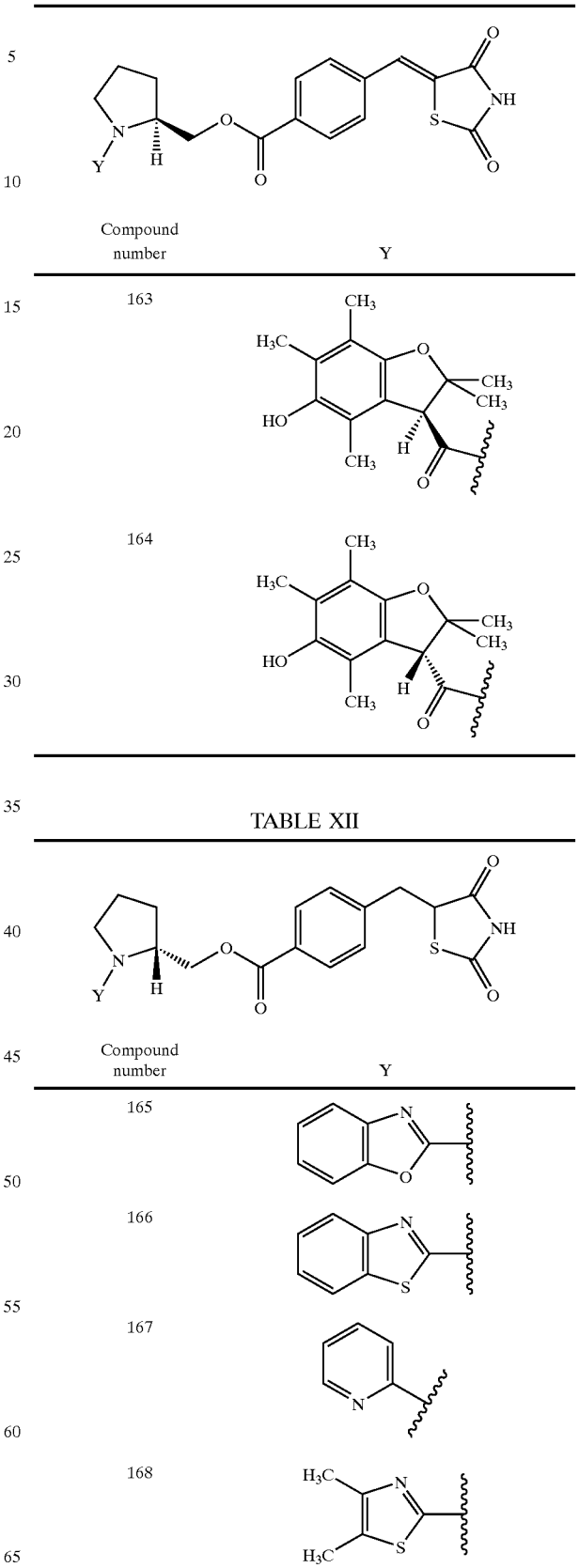

TABLE XII-continued

[Structure: pyrrolidine-CH2-O-C(=O)-phenyl-CH2-thiazolidinedione, with N-Y]

| Compound number | Y |
|---|---|
| 169 | [chroman with 2-CH3, 5,7,8-trimethyl, 6-OH, 2-C(=O)- attachment] |
| 170 | [chroman with 2-CH3, 5,7,8-trimethyl, 6-OH, 2-C(=O)- attachment (different stereo)] |
| 171 | [chroman with 2-CH3, 5,7,8-trimethyl, 6-OH, 2-CH2- attachment] |
| 172 | [chroman with 2-CH3, 5,7,8-trimethyl, 6-OH, 2-CH2- attachment] |
| 173 | [benzofuran with 2,2-diMe, 4,6,7-triMe, 5-OH, 3-C(=O)- attachment] |

TABLE XII-continued

[Structure: pyrrolidine-CH2-O-C(=O)-phenyl-CH2-thiazolidinedione, with N-Y]

| Compound number | Y |
|---|---|
| 174 | [benzofuran with 2,2-diMe, 4,6,7-triMe, 5-OH, 3-C(=O)- attachment] |

TABLE XIII

[Structure: pyrrolidine-CH2-O-C(=O)-phenyl-CH=thiazolidinedione, with N-Y]

| Compound number | Y |
|---|---|
| 175 | benzoxazol-2-yl |
| 176 | benzothiazol-2-yl |
| 177 | pyridin-2-yl |
| 178 | 4,5-dimethylthiazol-2-yl |
| 179 | [chroman with 2-CH3, 5,7,8-trimethyl, 6-OH, 2-C(=O)- attachment] |

TABLE XIII-continued
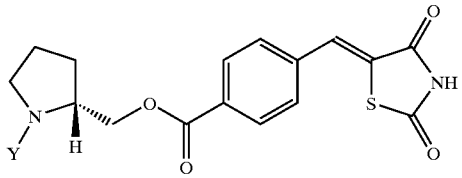
| Compound number | Y |
|---|---|
| 180 | 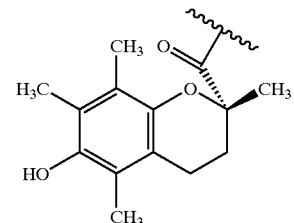 |
| 181 | 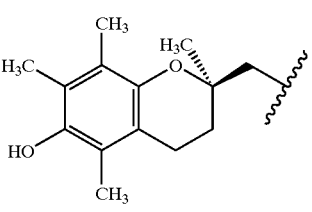 |
| 182 | 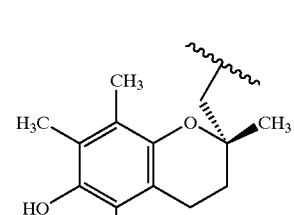 |
| 183 | 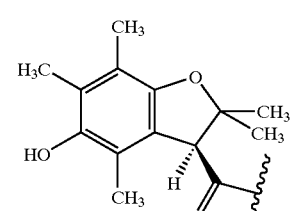 |
| 184 | 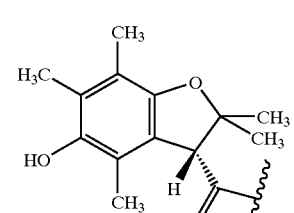 |
TABLE XIV
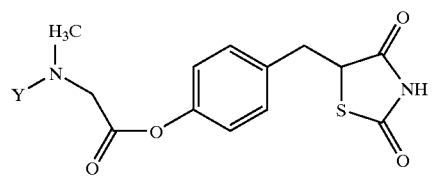
| Compound number | Y |
|---|---|
| 185 | 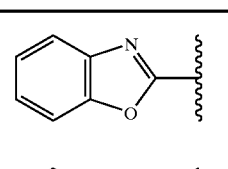 |
| 186 | 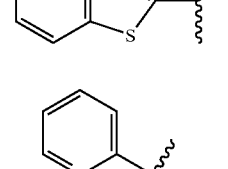 |
| 187 | 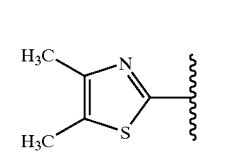 |
| 188 | 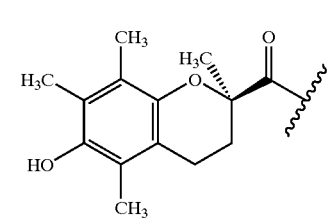 |
| 189 | 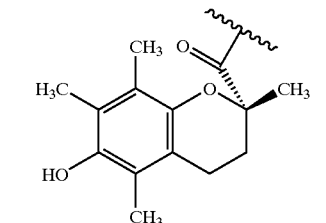 |
| 190 | 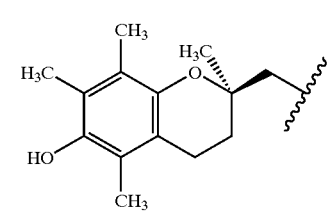 |
| 191 | 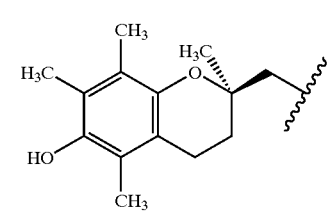 |

TABLE XIV-continued
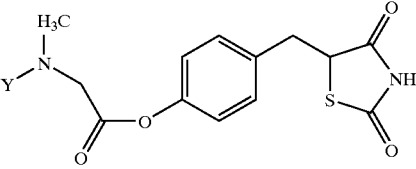
| Compound number | Y |
|---|---|
| 192 | 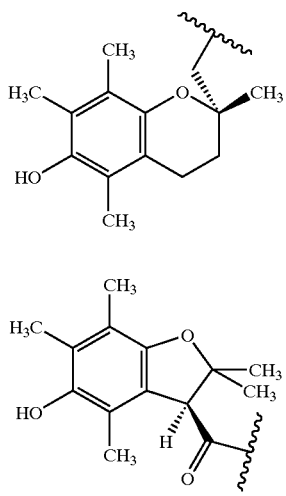 |
| 193 | 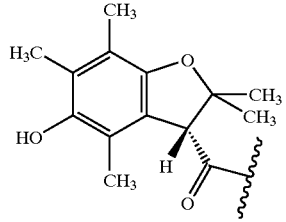 |
| 194 | 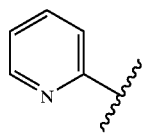 |
TABLE XV
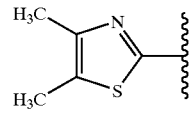
| Compound number | Y |
|---|---|
| 195 | 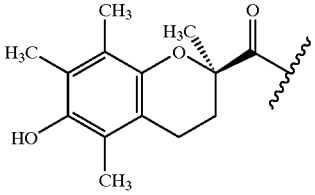 |
| 196 | 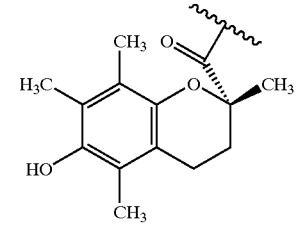 |
TABLE XV-continued
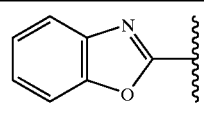
| Compound number | Y |
|---|---|
| 197 | 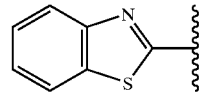 |
| 198 | 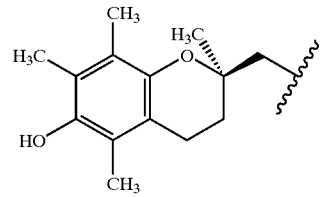 |
| 199 | 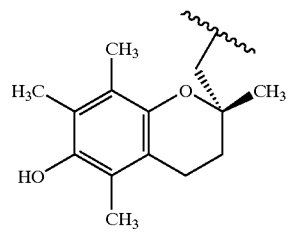 |
| 200 | |
| 201 | |
| 202 | |

TABLE XV-continued
| Compound number | Y |
|---|---|
| 203 | 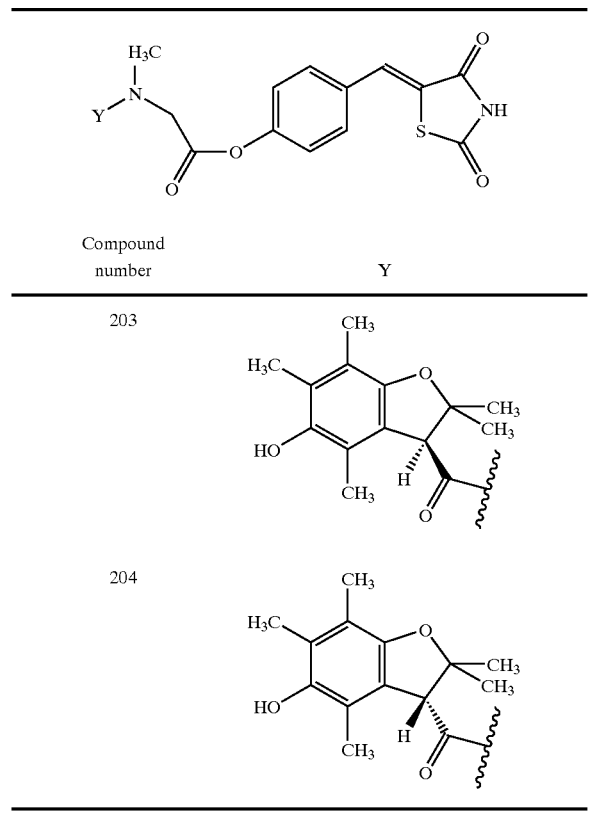 |
| 204 | |
TABLE XVI
| Compound number | Y |
|---|---|
| 205 | |
| 206 | |
| 207 | |
| 208 | |
TABLE XVI-continued
| Compound number | Y |
|---|---|
| 209 | 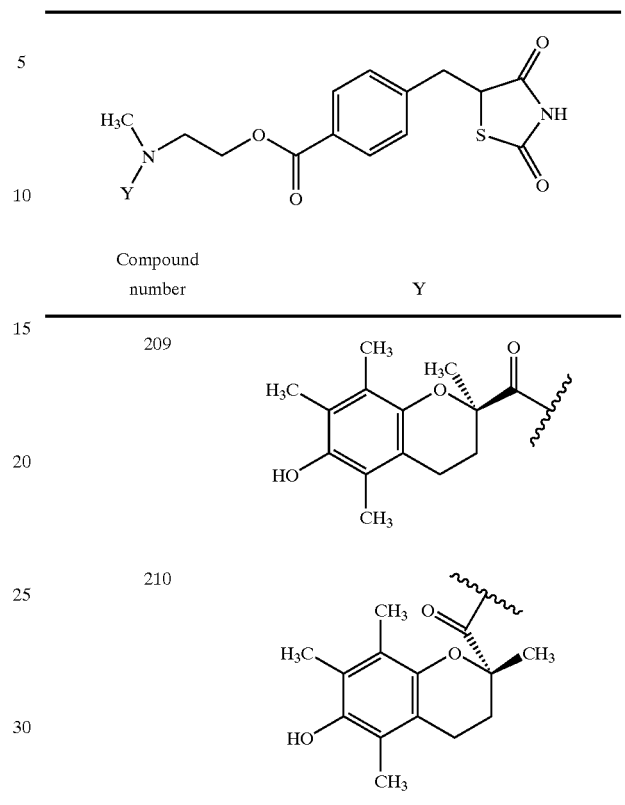 |
| 210 | |
| 211 | |
| 212 | |
| 213 | |
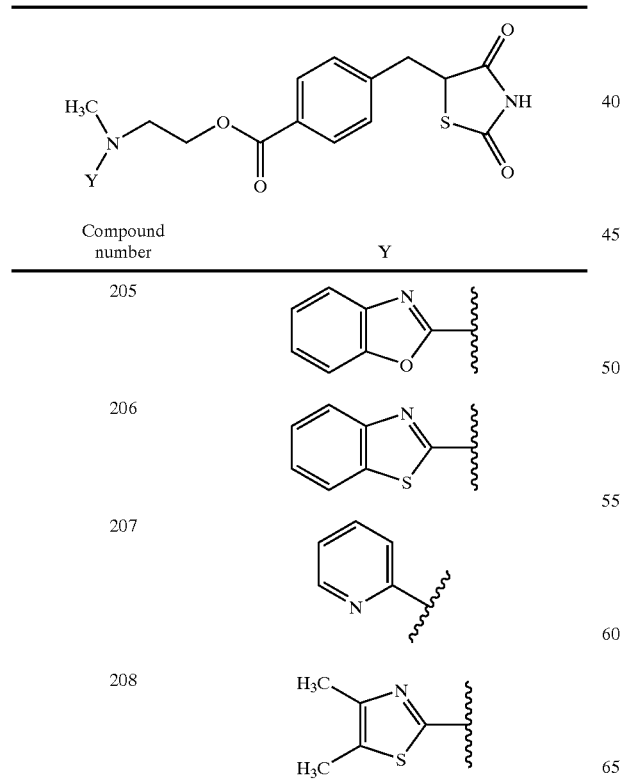
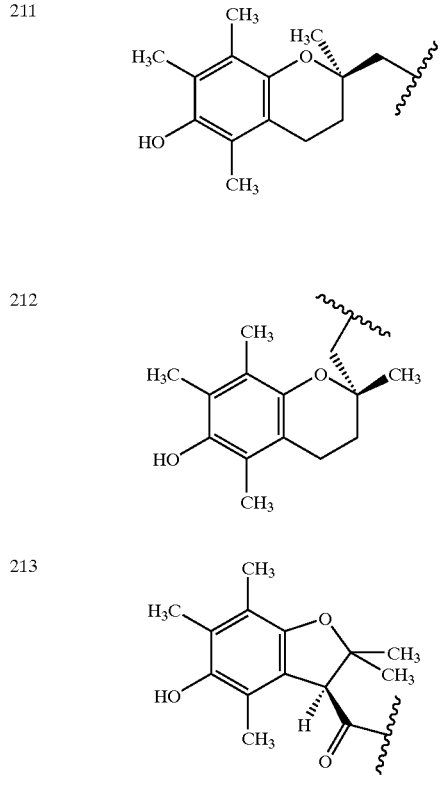

TABLE XVI-continued
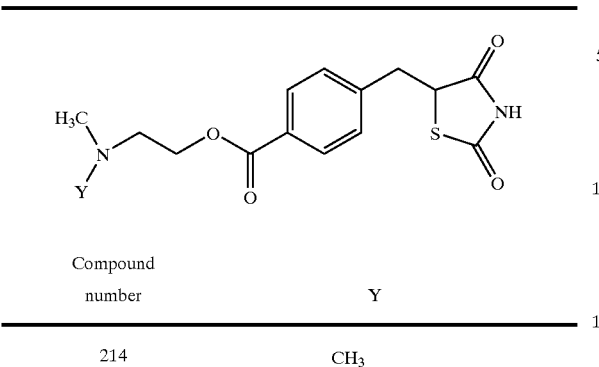
| Compound number | Y |
|---|---|
| 214 | 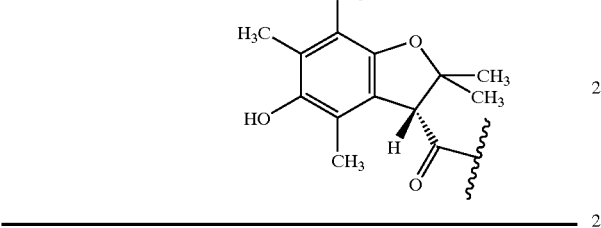 |
TABLE XVII
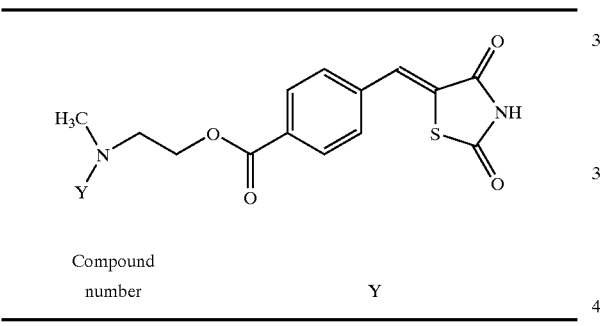
| Compound number | Y |
|---|---|
| 215 | 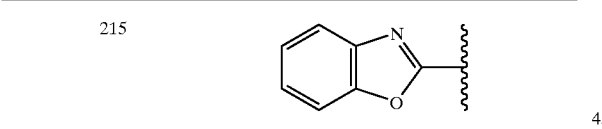 |
| 216 | 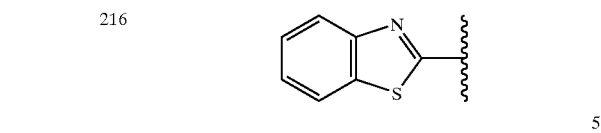 |
| 217 | 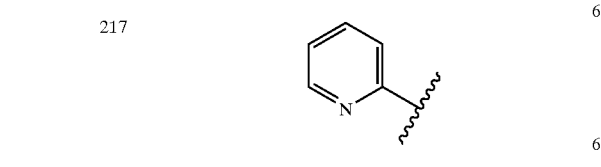 |
TABLE XVII-continued
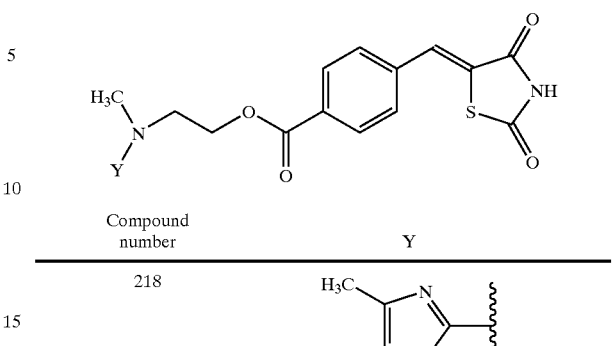
| Compound number | Y |
|---|---|
| 218 | 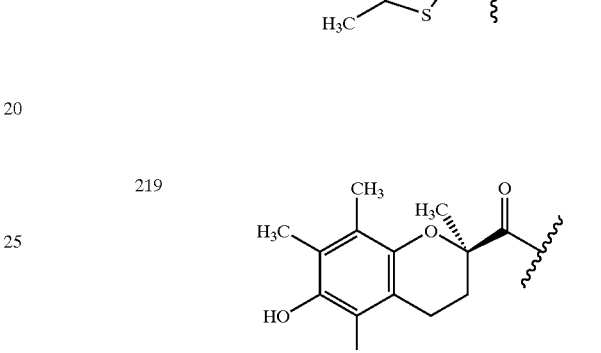 |
| 219 | 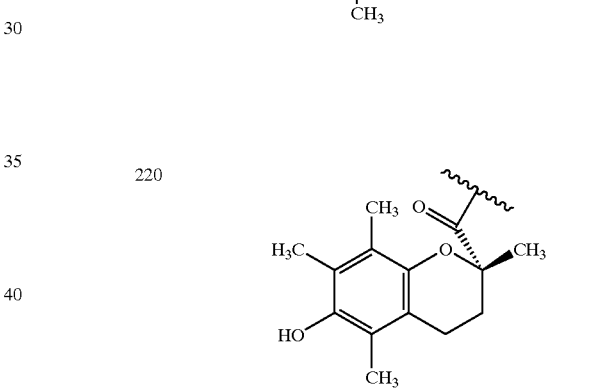 |
| 220 | 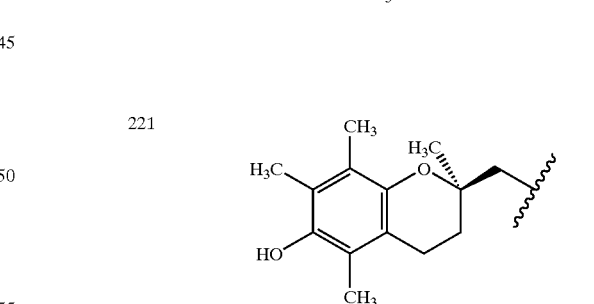 |
| 221 | 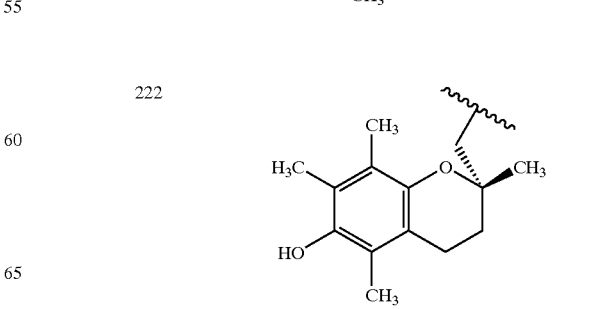 |
| 222 | |

TABLE XVII-continued

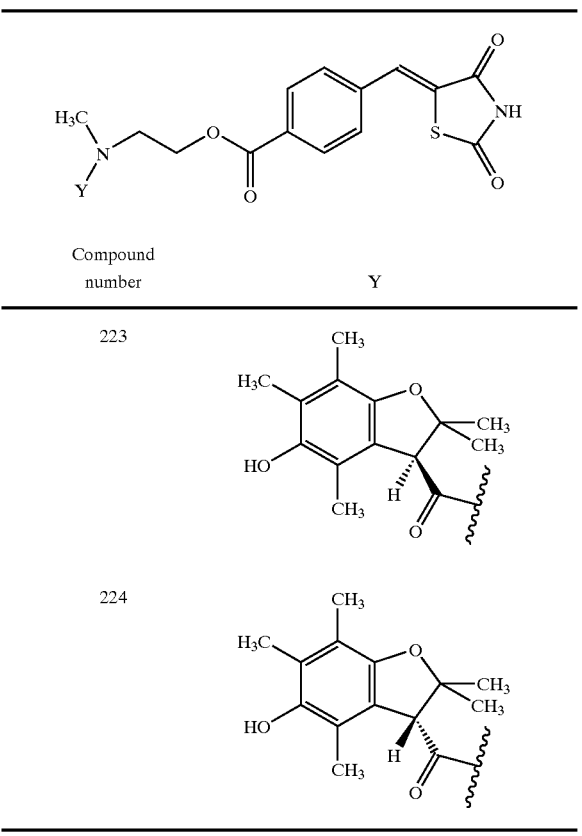

| Compound number | Y |
|---|---|
| 223 | (2,3-dihydro-5-hydroxy-2,2,4,6,7-pentamethylbenzofuran-3-yl)carbonyl |
| 224 | (2,3-dihydro-5-hydroxy-2,2,4,6,7-pentamethylbenzofuran-3-yl)carbonyl (enantiomer) |

TABLE XVIII

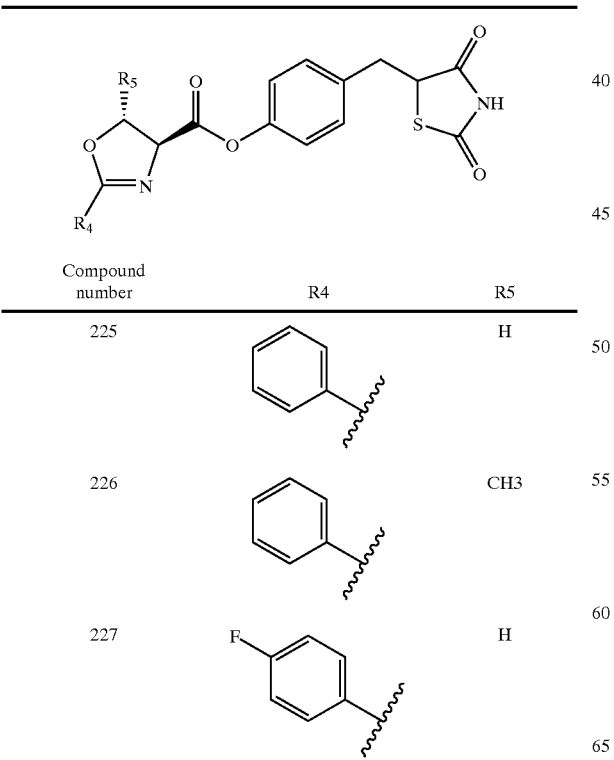

| Compound number | R4 | R5 |
|---|---|---|
| 225 | phenyl | H |
| 226 | phenyl | CH3 |
| 227 | 4-F-phenyl | H |

TABLE XVIII-continued

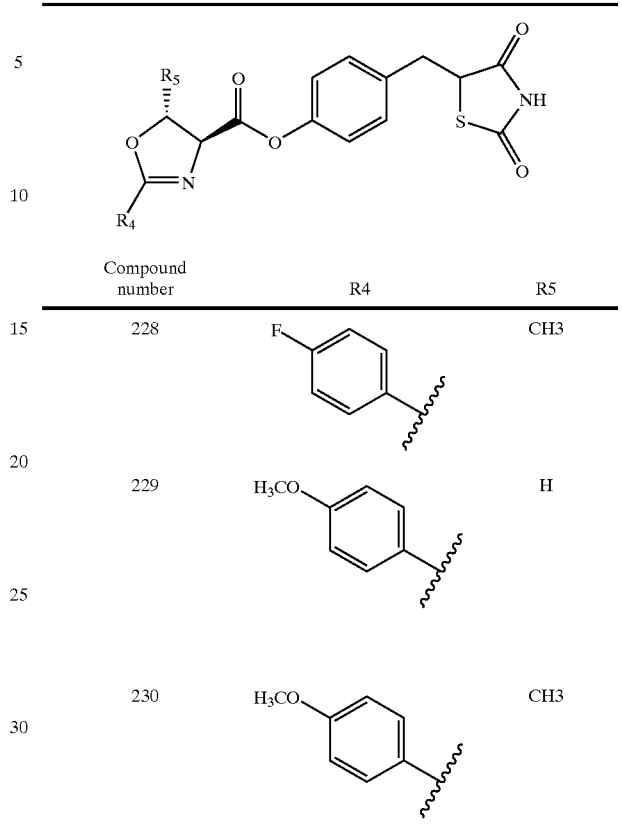

| Compound number | R4 | R5 |
|---|---|---|
| 228 | 4-F-phenyl | CH3 |
| 229 | 4-H3CO-phenyl | H |
| 230 | 4-H3CO-phenyl | CH3 |
| 231 | 3-methylthiophen-2-yl | H |
| 232 | 3-methylthiophen-2-yl | CH3 |
| 233 | 5-methylthiophen-2-yl | H |
| 234 | 5-methylthiophen-2-yl | CH3 |
| 235 | 5-methylisoxazol-3-yl | H |
| 236 | 5-methylisoxazol-3-yl | CH3 |

TABLE XVIII-continued
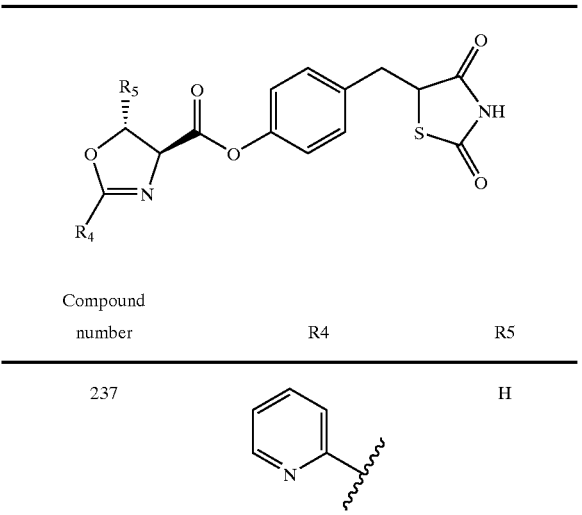
| Compound number | R4 | R5 |
|---|---|---|
| 237 | 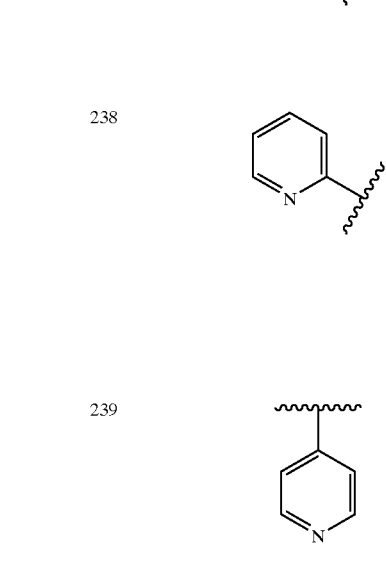 | H |
| 238 | | CH3 |
| 239 | 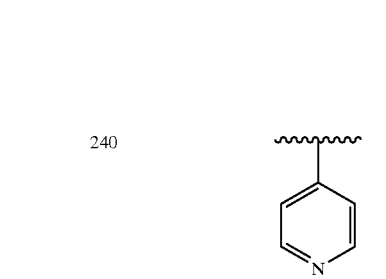 | H |
| 240 | | CH3 |
| 241 | 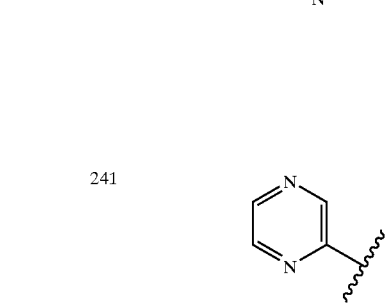 | H |
TABLE XVIII-continued
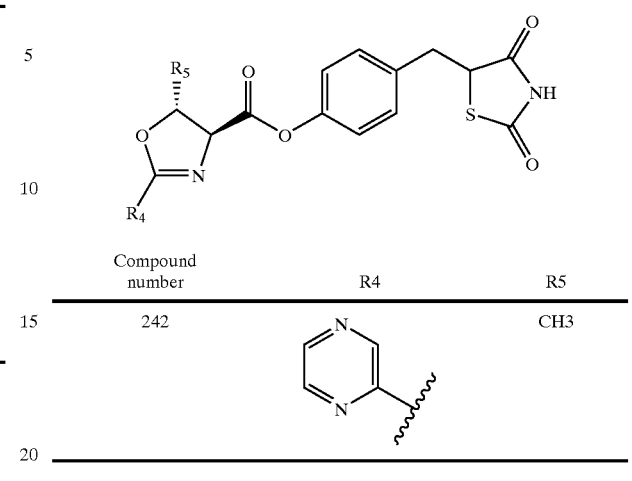
| Compound number | R4 | R5 |
|---|---|---|
| 242 | | CH3 |
TABLE XIX
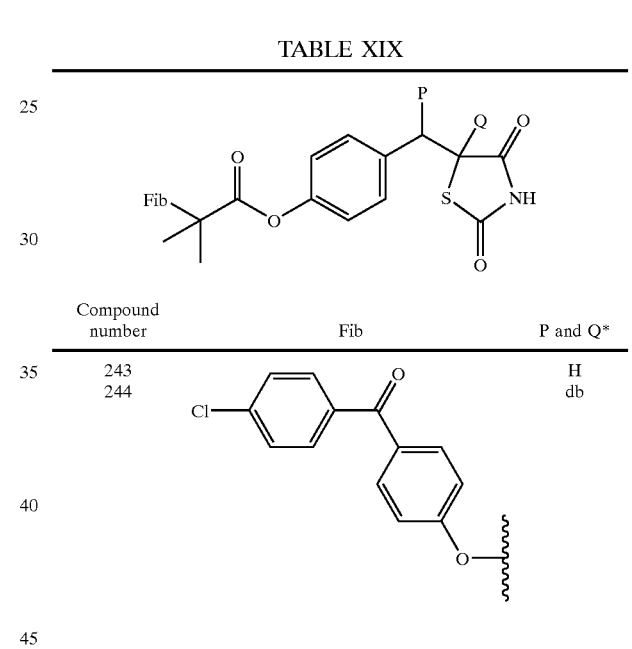
| Compound number | Fib | P and Q* |
|---|---|---|
| 243 | | H |
| 244 | | db |
| 245 | | H |
| 246 | | db |
| 247 | 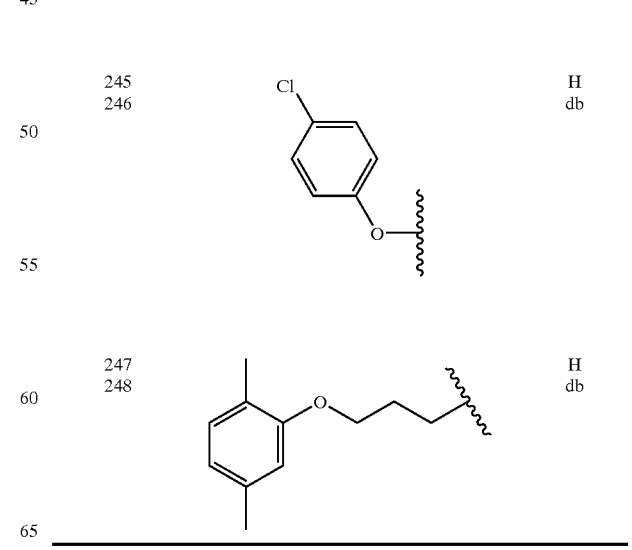 | H |
| 248 | | db |

TABLE XX

| Compound number | Hetero | P and Q* |
|---|---|---|
| 249 | (atorvastatin-derived group) | H |
| 250 | | db |
| 251 | (simvastatin-derived group) | H |
| 252 | | db |

TABLE XXI

| Compound number | NSAID | P and Q* |
|---|---|---|
| 253 | (6-methoxy-2-naphthyl) | H |
| 254 | | db |
| 255 | (6-methoxynaphthyl-CH2-) | H |
| 256 | | db |

TABLE XXI-continued
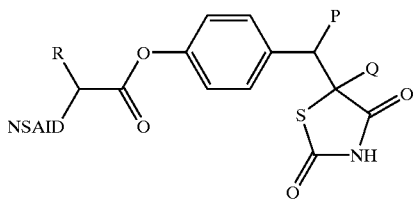
| Compound number | NSAID | P and Q* |
|---|---|---|
| 257 258 | 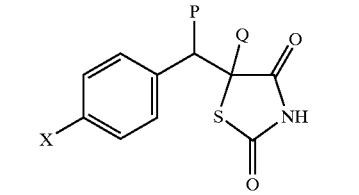 | H db |
| 259 260 | | H db |
TABLE XXII
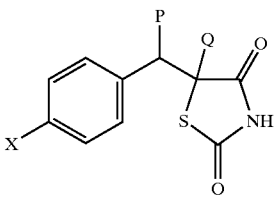
| Compound number | X | P and Q* |
|---|---|---|
| 261 262 | 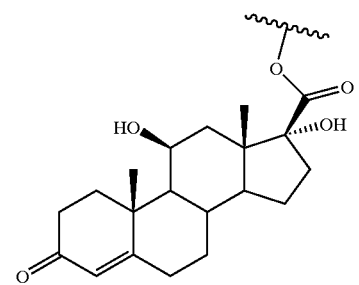 | H db |
| 263 264 | | H db |
| 265 266 | | H db |
| 267 268 | | H db |
TABLE XXIII
Activity in NIDDM Mice.
| Compound | Serum Glucose (%) | Serum Insulin (%) |
|---|---|---|
| Vehicle | 0 | 1 |
| 105 | 40 | 10 |
| 115 | 36 | 13 |
| 155 | 37 | 9 |
| Troglitazone | 35 | 15 |
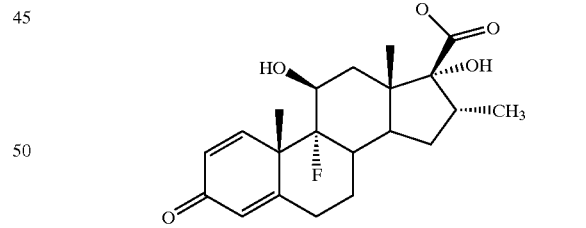

We claim:

1. A compound comprising Formula II:

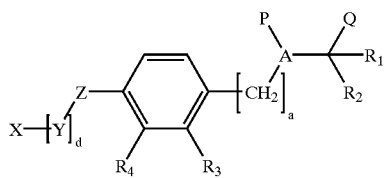

FORMULA II wherein a is 0;

Q is H or CH$_3$;

A is O;

P is absent;

R$_1$ is —(C=O)OH or —(C=O)O—C$_{1-6}$ alkyl; and

R$_2$ is a hydrogen atom; C$_{1-3}$ alkyl; C$_{1-6}$ alkoxy; C$_{0-3}$ alkylenephenyl, wherein the phenyl ring is, optionally, substituted by 1 or more halogen atoms; tetrazole ring; (C=O)OH; (C=O)O—C$_{1-6}$ alkyl; (C=O)$_b$NR$_5$R$_6$, wherein b is 0 or 1; R$_5$ is H or C$_{1-6}$ alkyl, and R$_6$ is H or B(C=O)$_c$DR$_7$ or B(CHOH)$_c$DR$_7$, where c is 0 or 1, B is a bond, a C$_{1-6}$ alkylene, a C$_{2-6}$ alkenylene, a C$_{4-6}$ cycloalkenylene, a phenyl optionally substituted by 1 or more C$_{1-3}$ alkyl groups and/or 1 or more halogen atoms, or a 5- or 6-membered heterocyclic group containing at least 1 or optionally 2 heteroatoms, including any combination of O, N, or S at any position, D is a bond, a C$_{1-3}$ alkyleneoxy, —O—, —NH—, or —N(C$_{1-3}$alkyl)-, R$_7$ is C$_{1-6}$ alkyl, C$_{4-6}$ cycloalkyl or cycloalkenyl, phenyl optionally substituted by 1 or more halogen atoms, C$_{1-3}$ alkyl, C$_{1-3}$ alkoxy, C$_{0-3}$ alkyleneNR$_8$R$_9$ (each of R$_8$ and R$_9$ being independently H, C$_{1-3}$ alkyl, SO$_2$C$_{1-3}$alkyl, (C=O)OC$_{1-3}$ alkyl, SO$_2$NHC$_{1-3}$ alkyl), C$_{0-3}$ alkylene(C=O)OC$_{1-3}$ alkyl, OCH$_2$(C=O)NH$_2$, a 5- or 6-membered heterocyclic ring containing at least 1 or optionally 2 heteroatoms, and including any combination of O, N, or S at any position, or a fused bicyclic ring containing a benzene ring fused with a 5- or 6-membered heterocyclic ring containing at least 1 heteroatom, including O, N, or S at any position, and optionally substituted by an oxo (=O) group, wherein said bicyclic fused ring can be attached to D via a ring atom of the heterocyclic ring either directly or through a C$_{1-6}$ alkylene ER$_{10}$, where E is O, S, or —NR$_{11}$; R$_{10}$ and R$_{11}$ being independently H or C$_{1-3}$ alkyl;

R$_3$ and R$_4$ are, optionally, the same or different and each is H, CH$_3$, CF$_3$, OCH$_3$, or a halogen atom;

d is 1;

X is

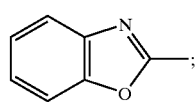

Y is one of the following:

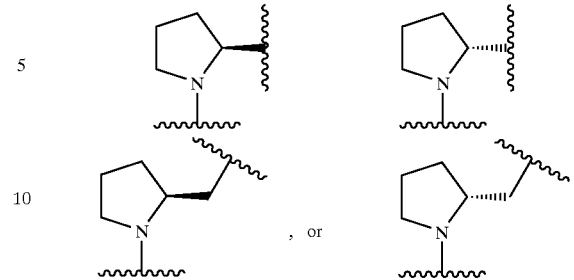

, or in which the nitrogen atom is attached to X as defined above and in which the 2-position of the pyrrolidine ring is attached to Z, either directly or through a methylene group;

Z is —(C=O)O.

2. The compound according to claim 1 comprising Formula VI:

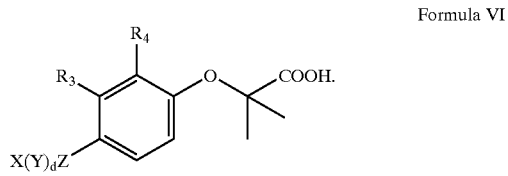

Formula VI

3. The compound according to claim 1 comprising Formula IXA:

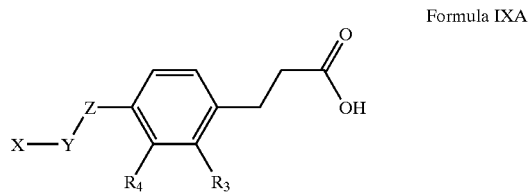

Formula IXA

4. The compound according to claim 3 comprising Formula IXA.

5. A compound according to claim 1, wherein X(Y)$_d$Z are:

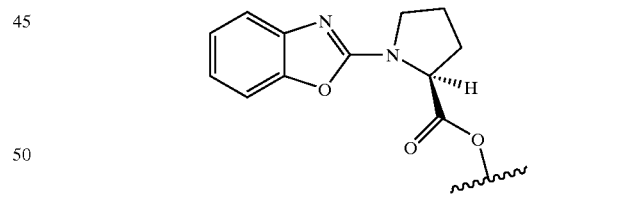

6. A composition comprising a compound according to claim 1 and a carrier.

7. A method of treating diabetes, hyperlipidemia, hypercholesterolemia, or atheroschlerosis comprising the administration of a therapeutically effective amount of a compound according to claim 1 or a composition comprising a compound according to claim 1 and a carrier.

* * * * *